United States Patent [19]
Iwasawa et al.

[11] Patent Number: 6,011,174
[45] Date of Patent: Jan. 4, 2000

[54] CYCLIC AMIC ACID DERIVATIVES

[75] Inventors: Yoshikazu Iwasawa; Tetsuya Aoyama; Kumiko Kawakami; Sachie Arai; Toshihiko Satoh; Yoshiaki Monden, all of Tsukuba, Japan

[73] Assignee: Banyu Pharmaceutical Co., Ltd., Tokyo, Japan

[21] Appl. No.: 09/117,534

[22] PCT Filed: Feb. 7, 1997

[86] PCT No.: PCT/JP97/00303

§ 371 Date: Aug. 4, 1998

§ 102(e) Date: Aug. 4, 1998

[87] PCT Pub. No.: WO97/29078

PCT Pub. Date: Aug. 14, 1997

[30] Foreign Application Priority Data

Feb. 7, 1996 [JP] Japan ................................. 8/045500
Jul. 17, 1996 [JP] Japan ................................. 8/206673

[51] Int. Cl.[7] ................ C07C 229/00; C07D 317/00; A61K 31/195; A61K 31/335
[52] U.S. Cl. ............ 562/442; 562/433; 549/452; 549/493; 549/58; 549/77; 546/335; 546/336; 514/563; 514/570; 514/463; 514/471; 514/443; 514/438; 514/357
[58] Field of Search ................. 562/442, 433; 514/563, 570, 463, 471, 443, 438, 357; 549/452, 493, 58, 77; 546/335, 336

[56] References Cited

U.S. PATENT DOCUMENTS

| | | |
|---|---|---|
| 3,855,248 | 12/1974 | Lannert et al. . |
| 4,182,718 | 1/1980 | Crutchfield et al. . |
| 5,488,149 | 1/1996 | Nomoto et al. . |
| 5,606,101 | 2/1997 | Nomoto et al. . |
| 5,616,803 | 4/1997 | Nomoto et al. . |
| 5,643,958 | 7/1997 | Iwasawa et al. . |
| 5,777,150 | 7/1998 | Nomoto et al. . |

FOREIGN PATENT DOCUMENTS

| | | |
|---|---|---|
| 7-138214 | 5/1995 | Japan . |
| WO 96/05168 | 2/1996 | WIPO . |
| WO 96/05169 | 2/1996 | WIPO . |

OTHER PUBLICATIONS

Chemical Abstracts, vol. 60, No. 10, May 11, 1964, Abstract No. 11924g.

*Primary Examiner*—Deborah C. Lambkin
*Attorney, Agent, or Firm*—Oblon, Spivak, McClelland, Maier & Neustadt, P.C.

[57] ABSTRACT

The present invention relates to a compound of the formula (I), or its pharmaceutically acceptable salt or ester:

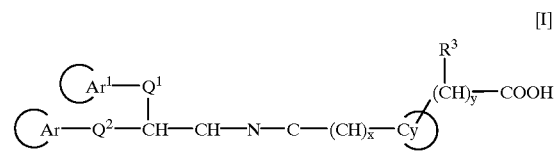

wherein $Ar^1$ is an aryl group or a heteroaromatic ring group; Ar is a group of the formula

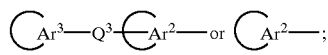

each of $Ar^2$ and $Ar^3$ is an aryl group or a heteroaromatic ring group; Cy is an aryl group, a heteroaromatic ring group or an aliphatic ring group which may contain one or two oxygen atoms; $A^1$ is a $C_{1-4}$ chain hydrocarbon group; m is an integer of from 1 to 6; each of n and p is an integer of from 0 to 3; $Q^1$ is a single bond, a group of the formula $-CH_2O-$, $-OCH_2-$, $-CH_2S-$ or $-SCH_2-$, or a $C_{1-6}$ chain hydrocarbon group; $Q^2$ is a single bond or a group of the formula $-(CH_2)_m-$ or $-(CH_2)_n-W-(CH_2)_p-$; $Q^3$ is a single bond, an oxygen atom, a sulfur atom, a methylene group, a vinylene group or a group of the formula $-CO-$, $-NH-$, $-COO-$, $-OCO-$, $-CH_2CH_2-$, $-OCH_2-$, $-SCH_2-$, $-CH_2O-$, $-CH_2S-$, $-NHCO-$ or $-CONH-$; $R^1$ is a lower alkyl group; each of $R^2$ and $R^3$ is a hydrogen atom, a hydroxyl group or a lower alkyl group; W is an oxygen atom, a sulfur atom, a vinylene group or an ethynylene group; x is an integer of from 0 to 2; and y is 0 or 1; and an antitumor agent containing it as an active ingredient and intermediates for the production thereof.

20 Claims, No Drawings

CYCLIC AMIC ACID DERIVATIVES

This application is a 371 of PCT/JP97/00303 Feb. 7, 1997.

TECHNICAL FIELD

The present invention relates novel cyclic amic acid derivatives. More particularly, the cyclic amic acid derivatives of the present invention inhibit protein-farnesyl transferase (PFT) in vivo thereby to suppress function of oncogene protein Ras and thus present antitumor activities, etc., and they are thus useful in the pharmaceutical field.

BACKGROUND ART

The ras oncogene is activated by mutation, and its translation product Ras protein plays an important role in transformation of normal cells to cancer cells. Such activation of ras oncogene is observed in many cancers such as colorectal cancers or pancreatic cancers, and the proportion thereof is reported to reach about 20% of the total human cancers. Accordingly, it is expected that canceration can be suppressed and antitumor effects can be obtained by suppressing such activation of ras oncogene, by inhibiting the function of Ras protein as its product.

Recently, it has been found that farnesyl-modification of Ras protein itself is essential for function of Ras protein, and it is possible to suppress localization of Ras protein at the plasma membrane by inhibiting this farnesyl-modification and thereby to inhibit transformation to cancer cells. The protein-farnesyl transferase (PFT) is an enzyme which catalyses this farnesyl-modification of Ras protein, and by inhibiting this enzyme, it is possible to suppress function of carcinogenic Ras protein. Further, this enzyme contributes to farnesyl-modification of only very limited proteins in vivo. Accordingly, the inhibitor for such an enzyme is expected to be a safe and highly selective antitumor agent. From such a viewpoint, many PFT inhibitors have been developed in recent years (Cell, vol. 57, p. 1167–1177 (1989); Proc. Natl. Acad. Sci., vol. 86, p. 8323–8327 (1989); ditto, vol. 90, p. 2281–2285 (1993); Science, vol. 245, p. 379–385 (1989); ditto, vol. 260, p. 1934–1937 (1993); ditto, vol. 260, p. 1937–1942 (1993); J. Biol. Chem., vol. 266, p. 15575–15578 (1991); J. Antibiotics, vol. 46, p. 222–227 (1993); Natur Medicine, vol. 1, p. 792–797 (1995); JP-A-5-201869; JP-A-5-213992).

Further, it has recently been found by a research by the present inventors that these PFT inhibitors can block the reactivation of static viruses by suppressing development of matured Ras proteins and are useful as anti-AIDS (HIV) agents (PCT/JP95/02489).

However, up to now, all of the reported PFT inhibitors have had some problems for development as medicines, such that the activities are low in cells, and the effects in vivo are inadequate.

DISCLOSURE OF THE INVENTION

It is an object of the present invention to provide a novel antitumor agent or an anti-AIDS agent which inhibits the protein-farnesyl transferase (PFT) thereby to inhibit functional manifestation of oncogene protein Ras and which thus provides antitumor or anti-AIDS effects.

The present inventors have found that a compound of the formula (I):

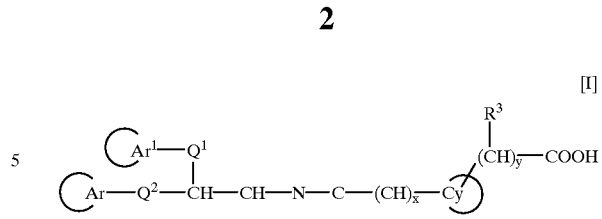

wherein

is an aryl group or a heteroaromatic ring group which may have substituent(s) selected from the group consisting of a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower alkenyl group, a lower hydroxyalkyl group, a lower fluoroalkyl group, a lower alkoxy group, an aryl group and a heteroaromatic ring group;

is a group of the formula

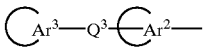

when $Q^2$ is a single bond, or a group of the formula

when $Q^2$ is a group of the formula $-(CH_2)_m-$ or $-(CH_2)_n-W-(CH_2)_p-$; each of

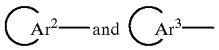

which are the same or different, is an aryl group or a heteroaromatic ring group which may have substituent(s) selected from the group consisting of a halogen atom, a hydroxyl group, an amino group, a nitro group, a cyano group, a carboxyl group, a lower alkoxycarbonyl group, a lower alkylamino group, a carbamoyl group, a lower alkylcarbamoyl group, a lower alkyl group, a lower alkenyl group, a lower hydroxyalkyl group, a lower fluoroalkyl group, a lower alkoxy group and an aralkyloxy group;

is an aryl group, a heteroaromatic ring group or an aliphatic ring group which may contain one or two oxygen atoms, which may have substituent(s) selected from the group consisting of a halogen atom, a hydroxyl group, an oxo group, an amino group, a nitro group, a cyano group, a carboxyl group, a carbamoyl group, a lower alkylcarbamoyl group, a lower carbamoyloxyalkyl group, a lower alkylcarbamoyloxyalkyl group, a lower alkyl group, a lower fluoroalkyl group, a lower hydroxyalkyl group, a lower alkoxy group, a lower alkoxyalkyl group, a sulfo group, a lower alkoxysulfonyl group, a sulfamoyl group, a lower alkylsulfamoyl group, an aryl group, a heteroaromatic ring group and a group of the formula —PO(OR$^4$)(OR$^5$); A$^1$ is a C$_{1-4}$ chain hydrocarbon group which may have substituent(s) selected from the group consisting of a halogen atom, a lower alkyl group, a hydroxyl group, a lower hydroxyalkyl group and a lower alkoxy group; m is an integer of from 1 to 6; each of n and p which are the same or different, is an integer of from 0 to 3; Q$^1$ is a single bond, a group of the formula —CH$_2$O—, —OCH$_2$—, —CH$_2$S— or —SCH$_2$—, or a C$_{1-6}$ chain hydrocarbon group which may have substituent(s) selected from the group consisting of a halogen atom and a lower alkyl group; Q$^2$ is a single bond, or a group of the formula —(CH$_2$)$_m$— or —(CH$_2$)$_n$—W —(CH$_2$)$_p$—; Q$^3$ is a single bond, an oxygen atom, a sulfur atom, a methylene group, a vinylene group, or a group of the formula —CO—, —NH—, —COO—, —OCO—, —CH$_2$CH$_2$—, —OCH$_2$—, —SCH$_2$—, —CH$_2$O—, —CH$_2$S—, —NHCO— or —CONH—; R$^1$ is a lower alkyl group; each of R$^2$ and R$^3$ which are the same or different, is a hydrogen atom, a hydroxyl group or a lower alkyl group; each of R$^4$ and R$^5$ which are the same or different, is a hydrogen atom or a lower alkyl group; W is an oxygen atom, a sulfur atom, a vinylene group or an ethynylene group; x is an integer of from 0 to 2; and y is 0 or 1, inhibits the protein-farnesyl transferase (PFT) thereby to suppress function of oncogene protein Ras, and thus is useful as an antitumor agent or an anti-AIDS agent. The present invention has been accomplished on the basis of this discovery.

Thus, the present invention relates to a compound of the formula (I), or its pharmaceutically acceptable salt or ester, as well as its application and intermediates for its production, i.e. a compound of the formula (II'-a):

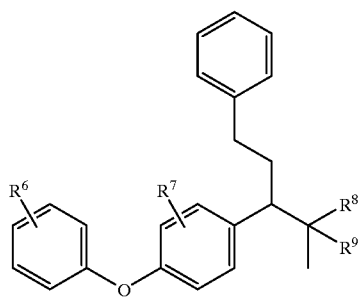

[II'-a]

wherein each of R$^6$ and R$^7$ which are the same or different, is a hydrogen atom, a halogen atom, a lower alkoxy group or an aralkyloxy group; R$^8$ is a hydrogen atom, R$^9$ is a hydroxyl group, an amino group or a group of the formula —OCOR$^z$ or —NHCH$_2$COOR$^{p1}$, or R$^8$ and R$^9$ together form an oxo group; R$^z$ is a lower alkyl group, an aryl group or an aralkyl group; and R$^{p1}$ is a hydrogen atom or a protecting group for a carboxyl group, and a compound of the formula (III'-bb):

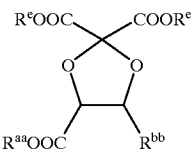

[III'-bb]

wherein R$^{aa}$ is a hydrogen atom, a tert-butyl group, a benzyl group, a benzhydryl group or a trityl group; R$^{bb}$ is a hydrogen atom, a lower alkyl group, an aryl group, a heteroaromatic ring group or a group of the formula —COOR$^b$; R$^b$ is a lower alkyl group; and R$^e$ is a lower alkyl group or a 2-(trimethylsilyl)ethyl group, or two R$^e$ bond to each other to form an isopropylidene group.

Symbols and terms used in this specification will be explained.

The aryl group means a phenyl group, a naphthyl group or an anthryl group. A phenyl group or a naphthyl group is preferred.

The heteroaromatic ring group means a 5-membered or 6-membered monocyclic aromatic heterocyclic group containing one or two hetero atoms, which are the same or different, selected from the group consisting of an oxygen atom, a nitrogen atom and a sulfur atom, or a fused aromatic heterocyclic group having such a monocyclic aromatic heterocyclic group fused with the above-mentioned aryl group or having the same or different such monocyclic,aromatic heterocyclic groups fused with each other, which may, for example, be a pyrrolyl group, an imidazolyl group, a pyrazolyl group, a pyridyl group, a pyrazinyl group, a pyrimidinyl group, a pyridazinyl group, an oxazolyl group, an isoxazolyl group, a furyl group, a thienyl group, a thiazolyl group, an isothiazolyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthylidinyl group, a quinoxalinyl group, a quinazolinyl group, a cinnolinyl group or a pteridinyl group. Among them, a furyl group, a thienyl group, a pyridyl group, a pyrimidinyl group, an oxazolyl group, an isoxazolyl group, a thiazolyl group, a benzofuranyl group, a benzothienyl group, a benzimidazolyl group, a benzoxazolyl group, a benzothiazolyl group or a quinolyl group is preferred.

The aliphatic ring group which may contain one or two oxygen atoms, means a 3-membered to 7-membered saturated or unsaturated aliphatic carbon ring group, or a 3-membered to 7-membered saturated or unsaturated aliphatic oxygen-containing heterocyclic group which contains one or two oxygen atoms, such as a cyclopropyl group, a cyclobutyl group, a cyclopentyl group, a cyclohexyl group, a cycloheptyl group, an oxiranyl group, an oxetanyl group, an oxolanyl group, an oxanyl group, an oxepanyl group, a 1,3-dioxetanyl group, a 1,3-dioxolanyl group, a 1,3-dioxanyl group, a 1,3-dioxepanyl group, a 1,4-dioxepanyl group, a cyclobutenyl group, a cyclopentenyl group, a cyclohexenyl group, a cycloheptenyl group, an oxirenyl group, an oxetyl group, a 2,3-dihydrofuranyl group, a 2,5-dihydrofuranyl group, 3,4-dihydropyranyl group, a 5,6-dihydropyranyl group, a 2,3-dihydrooxepinyl group, a 4,5-dihydrooxepinyl group, a 2,5-dihydrooxepinyl group, a cyclopentadienyl group, a 1,3-cyclohexadienyl group, a 1,4-cyclohexadienyl group, a 2H-pyranyl group, a 4H-pyranyl group, a 2,3,4,5- tetrahydrooxepinyl group, a 2,3,4,7-tetrahydrooxepinyl group, 2,3,6,7-tetrahydrooxepinyl group, a 1,3-dioxolyl group, a 1,3-dioxinyl group, a 1,4-dioxinyl group, a dihydro-1,4-dioxinyl group, a 6,7-dihydro-1,3-dioxepinyl group, a 4,7-dihydro-1,3-dioxepinyl group, a 5,6-dihydro-1,4-dioxepinyl group, a 2,3-dihydro-1,4-dioxepinyl group, a 1,3-dioxepinyl group, or a 1,4-dioxepinyl group. Among them, a cyclobutyl group, a cyclopentyl group, an oxolanyl group or a 1,3-dioxolanyl group is, for example, preferred.

The lower alkyl group means a $C_{1-6}$ linear or branched alkyl group, which may, for example, be a methyl group, an ethyl group, a propyl group, an isopropyl group, a butyl group, a sec-butyl group, a tert-butyl group, a pentyl group or a hexyl group. Among them, a methyl group or an ethyl group is preferred.

The lower hydroxyalkyl group means the above-mentioned lower alkyl group having a hydroxyl group, i.e. a $C_{1-6}$ hydroxyalkyl group, such as a hydroxymethyl group, a 1-hydroxyethyl group, a 2-hydroxyethyl group, a 3-hydroxypropyl group or a 4-hydroxybutyl group. Among them, a hydroxymethyl group or a 2-hydroxyethyl group is preferred.

The lower alkoxy group means a $C_{1-6}$ alkoxy or alkylenedioxy group, which may, for example, be a methoxy group, an ethoxy group, a propoxy group, an isopropoxy group, a butoxy group, a tert-butoxy group, a methylenedioxy group, an ethylenedioxy group or a trimethylenedioxy group. Among them, a methoxy group, an ethoxy group or a methylenedioxy group is preferred.

The lower alkoxyalkyl group means the above-mentioned alkyl group having the above-mentioned alkoxy group, which may, for example, be a methoxymethyl group, an ethoxymethyl group, an ethoxymethyl group, a 1-methoxyethyl group, a 2-methoxyethyl group, a 2-ethoxyethyl group, a 3-methoxypropyl group or a 4-methoxybutyl group. Among them, a methoxymethyl group, an ethoxymethyl group or a 2-methoxyethyl group is, for example, preferred.

The lower carboxyalkyl group means the above-mentioned lower alkyl group having a carboxyl group, i.e. a $C_{1-7}$ carboxyalkyl group, such as a carboxymethyl group, a 1-carboxyethyl group, a 2-carboxyethyl group, a 3-carboxypropyl group or a 4-carboxybutyl group. Among them, a carboxymethyl group or a 2-carboxyethyl group is preferred.

The aralkyl group means the above-mentioned lower alkyl group having the above-mentioned aryl group, such as a benzyl group, a phenethyl group, a 3-phenylpropyl group, a 1-naphthylmethyl group, a 2-naphthylmethyl group or a 1-(2-naphthyl)ethyl group. Among them, a benzyl group, a phenethyl group or a 2-naphthylmethyl group is preferred.

The aralkyloxy group means the above-mentioned alkoxy group having the above-mentioned aryl group, such as a benzyloxy group, a phenethyloxy group, a 3-phenylpropyloxy group, a 1-naphthylmethyloxy group, a 2-naphthylmethyloxy group or a 1-(2-naphthyl)ethyloxy group. Among them, a benzyloxy group, a phenethyloxy group or a 2-naphthylmethyloxy group is, for example, preferred.

The chain hydrocarbon group means a straight chain saturated aliphatic hydrocarbon group, or a straight chain unsaturated aliphatic hydrocarbon group having one or more, preferably one or two double bonds, at optional positions on the carbon chain.

The saturated aliphatic hydrocarbon group may, for example, be a methylene group, an ethylene group, a trimethylene group, a tetramethylene group, a pentamethylene group, a hexamethylene group, a heptamethylene group or an octamethylene group.

The unsaturated aliphatic hydrocarbon group may, for example, be a vinylene group, a propenylene group, a 1-butenylene group, a 2-butenylene group, a 1,3-butadienylene group, a 1-pentenylene group, a 2-pentenylene group, a 1,3-pentadienylene group, a 1,4-pentadienylene group, a 1-hexenylene group, a 2-hexenylene group, a 3-hexenylene group, a 1,3-hexadienylene group, a 1,4-hexadienylene group, a 1,5-hexadienylene group, a 1,3,5-hexatrienylene group, a 1-heptenylene group, a 2-heptenylene group, a 3-heptenylene group, a 1,3-heptadienylene group, a 1,4-heptadienylene group, a 1,5-heptadienylene group, a 1,6-heptadienylene group, a 1,3,5-heptatrienylene group, a 1-octenylene group, a 2-octenylene group, a 3-octenylene group, a 4-octenylene group, a 1,3-octadienylene group, a 1,4-octadienylene group, a 1,5-octadienylene group, a 1,6-octadienylene group, a 1,7-octadienylene group, a 2,4-octadienylene group, a 2,5-octadienylene group, a 2,6-octadienylene group, a 3,5-octadienylene group, a 1,3,5-octatrienylene group, a 2,4,6-octatrienylene group or a 1,3,5,7-octatetraenylene group.

The halogen atom may be a fluorine atom, a chlorine atom, a bromine atom or an iodine atom. For example, a fluorine atom or a chlorine atom is preferred. The lower alkoxycarbonyl group means a $C_{1-7}$ alkoxycarbonyl group, such as a methoxycarbonyl group, an ethoxycarbonyl group, a propoxycarbonyl group, a butoxycarbonyl group or a tert-butoxycarbonyl group. Among them, a methoxycarbonyl group or an ethoxycarbonyl group is preferred.

The lower alkylamino group means an amino group mono-substituted or di-substituted by the above-mentioned lower alkyl group, such as a methylamino group, an ethylamino group, a dimethylamino group or a diethylamino group.

The lower alkylcarbamoyl group means a carbamoyl group mono-substituted or di-substituted by the above-mentioned lower alkyl group, such as a methylcarbamoyl group, an ethylcarbamoyl group, a dimethylcarbamoyl group or a diethylcarbamoyl group.

The lower fluoroalkyl group means the above-mentioned lower alkyl group having fluorine atom(s), i.e. a $C_{1-6}$ fluoroalkyl group, such as a fluoromethyl group, a difluoromethyl group, a trifluoromethyl group, a 1-fluoroethyl group, a 2-fluoroethyl group, a 2,2,2-trifluoroethyl group or a pentafluoroethyl group.

The lower alkenyl group means a $C_{2-6}$ straight chain or branched alkenyl group, such as a vinyl group, a 1-propenyl group, a 2-propenyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, or a 4-pentenyl group.

The lower carbamoyloxyalkyl group means the above-mentioned lower alkyl group having a carbamoyloxy group, i.e. a $C_{1-7}$ carbamoyloxyalkyl group, such as a carbamoyloxymethyl group, a 1-carbamoyloxyethyl group, a 2-carbamoyloxyethyl group, a 3-carbamoyloxypropyl group, or a 4-carbamoyloxybutyl group. Among them, a carbamoyloxymethyl group or a 2-carbamoyloxyethyl group is, for example, preferred.

The lower alkylcarbamoyloxyalkyl group means the above-mentioned lower carbamoyloxyalkyl group mono-substituted or di-substituted by the above-mentioned lower alkyl group, such as a methylcarbamoyloxymethyl group, a 1-methylcarbamoyloxyethyl group, a 2-methylcarbamoyloxyethyl group, an ethylcarbamoyloxymethyl group, a dimethylcarbamoyloxymethyl group, a 1-dimethylcarbamoyloxyethyl group, a 2-dimethylcarbamoyloxyethyl group, or a diethylcarbamoyloxymethyl group. Among them, a methylcarbamoyloxymethyl group, a dimethylcarbamoyloxymethyl group or a 2-dimethylcarbamoyloxyethyl group is, for example, preferred.

The lower alkoxysulfonyl group means a $C_{1-6}$ alkoxysulfonyl group, such as a methoxysulfonyl group, an ethoxysulfonyl group, a propoxysulfonyl group, a butoxysulfonyl group, or a tert-butoxysulfonyl group. Among them, a methoxysulfonyl group or an ethoxysulfonyl group is, for example, preferred.

The lower alkylsulfamoyl group means a sulfamoyl group mono-substituted or di-substituted by the above-mentioned lower alkyl group, such as a methylsulfamoyl group, an ethylsulfamoyl group, a dimethylsulfamoyl group, or a diethylsulfamoyl group.

The salt of the compound of the formula (I) may be a pharmaceutically acceptable common salt, which may, for example, be a base-addition salt of a carboxyl group, or an acid-addition salt of an amino group when the compound has such an amino group, or of a basic heteroaromatic ring when the compound has such a basic heteroaromatic ring.

The base-addition salt may, for example, be an alkali metal salt such as a sodium salt or a potassium salt; an alkaline earth metal salt such as a calcium salt or a magnesium salt; an ammonium salt; or an organic amine salt such as a trimethylamine salt, a triethylamine salt, a dicyclohexylamine salt, an ethanolamine salt, a diethanolamine salt, a triethanolamine salt, a procaine salt or an N,N'-dibenzylethylenediamine salt.

The acid-addition salt may, for example, be an inorganic acid salt such as a hydrochloride, a sulfate, a nitrate, a phosphate or a perchlorate; an organic acid salt such as a maleate, a fumarate, a tartrate, a citrate, an ascorbate or a trifluoroacetate; or a sulfonic acid salt such as a methanesulfonate, an isethionate, a benzenesulfonate or a p-toluenesulfonate.

The ester of the compound of the formula (I) means a pharmaceutically acceptable common ester of the terminal carboxyl group or of a carboxyl group adjacent to $A^1$, or of a carboxyl group if such a carboxy group is present on the group of the

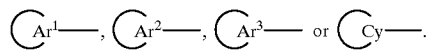

It may, for example, be an ester with a lower alkyl group such as a methyl group, an ethyl group, a propyl group, an isopropyl group, a butyl group, a sec-butyl group, a tert-butyl group, a pentyl group, an isopentyl group, a neopentyl group, a cyclopropyl group, a cyclobutyl group or a cyclopentyl group, an ester with an aralkyl group such as a benzyl group or a phenethyl group, an ester with a lower alkenyl group such as a 2-propenyl group or a 2-butenyl group, an ester with a lower alkoxyalkyl group such as a methoxymethyl group, a 2-methoxyethyl group, a 2-ethoxyethyl group or a 2-propoxyethyl group, an ester with a lower alkanoyloxyalkyl group such as an acetoxymethyl group, a pivaloyloxymethyl group or a 1-pivaloyloxyethyl group, an ester with a lower alkoxycarbonylalkyl group such as a methoxycarbonylmethyl group, an ethoxycarbonylmethyl group or an isopropoxycarbonylmethyl group, an ester with a lower carboxyalkyl group such as a carboxymethyl group, an ester with a lower alkoxycarbonyloxyalkyl group such as a 1-(ethoxycarbonyloxy)ethyl group or a 1-(cyclohexyloxycarbonyloxy)ethyl group, an ester with a lower carbamoyloxy alkyl group such as a carbamoyloxymethyl group, an ester with a phthalidyl group, or an ester with a (5-substituted-2-oxo-1,3-dioxol-4-yl)methyl group such as a (5-methyl-2-oxo-1,3-dioxol-4-yl)methyl group. In addition, it may, for example, be an ester with a lower alkylidene group such as an isopropylidene group or an ester with an aralkylidene group such as a benzylidene group, at two adjacent carboxyl groups when such adjacent carboxyl groups are present.

The compound of the formula (I) covers a compound of the formula (I-a):

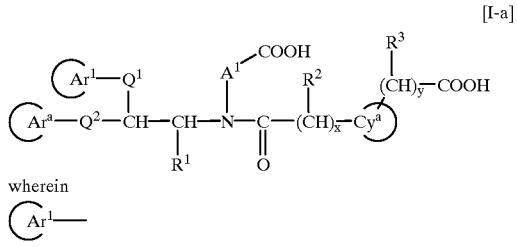

wherein

is an aryl group or a heteroaromatic ring group which may have substituent(s) selected from the group consisting of a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower alkenyl group, a lower hydroxyalkyl group, a lower fluoroalkyl group, a lower alkoxy group, an aryl group and a heteroaromatic ring group;

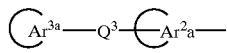

is a group of the formula

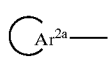

when $Q^2$ is a single bond, or a group of the formula

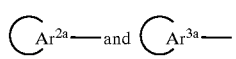

when $Q^2$ is a group of the formula —$(CH_2)_m$— or —$(CH_2)_n$—W—$(CH_2)_p$—; each of Ar²ª— and Ar³ª— which are the same or different, is an aryl group or a heteroaromatic ring group which may have substituent(s) selected from the group consisting of a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower alkenyl group, a lower hydroxyalkyl group, a lower fluoroalkyl group and a lower alkoxy group;

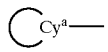

is an aryl group, a heteroaromatic ring group or an aliphatic ring group which may contain one or two oxygen atoms, which may have substituent(s) selected from the group consisting of a halogen atom, a hydroxyl group, an oxo group, an amino group, a carboxyl group, a carbamoyl group, a lower alkylcarbamoyl group, a lower alkyl group and a lower alkoxy group; $A^1$ is a $C_{1-4}$ chain hydrocarbon group which may have substituent(s) selected from the group consisting of a halogen atom, a lower alkyl group, a hydroxyl group, a lower hydroxyalkyl group and a lower alkoxy group; m is an integer of from 1 to 6; each of n and p which are the same or different, is an integer of from 0 to 3; $Q^1$ is a single bond, a group of the formula —CH$_2$O—, —OCH$_2$—, —CH$_2$S— or —SCH$_2$—, or a $C_{1-6}$ chain hydrocarbon group which may have substituent(s) selected from the group consisting of a halogen atom and a lower alkyl group; $Q^2$ is a single bond, or a group of the formula —(CH$_2$)$_m$— or —(CH$_2$)$_n$—W—(CH$_2$)$_p$—; $Q^3$ is a single bond, an oxygen atom, a sulfur atom, a methylene group, a vinylene group, or a group of the formula —CO—, —NH—, —COO—, —OCO—, —CH$_2$CH$_2$—, —OCH$_2$—, —SCH$_2$—, —CH$_2$O—, —CH$_2$S—, —NHCO— or —CONH—; $R^1$ is a lower alkyl group; each of $R^2$ and $R^3$ which are the same or different, is a hydrogen atom, a hydroxyl group or a lower alkyl group; W is an oxygen atom, a sulfur atom, a vinylene group or an ethynylene group; x is an integer of from 0 to 2; and y is 0 or 1.

Further, the compound of the present invention may have stereoisomers such as optical isomers, diastereomers or geometrical isomers, depending upon the form of its substituents. The compound of the present invention includes all of such stereoisomers and their mixtures. Among them, a compound of the formula (I'-1):

[I'-1]

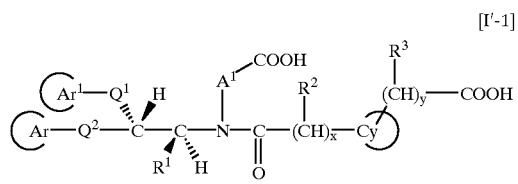

or the formula (I'-2):

[I'-2]

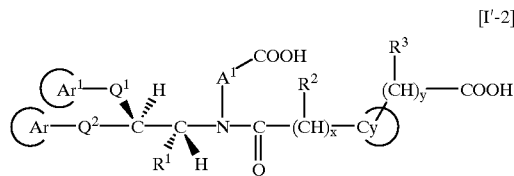

wherein

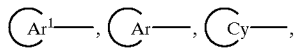

$A^1$, $Q^1$, $Q^2$, $R^1$, $R^2$, $R^3$, x and y are as defined above, is preferred.

means an aryl group or a heteroaromatic ring group which may have substituent(s) selected from the group consisting of a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower alkenyl group, a lower hydroxyalkyl group, a lower fluoroalkyl group, a lower alkoxy group, an aryl group and a heteroaromatic ring group.

The aryl group or the heteroaromatic ring group which may have substituent(s) selected from the group consisting of a halogen atom, a hydroxyl group, an amino group, a nitro group, a cyano group, a carboxyl group, a lower alkoxycarbonyl group, a carbamoyl group, a lower alkyl group, a lower alkenyl group, a lower hydroxyalkyl group, a lower fluoroalkyl group, a lower alkoxy group, an aryl group and a heteroaromatic ring group, means the above-mentioned aryl group or the above-mentioned heteroaromatic ring group which is unsubstituted, or the above-mentioned aryl group or the above-mentioned heteroaromatic ring group which has substituent(s) at optional position(s) for substitution, and said substituent(s) may be one or more, preferably one or two, which may be the same or different and which are selected from the group consisting of a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower alkenyl group, a lower hydroxyalkyl group, a lower fluoroalkyl group, a lower alkoxy group, an aryl group and a heteroaromatic ring group.

may, preferably, be a phenyl group, a thienyl group, a naphthyl group, a pyridyl group or a benzothienyl group, particularly preferably a phenyl group, a thienyl group or a naphthyl group.

The aryl group and the heteroaromatic ring group as substituents of

mean the above-mentioned aryl group or the above-mentioned heteroaromatic ring group which is unsubstituted, or the above-mentioned aryl group or the above-mentioned heteroaromatic ring group which has substituent(s) at optional position(s) for substitution, and said substituent(s) may be one or more which are the same or different and which are selected from the group consisting of a halogen atom, a lower alkyl group and a lower alkoxy group.

Accordingly, specific examples of

include a phenyl group, a 1-naphthyl group, a 2-naphthyl group, a 2-benzofuranyl group, a 2-benzothienyl group, a 2,3-methylenedioxyphenyl group, a 3,4-methylenedioxyphenyl group, a 2-methoxyphenyl group, a 3-methoxyphenyl group, a 4-methoxyphenyl group, a 2-methylphenyl group, a 3-methylphenyl group, a 4-methylphenyl group, a 2-pyridyl group, a 3-pyridyl group, a 4-pyridyl group, a 2-thienyl group, a 3-thienyl group, a 2-furyl group, a 3-furyl group, a 2-quinolyl group, a 2-fluorophenyl group, a 3-fluorophenyl group, a 4-fluorophenyl group, a 2,3-dichlorophenyl group, a 3,4-dichlorophenyl group, a 2-chlorophenyl group, a 3-chlorophenyl group and a 4-chlorophenyl group. Among them, a phenyl group, a 1-naphthyl group, a 2-naphthyl group, a 2-benzothienyl group, a 2,3-methylenedioxyphenyl group, a 3,4-methylenedioxyphenyl group, a 2-thienyl group or a 3-thienyl group, is, for example, preferred.

is a group of the formula

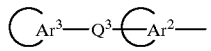

when $Q^2$ is a single bond, or a group of the formula

when $Q^2$ is $-(CH_2)_m-$ or $-(CH_2)_n-W-(CH_2)_p-$.

$Q^2$ means a single bond or a group of the formula $-(CH_2)_m-$ or $-(CH_2)_n-W-(CH_2)_p-$, but a single bond is preferred.

m means an integer of from 1 to 6, but from 1 to 4 is preferred.

n and p are the same or different and mean an integer of from 0 to 3, but they are preferably the same or different and 0 or 1.

W means an oxygen atom, a sulfur atom, a vinylene group or an ethynylene group, but a vinylene group or an ethynylene group, particularly a vinylene group, is preferred.

Each of

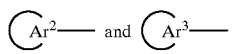

which are the same or different, means an aryl group or a heteroaromatic ring group which may have substituent(s) selected from the group consisting of a halogen atom, a hydroxyl group, an amino group, a nitro group, a cyano group, a carboxyl group, a lower alkoxycarbonyl group, a lower alkylamino group, a carbamoyl group, a lower alkylcarbamoyl group, a lower alkyl group, a lower alkenyl group, a lower hydroxyalkyl group, a lower fluoroalkyl group, a lower alkoxy group and an aralkyloxy group.

The aryl group or the heteroaromatic ring group which may have substituent(s) selected from the group consisting of a halogen atom, a hydroxyl group, an amino group, a nitro group, a cyano group, a carboxyl group, a lower alkoxycarbonyl group, a lower alkylamino group, a carbamoyl group, a lower alkylcarbamoyl group, a lower alkyl group, a lower alkenyl group, a lower hydroxyalkyl group, a lower fluoroalkyl group, a lower alkoxy group and an aralkyloxy group, means the above-mentioned aryl group or the above-mentioned heteroaromatic ring which is unsubstituted or the above-mentioned aryl group or the above-mentioned heteroaromatic ring group which has substituent(s) at optional position(s) for substitution, and said substituent(s) may be one or more, preferably one or two, which are the same or different and which are selected from the group consisting of a halogen atom, a hydroxyl group, an amino group, a nitro group, a cyano group, a carboxyl group, a lower alkoxycarbonyl group, a lower alkylamino group, a carbamoyl group, a lower alkylcarbamoyl group, a lower alkyl group, a lower alkenyl group, a lower hydroxyalkyl group, a lower fluoroalkyl group, a lower alkoxy group and an aralkyloxy group.

As the substituent of

preferred is a halogen atom such as a fluorine atom or a chlorine atom, a hydroxyl group, a lower alkyl group such as a methyl group or an ethyl group, a lower alkenyl group such as a vinyl group, a 1-propenyl group or a 2-propenyl group, an alkoxyl group such as a methoxy group, an ethoxy group or a propoxy group, or an aralkyloxy group such as a benzyloxy group, a 1-naphthylmethyloxy group or a 2-naphthylmethyloxy group.

As

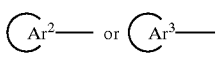

preferred is, for example, a phenyl group, a furyl group, a thienyl group or a pyridyl group, and particularly preferred is, for example, a phenyl group or a thienyl group.

Especially when $Q^2$ is a group of the formula $-(CH_2)_m-$ or $-(CH_2)_n-W-(CH_2)_p-$, preferred as

is, for example, a naphthyl group or a benzothienyl group, in addition to the above.

$Q^3$ is a single bond, an oxygen atom, a sulfur atom, a methylene group, a vinylene group, or a group of the formula $-CO-$, $-NH-$, $-COO-$, $-OCO-$, $-CH_2CH_2-$, $-OCH_2-$, $-SCH_2-$, $-CH_2O-$, $-CH_2S-$, $-NHCO-$ or $-CONH-$, but a single bond, an oxygen atom, a vinylene group or a group of the formula $-CO-$, particularly a single bond or an oxygen atom, is preferred.

Accordingly, specific examples of

include, when $Q^2$ is a single bond, a 4-(phenylthio)phenyl group, a 4-benzylphenyl group, a 3-styrylphenyl group, a 4-styrylphenyl group, a 4-benzoylphenyl group, a 4-anilinophenyl group, a 3-(benzoyloxy)phenyl group, a 3-(phenoxycarbonyl)phenyl group, a 3-phenethylphenyl group, a 3-(phenoxymethyl)phenyl group, a 3-(phenylthio)phenyl group, a 3-(benzyloxy)phenyl group, a 3-(benzylthio)phenyl group, a 3-(phenylcarbamoyl)phenyl group, a 3-(benzoylamino)phenyl group, a 2-biphenylyl group, a 3-biphenylyl group, a 2-(phenoxy)phenyl group, a 3-(phenoxy)phenyl group, a 6-phenyl-3-pyridyl group, a 5-phenyl-2-pyridyl group, a 4-(2-pyridyl)phenyl group, a 4-(3-pyridyl)phenyl group, a 4-(4-pyridyl)phenyl group, a 5-phenyl-3-thienyl group, a 4-phenyl-2-thienyl group, a 4-(2-thienyl)phenyl group, a 4-(3-thienyl)phenyl group, a 5-phenyl-3-furyl group, a 4-phenyl-2-furyl group, a 4-(2-furyl)phenyl group, a 4-(3-furyl)phenyl group, a 6-phenoxy-3-pyridyl group, a 5-phenoxy-2-pyridyl group, a 4-(2-pyridyloxy)phenyl group, a 4-(3-pyridyloxy)phenyl group, a 4-(4-pyridyloxy)phenyl group, a 5-phenoxy-2-thienyl group, a 4-phenoxy-2-thienyl group, a 4-(2-thienyloxy) phenyl group, a 4-(3-thienyloxy)phenyl group, a 5-phenoxy-2-furyl group, a 4-phenoxy-2-furyl group, a 4-(2-furyloxy) phenyl group, a 4-(3-furyloxy)phenyl group, and groups of the formulae

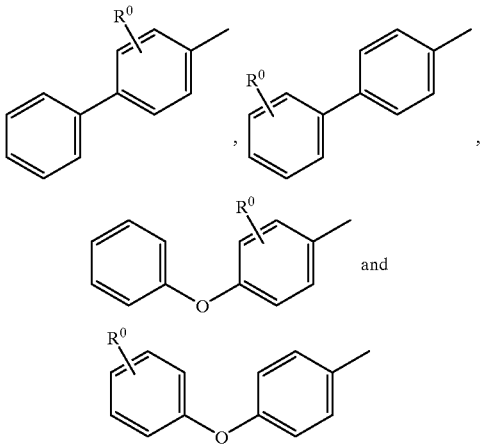

wherein $R^0$ means a hydrogen atom, a fluorine atom, a chlorine atom, a methyl group, a methoxy group, a vinyl group, a 1-propenyl group or a benzyloxy group, particularly preferred among them being, for example, the groups of the formulae

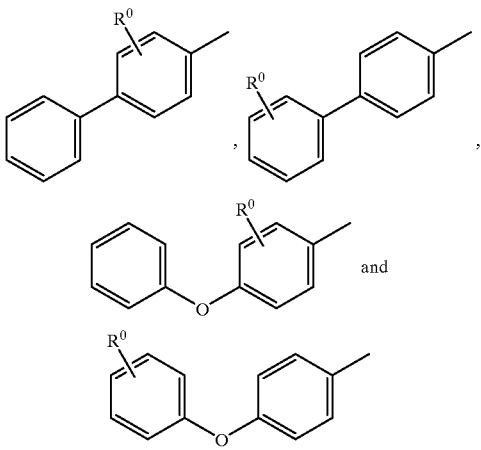

wherein $R^0$ has the above-mentioned meaning, and when $Q^2$ is a group of the formula —$(CH_2)_m$— or —$(CH_2)_n$—W—$(CH_2)_p$—, a 1-naphthyl group, a 2-naphthyl group, a 2,3-methylenedioxyphenyl group, a 3,4-methylenedioxyphenyl group, a 2,3-dichlorophenyl group, a 2,4-dichlorophenyl group, a 3,4-dichlorophenyl group, a 2-benzothienyl group and a 3-benzothienyl group, preferred among them being, for example, a 2-naphthyl group.

means an aryl group, a heteroaromatic ring group or an aliphatic ring group which may contain one or two oxygen atoms, which may have substituent(s) selected from the group consisting of a halogen atom, a hydroxyl group, an oxo group, an amino group, a nitro group, a cyano group, a carboxyl group, a carbamoyl group, a lower alkylcarbamoyl group, a lower carbamoyloxyalkyl group, a lower alkylcarbamoyloxyalkyl group, a lower alkyl group, a lower fluoroalkyl group, a lower hydroxyalkyl group, a lower alkoxy group, a lower alkoxyalkyl group, a sulfo group, a lower alkoxysulfonyl group, a sulfamoyl group, a lower alkylsulfamoyl group, an aryl group, a heteroaromatic ring group and a group of the formula —$PO(OR^4)(OR^5)$.

The aryl group, the heteroaromatic ring group or the aliphatic ring group which may contain one or two oxygen atoms, which may have substituent(s) selected from the group consisting of a halogen atom, a hydroxyl group, an oxo group, an amino group, a nitro group, a cyano group, a carboxyl group, a carbamoyl group, a lower alkylcarbamoyl group, a lower carbamoyloxyalkyl group, a lower alkylcarbamoyloxyalkyl group, a lower alkyl group, a lower fluoroalkyl group, a lower hydroxyalkyl group, a lower alkoxy group, a lower alkoxyalkyl group, a sulfo group, a lower alkoxysulfonyl group, a sulfamoyl group, a lower alkylsulfamoyl group, an aryl group, a heteroaromatic ring group and a group of the formula —$PO(OR^4)(OR^5)$, means the above-mentioned aryl group, the above-mentioned heteroaromatic ring or the above-mentioned aliphatic ring group which may contain one or two oxygen atoms, which is unsubstituted, or the above-mentioned aryl group, the above-mentioned heteroaromatic ring group or the above-mentioned aliphatic ring group which may contain one or two oxygen atoms, which has substituent(s) at optional position(s) for substitution, and said substituent(s) may be one or more, preferably one or two, which are the same or different, and which are selected from the group consisting of a halogen atom, a hydroxyl group, an oxo group, an amino group, a nitro group, a cyano group, a carboxyl group, a carbamoyl group, a lower alkylcarbamoyl group, a lower carbamoyloxyalkyl group, a lower alkylcarbamoyloxyalkyl group, a lower alkyl group, a lower fluoroalkyl group, a lower hydroxyalkyl group, a lower alkoxy group, a lower alkoxyalkyl group, a sulfo group, a lower alkoxysulfonyl group, a sulfamoyl group, a lower alkylsulfamoyl group, an aryl group, a heteroaromatic ring group and a group of the formula —$PO(OR^4)(OR^5)$.

$R^4$ and $R^5$ are the same or different and mean a hydrogen atom or a lower alkyl group, but a hydrogen atom, a methyl group or an ethyl group is, for example, preferred.

As the substituent of

preferred is, for example, a carboxyl group, a carbamoyl group, a lower alkylcarbamoyl group such as a methylcarbamoyl group, an ethylcarbamoyl group or a dimethylcarbamoyl group, a lower carbamoyloxyalkyl group such as a carbamoyloxymethyl group, a lower alkylcarbamoyloxyalkyl group such as a methylcarbamoyloxymethyl group, an ethylcarbamoyloxymethyl group or a dimethylcarbamoyloxymethyl group, a lower alkyl group such as a methyl group, an ethyl group or a propyl group, a lower hydroxyalkyl group such as a hydroxymethyl group, a lower alkoxy group such as a methoxy group or an ethoxy group, a lower alkoxyalkyl group such as a methoxymethyl group, a sulfo group, or a group of the formula —$PO(OR^4)(OR^5)$, wherein $R^4$ and $R^5$ have the above-mentioned meanings. As

preferred is, for example, a cyclobutyl group, a cyclopentyl group, an oxolanyl group, a 1,3-dioxolanyl group, a phenyl group or a pyridyl group, and particularly preferred among them is a 1,3-dioxolanyl group.

The group of the formula

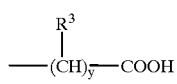

can be substituted at any optional position for substitution on the group of the formula

$R^3$ means a hydrogen atom, a hydroxyl group or a lower alkyl group, but a hydrogen atom or a hydroxyl group is, for example, preferred.

y is 0 or 1, preferably 0.

The group of the formula

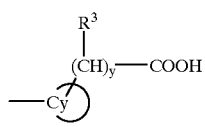

may, for example, be a group of the formula

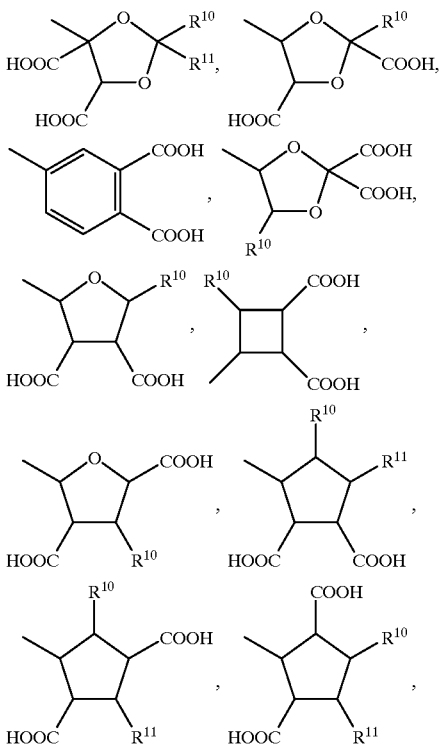

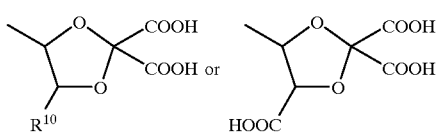

wherein each of $R^{10}$ and $R^{11}$ which are the same or different, is a hydrogen atom, a carbamoyl group, a lower alkylcarbamoyl group, a lower carbamoyloxyalkyl group, a lower alkylcarbamoyloxyalkyl group, a lower alkyl group, a lower hydroxyalkyl group, a lower alkoxy group, a lower alkoxyalkyl group or a group of the formula —PO(OR$^4$)(OR$^5$), wherein $R^4$ and $R^5$ have the above-mentioned meanings, and among them, particularly preferred is a group of the formula wherein $R^{10}$ has the above-mentioned meaning.

As $R^{10}$ and $R^{10}$, preferred is, for example, a hydrogen atom, a carbamoyl group, a lower alkylcarbamoyl group such as a methylcarbamoyl group, an ethylcarbamoyl group or a dimethylcarbamoyl group, a lower carbamoyloxyalkyl group such as a carbamoyloxymethyl group, a lower alkylcarbamoyloxyalkyl group such as a methylcarbamoyloxymethyl group, an ethylcarbamoyloxymethyl group or a dimethylcarbamoyloxymethyl group, a lower alkyl group such as a methyl group or an ethyl group, a lower hydroxyalkyl group such as a hydroxymethyl group, or a lower alkoxyalkyl group such as a methoxymethyl group.

$Q^1$ means a single bond, a group of the formula —CH$_2$O—, —OCH$_2$—, —CH$_2$S— or —SCH$_2$—, or a C$_{1-6}$ chain hydrocarbon group which may have substituent(s) selected from the group consisting of a halogen atom and a lower alkyl group, but preferred is a C$_{1-6}$ preferably C$_{1-4}$, chain hydrocarbon group which may have substituent(s) selected from the group consisting of a halogen atom and a lower alkyl group.

The C$_{1-6}$ chain hydrocarbon group which may have substituent(s) selected from the group consisting of a halogen atom and a lower alkyl group, means the above-mentioned chain hydrocarbon group having from 1 to 6 carbon atoms, which is unsubstituted, or the above-mentioned chain hydrocarbon group having from 1 to 6 carbon atoms, which has substituent(s) at optional position (s) for substitution, and said substituent(s) may be one or more, preferably from one to three, which are the same or different and which are selected from the group consisting of a halogen atom and a lower alkyl group.

As $Q^1$, preferred is, for example, a methylene group, an ethylene group or a propenylene group, and particularly preferred among them is, for example, a methylene group or an ethylene group.

$A^1$ means a C$_{1-4}$ chain hydrocarbon group which may have substituent(s) selected from the group consisting of a halogen atom, a lower alkyl group, a hydroxyl group, a lower hydroxyalkyl group and a lower alkoxy group.

The C$_{1-4}$ chain hydrocarbon group which may have substituent(s) selected from the group consisting of a halogen atom, a lower alkyl group, a hydroxyl group, a lower hydroxyalkyl group and a lower alkoxy group, means the above-mentioned chain hydrocarbon group having from 1 to 4 carbon atoms, which is unsubstituted, or the above-mentioned chain hydrocarbon group having from 1 to 4 carbon atoms, which has substituent(s) at optional position(s) for substitution, and the substituent(s) may be one or more, preferably from one to three, which are the same or different and which are selected from the group consisting of a halogen atom, a lower alkyl group, a hydroxyl group, a lower hydroxyalkyl group and a lower alkoxy group.

As $A^1$, preferred is, for example, a methylene group, an ethylene group or a trimethylene group, and particularly preferred is, for example, a methylene group or an ethylene group.

$R^1$ means a lower alkyl group, but preferred is, for example, a methyl group, an ethyl group or a propyl group, and particularly preferred is a methyl group or an ethyl group.

$R^2$ means a hydrogen atom, a hydroxyl group or a lower alkyl group, but preferred is, for example, a hydrogen atom, a hydroxyl group or a methyl group.

x means an integer of from 0 to 2, but preferred is 0 or 1.

Accordingly, specific examples of the compound of the formula (I) include

4-[N-{2-(4-biphenylyl)-1-methyl-4-phenylbutyl}-N-(carboxymethyl)carbamoyl]-1,3-dioxolane-2,2-dicarboxylic acid, 4-[N-(carboxymethyl)-N-{1-methyl-4-phenyl-2-(3-styrylphenyl)butyl}carbamoyl]-1,3-dioxolane-2,2-dicarboxylic acid, 4-[N-(carboxymethyl)-N-{1-methyl-2-(3-phenoxymethylphenyl)-4-phenylbutyl}carbamoyl]-1,3-dioxolane-2,2-dicarboxylic acid, 4-[N-{2-(4-benzoylphenyl)-1-methyl-4-phenylbutyl}-N-(carboxymethyl)carbamoyl]-1,3-dioxolane-2,2-dicarboxylic acid, 4-[N-(carboxymethyl)-N-{2-(2-hydroxy-4-biphenylyl)-1-methyl-4-phenylbutyl}carbamoyl]-1,3-dioxolane-2,2-dicarboxylic acid, 4-[N-(carboxymethyl)-N-{2-(2-methoxy-4-biphenylyl)-1-methyl-4-phenylbutyl}carbamoyl]-1,3-dioxolane-2,2-dicarboxylic acid, 4-[N-(carboxymethyl)-N-{1-methyl-4-phenyl-2-(2-vinyl-4-biphenylyl)butyl}carbamoyl]-1,3-dioxolane-2,2-dicarboxylic acid, 4-[N-(carboxymethyl)-N-[1-methyl-4-phenyl-2-{2-(1-propenyl)-4-biphenylyl}butyl]carbamoyl]-1,3-dioxolane-2,2-dicarboxylic acid, 4-[N-{2-(2-benzyloxy-4-biphenylyl)-1-methyl-4-phenylbutyl}-N-(carboxymethyl)carbamoyl]-1,3-dioxolane-2,2-dicarboxylic acid, 4-[N-(carboxymethyl)-N-{1-methyl-4-phenyl-2-(5-phenyl-2-thienyl)butyl}carbamoyl]-1,3-dioxolane-2,2-dicarboxylic acid, 4-[N-(carboxymethyl)-N-{1-methyl-4-phenyl-2-(5-phenyl-3-thienyl)butyl}carbamoyl]-1,3-dioxolane-2,2-dicarboxylic acid, 4-[N-(carboxymethyl)-N-{1-methyl-4-phenyl-2-(4-phenyl-2-thienyl)butyl}carbamoyl]-1,3-dioxolane-2,2-dicarboxylic acid, 4-[N-(carboxymethyl)-N-[1-methyl-4-phenyl-2-{4-(2-thienyl)phenyl}butyl]carbamoyl]-1,3-dioxolane-2,2-dicarboxylic acid, 4-[N-(carboxymethyl)-N-[1-methyl-4-phenyl-2-{4-(3-thienyl)phenyl}butyl]carbamoyl]-1,3-dioxolane-2,2-dicarboxylic acid, 4-[N-(carboxymethyl)-N-{1-methyl-4-phenyl-2-(5-phenyl-2-pyridyl)butyl}carbamoyl]-1,3-dioxolane-2,2-dicarboxylic acid, 4-[N-(carboxymethyl)-N-{1-methyl-4-phenyl-2-(6-phenyl-3-pyridyl)butyl}carbamoyl]-1,3-dioxolane-2,2-dicarboxylic acid, 4-[N-(carboxymethyl)-N-[1-methyl-4-phenyl-2-{4-(2-pyridyl)phenyl}butyl]carbamoyl]-1,3-dioxolane-2,2-dicarboxylic acid, 4-[N-(carboxymethyl)-N-[1-methyl-4-phenyl-2-{4-(3-pyridyl)phenyl}butyl]carbamoyl]-1,3-dioxolane-2,2-dicarboxylic acid, 4-[N-(carboxymethyl)-N-[1-methyl-4-phenyl-2-{4-(4-pyridyl)phenyl}butyl]carbamoyl]-1,3-dioxolane-2,2-dicarboxylic acid, 4-[N-(carboxymethyl)-N-{1-methyl-2-(3-methyl-4-phenoxyphenyl)-4-phenylbutyl}carbamoyl]-1,3-dioxolane-2,2-dicarboxylic acid, 4-[N-(carboxymethyl)-N-{1-methyl-2-(4-phenoxy-3-vinylphenyl)-4-phenylbutyl}carbamoyl]-1,3-dioxolane-2,2-dicarboxylic acid, 4-[N-{2-(3-benzyloxy-4-phenoxyphenyl)-1-methyl-4-phenylbutyl}-N-(carboxymethyl)carbamoyl]-1,3-dioxolane-2,2-dicarboxylic acid, 4-[N-(carboxymethyl)-N-{1-methyl-2-(5-phenoxy-2-pyridyl)-4-phenylbutyl}carbamoyl]-1,3-dioxolane-2,2-dicarboxylic acid, 4-[N-(carboxymethyl)-N-{1-methyl-2-(6-phenoxy-3-pyridyl)-4-phenylbutyl}carbamoyl]-1,3-dioxolane-2,2-dicarboxylic acid, 4-[N-(carboxymethyl)-N-[1-methyl-4-phenyl-2-{4-(2-pyridyloxy)phenyl}butyl]carbamoyl]-1,3-dioxolane-2,2-dicarboxylic acid, 4-[N-(carboxymethyl)-N-[1-methyl-4-phenyl-2-{4-(3-pyridyloxy)phenyl}butyl]carbamoyl]-1,3-dioxolane-2,2-dicarboxylic acid, 4-[N-(carboxymethyl)-N-[1-methyl-4-phenyl-2-{4-(4-pyridyloxy)phenyl}butyl]carbamoyl]-1,3-dioxolane-2,2-dicarboxylic acid, 4-[N-(carboxymethyl)-N-{1-methyl-2-(2-methyl-4-phenoxyphenyl)-4-phenylbutyl}carbamoyl]-1,3-dioxolane-2,2-dicarboxylic acid, 4-[N-(carboxymethyl)-N-[2-{4-(2-fluorophenoxy)phenyl}-1-methyl-4-phenylbutyl]carbamoyl]-1,3-dioxolane-2,2-dicarboxylic acid, 4-[N-(carboxymethyl)-N-[2-{4-(3-methoxyphenoxy)phenyl}-1-methyl-4-phenylbutyl]carbamoyl]-1,3-dioxolane-2,2-dicarboxylic acid, 4-[N-[2-{4-(4-bromophenoxy)phenyl}-1-methyl-4-phenylbutyl]-N-(carboxymethyl)carbamoyl]-1,3-dioxolane-2,2-dicarboxylic acid, 4-[N-(carboxymethyl)-N-[1-methyl-4-phenyl-2-[4-{3-(1-propenyl)phenoxy}phenyl]butyl]carbamoyl]-1,3-dioxolane-2,2-dicarboxylic acid, 4-[N-(carboxymethyl)-N-{1-methyl-3-(2-naphthyl)-2-(4-phenoxyphenyl)propyl}carbamoyl]-1,3-dioxolane-2,2-dicarboxylic acid, 4-[N-(carboxymethyl)-N-{1-methyl-3-(1-naphthyl)-2-(4-phenoxyphenyl)propyl}carbamoyl]-1,3-dioxolane-2,2-dicarboxylic acid, 4-[N-(carboxymethyl)-N-{1-methyl-3-(2,3-methylenedioxyphenyl)-2-(4-phenoxyphenyl)propyl}carbamoyl]-1,3-dioxolane-2,2-dicarboxylic acid, 4-[N-(carboxymethyl)-N-{1-methyl-2-(4-phenoxyphenyl)-4-(2-thienyl)butyl}carbamoyl]-1,3-dioxolane-2,2-dicarboxylic acid, 4-[N-(carboxymethyl)-N-{1-methyl-2-(4-phenoxyphenyl)-3-(2-quinolyl)propyl}carbamoyl]-1,3-dioxolane-2,2-dicarboxylic acid, 4-[N-(carboxymethyl)-N-{1-methyl-4-(2,3-methylenedioxyphenyl)-2-(4-phenoxyphenyl)butyl)carbamoyl]-1,3-dioxolane-2,2-dicarboxylic acid, 4-[N-(carboxymethyl)-N-{4-(4-fluorophenyl)-1-methyl-2-(4-phenoxyphenyl)butyl}carbamoyl]-1,3-dioxolane-2,2-dicarboxylic acid, 4-{N-(carboxymethyl)-N-{(1-methyl-2-phenethyl-4-phenyl-3-butenyl}carbamoyl]-1,3-dioxolane-2,2-dicarboxylic acid, 4-[N-(carboxymethyl)-N-{1-methyl-4-(2-naphthyl)-2-phenethyl-3-butenyl}carbamoyl]-1,3-dioxolane-2,2-dicarboxylic acid, 4-[N-{4-(2-benzo[b]thienyl)-1-methyl-2-phenethyl-3-butenyl}-N-(carboxymethyl)carbamoyl]-1,3-dioxolane-2,2-dicarboxylic acid, 4-[N-(carboxymethyl)-N-{4-(3,4-dichlorophenyl)-1-methyl-2-phenethyl-3-butenyl}carbamoyl]-1,3-dioxolane-2,2-dicarboxylic acid, 4-[N-(carboxymethyl)-N-{1-ethyl-2-(4-phenoxyphenyl)-4-phenylbutyl}carbamoyl]-1,3-dioxolane-2,2-dicarboxylic acid, 4-[N-(carboxyethyl)-N-{1-methyl-2-(4-phenoxyphenyl)-4-phenylbutyl}carbamoyl]-1,3-dioxolane-2,2-dicarboxylic acid, 4-[N-(carboxymethyl)-N-{1-methyl-2-(4-phenoxyphenyl)-4-phenylbutyl}carbamoyl]-5-hydroxymethyl-1,3-dioxolane-2,2-dicarboxylic acid, 4-[N-(carboxymethyl)-N-{1-methyl-2-(4-phenoxyphenyl)-4-phenylbutyl)carbamoyl]-5-methoxymethyl-1,3-dioxolane-2,2-dicarboxylic acid, 4-[N-(carboxymethyl)-N-{1-methyl-2-(4-phenoxyphenyl)-4-phenylbutyl}carbamoyl]-5-carbamoyloxymethyl-1,3-dioxolane-2,2-dicarboxylic acid, 4-[N-(carboxymethyl)-N-{1-methyl-2-(4-phenoxyphenyl)-4-phenylbutyl}carbamoyl]-5-methylcarbamoyloxymethyl-1,3-dioxolane-2,2-dicarboxylic acid, 4-[N-(carboxymethyl)-N-{1-methyl-2-(4-phenoxyphenyl)-4-phenylbutyl}carbamoyl]-5-dimethylcarbamoyloxymethyl-1,3-dioxolane-2,2-dicarboxylic acid, 4-[N-(carboxymethyl)-N-{1-methyl-2-(4-phenoxyphenyl)-4-phenylbutyl}carbamoyl]-5-carbamoyl-1,3-dioxolane-2,2-dicarboxylic acid, 4-[N-(carboxymethyl)-N-{1-methyl-2-(4-phenoxyphenyl)-4-phenylbutyl}carbamoyl]-5-methylcarbamoyl-1,3-dioxolane-2,2-dicarboxylic acid, 3-[N-(carboxymethyl)-N-{1-methyl-2-(4-phenoxyphenyl)-4-phenylbutyl}carbamoyl]cyclobutane-1,2-dicarboxylic acid, 3-[N-(carboxymethyl)-N-1-methyl-2-(4-phenoxyphenyl)-4-phenylbutyl}carbamoyl]cyclobutane-1,1-dicarboxylic acid, 3-[N-(carboxymethyl)-N-{1-methyl-2-(4-phenoxyphenyl)-4-phenylbutyl)carbamoyl]cyclopentane-1,1-dicarboxylic acid, 5-[N-(carboxymethyl)-N-{1-methyl-2-(4-phenoxyphenyl)-4-phenylbutyl}carbamoyl]oxolane-3,3-dicarboxylic acid, 4-[N-(carboxymethyl)-N-{1-methyl-2-(4-phenoxyphenyl)-4-phenylbutyl}carbamoyl]-2-phosphono-1,3-dioxolane-2-dicarboxylic acid, 4-[N-(carboxymethyl)-N-{1-methyl-2-(4-phenoxyphenyl)-4-phenylbutyl}carbamoylmethyl]-1,3-dioxolane-2,2-dicarboxylic acid, 4-[N-(carboxymethyl)-N-{1-methyl-2-(4-phenoxyphenyl)-4-phenylbutyl}carbamoylhydroxymethyl]-1,3-dioxolane-2,2-dicarboxylic acid, 4-[N-(carboxymethyl)-N-{1-methyl-2-(4-phenoxyphenyl)-4-phenylbutyl}carbamoyl]phthalic acid, 4-[N-(carboxymethyl)-N-{1-methyl-2-(4-phenoxyphenyl)-4-phenylbutyl}carbamoylmethyl]phthalic acid, 5-[N-(carboxymethyl)-N-{1-methyl-2-(4-phenoxyphenyl)-4-phenylbutyl}carbamoylmethyl]pyridine-2,3-dicarboxylic acid, 4-[N-(carboxymethyl)-N-{1-methyl-2-(4-phenoxyphenyl)-4-phenylbutyl}carbamoyl]-2-methyl-1,3-dioxolane-2-carboxylic acid, 4-[N-(carboxymethyl)-N-{1-methyl-2-(4-phenoxyphenyl)-4-phenylbutyl}carbamoyl]-1,3-dioxolane-2-carboxylic acid, 4-[N-(carboxymethyl)-N-{1-methyl-2-(4-phenoxyphenyl)-4-phenylbutyl}carbamoyl]cyclopentane-1,2-dicarboxylic acid, 4-[N-(carboxymethyl)-N-{2-(2-fluoro-4-biphenylyl)-1-methyl-4-phenylbutyl}carbamoyl]-1,3-dioxolane-2,2,5-tricarboxylic acid, 4-[N-(carboxymethyl)-N-{2-(3-hydroxy-4-phenoxyphenyl)-1-methyl-4-phenylbutyl}carbamoyl]-1,3-dioxolane-2,2,5-tricarboxylic acid, 4-[N-(carboxymethyl)-N-{2-(3-methoxy-4-phenoxyphenyl)-1-methyl-4-phenylbutyl}carbamoyl]-1,3-dioxolane-2,2,5-tricarboxylic acid, 4-[N-(carboxymethyl)-N-{2-(3-fluoro-4-phenoxyphenyl)-1-methyl-4-phenylbutyl}carbamoyl]-1,3-dioxolane-2,2,5-tricarboxylic acid, 4-[N-(carboxymethyl)-N-{1-methyl-2-(4-phenoxyphenyl)-4-phenylbutyl}carbamoyl]-1,3-dioxolane-2,2-dicarboxylic acid 2,2-isopropylidene ester, 4-[N-(carboxymethyl)-N-{1-methyl-2-(4-phenoxyphenyl)-4-phenylbutyl)carbamoyl]-1,3-dioxolane-2,2-dicarboxylic acid 2,2-bis(2-methoxyethyl)ester, 4-[N-(carboxymethyl)-N-{1-methyl-2-(4-phenoxyphenyl)-4-phenylbutyl)carbamoyl]-1,3-dioxolane-2,2-dicarboxylic acid 2,2-bis(2-ethoxycarbonylmethyl)ester, 4-[N-(carboxymethyl)-N-{1-methyl-4-(2-naphthyl)-2-phenethyl-3-butenyl}carbamoyl]-1,3-dioxolane-2,2,5-tricarboxylic acid, 4-[N-(carboxymethyl)-N-[1-methyl-2-{4-(3,4-methylenedioxyphenoxy)phenyl)-4-phenylbutyl]carbamoyl]-1,3-dioxolane-2,2,5-tricarboxylic acid, 4-[N-(carboxymethyl)-N-{1-methyl-3-(2-naphthyl)-2-(4-phenoxyphenyl)propyl}carbamoyl]-1,3-dioxolane-2,2,5-tricarboxylic acid, 4-[N-(carboxymethyl)-N-{1-methyl-3-(1-naphthyl)-2-(4-phenoxyphenyl)propyl)carbamoyl]-1,3-dioxolane-2,2,5-tricarboxylic acid, 4-[N-(carboxymethyl)-N-{1-methyl-3-(3,4-methylenedioxyphenyl)-2-(4-phenoxyphenyl)propyl}carbamoyl]-1,3-dioxolane-2,2,5-tricarboxylic acid, 4-[N-(carboxymethyl)-N-{1-methyl-2-(4-phenoxyphenyl)-4-phenylbutyl}carbamoyl]cyclohexane-1,1-dicarboxylic acid, 4-[N-(carboxymethyl)-N-{1-methyl-2-(4-phenoxyphenyl)-4-phenylbutyl)carbamoyl]-2-sulfo-1,3-dioxolane-2-carboxylic acid, 4-[N-(carboxymethyl)-N-{2-(3-fluoro-4-biphenylyl)-1-methyl-4-phenylbutyl}carbamoyl]-1,3-dioxolane-2,2-dicarboxylic acid, 4-[N-(carboxymethyl)-N-{2-(2'-methoxy-4-biphenylyl)-1-methyl-4-phenylbutyl}carbamoyl]-1,3-dioxolane-2,2,5-tricarboxylic acid, 4-[N-(carboxymethyl)-N-[1-methyl-4-phenyl-2-{3'-(1-propenyl)-4-biphenylyl}butyl]carbamoyl]-1,3-dioxolane-2,2-dicarboxylic acid, 4-[N-(carboxymethyl)-N-{2-(4'-chloro-4-biphenylyl)-1-methyl-4-phenylbutyl}carbamoyl]-1,3-dioxolane-2,2,5-tricarboxylic acid, 4-[N-(carboxymethyl)-N-{1-methyl-4-phenyl-2-(4-phenylthiophenyl)butyl)carbamoyl]-1,3-dioxolane-2,2,5-tricarboxylic acid, 4-[N-(carboxymethyl)-N-{1-methyl-4-phenyl-2-(4-phenylaminophenyl)butyl}carbamoyl]-1,3-dioxolane-2,2,5-tricarboxylic acid, 4-[N-(carboxymethyl)-N-[1-methyl-4-phenyl-2-[4-{3-(2-propenyl)phenoxy}phenyl]butyl]carbamoyl]-1,3-dioxolane-2,2,5-tricarboxylic acid, 4-[N-(carboxymethyl)-N-{1-methyl-4-phenyl-2-(5-phenyl-2-furyl)butyl}carbamoyl]- 1,3-dioxolane-2,2-dicarboxylic acid, 4-[N-(carboxymethyl)-N-{1-methyl-2-(4-phenoxyphenyl)-4-phenyl-3-butenyl}carbamoyl]-1,3-dioxolane-2,2,5-tricarboxylic acid, 4-[N-(carboxymethyl)-N-{1-methyl-2-(4-phenoxyphenyl)-5-phenyl-4-pentenyl)carbamoyl]-1,3-dioxolane-2,2,5-tricarboxylic acid, 4-[N-{2-(3-benzyloxyphenyl)-1-methyl-4-phenylbutyl)-N-(carboxymethyl)carbamoyl]-1,3-dioxolane-2,2-dicarboxylic acid, 4-[N-(carboxymethyl)-N-{1-methyl-2-(4-phenoxyphenyl)-4-phenylbutyl}carbamoyl]-5-methylsulfamoyl-1,3-dioxolane-2,2-dicarboxylic acid, 2-[N-(carboxymethyl)-N-{1-methyl-2-(4-phenoxyphenyl)-4-phenylbutyl}carbamoyl]-1,3-dioxolane-2,4,5-tricarboxylic acid, 5-[N-(carboxymethyl)-N-{1-methyl-2-(4-phenoxyphenyl)-4-phenylbutyl)carbamoyl]oxolane-2,3,4-tricarboxylic acid, 4-[N-(carboxymethyl)-N-{1-methyl-2-(4-phenoxyphenyl)-4-phenylbutyl}carbamoyl]-5-aminomethyl-1,3-dioxolane-2,2-dicarboxylic acid, 2-[N-(carboxymethyl)-N-{2-(2-fluoro-4-biphenylyl)-1-methyl-4-phenylbutyl)carbamoyl]cyclopropane-1,1-dicarboxylic acid, 4-[N-(carboxymethyl)-N-{2-(2-fluoro-4-biphenylyl)-1-methyl-4-phenylbutyl}carbamoylmethyl]phthalic acid, 4-[N-(carboxymethyl)-N-{2-(2-fluoro-4-biphenylyl)-1-methyl-4-phenylbutyl}carbamoyl]phthalic acid, 5-[N-(carboxymethyl)-N-{2-(2-fluoro-4-biphenylyl)-1-methyl-4-phenylbutyl}carbamoyl]isophthalic acid, 4-[N-(carboxymethyl)-N-{2-(2-fluoro-4-biphenylyl)-1-methyl-4-phenylbutyl}carbamoylmethyl]-2,2-dimethyl-1,3-dioxolane-4,5-dicarboxylic acid, disodium 5-[N-(carboxylatomethyl)-N-{2-(2-fluoro-4-biphenylyl)-1-methyl-4-phenylbutyl}carbamoyl]-2-ethoxy-1,3-dioxolane-4-carboxylate, 4-[N-(carboxymethyl)-N-{1-methyl-2-(4-phenoxyphenyl)-4-phenylbutyl}carbamoylmethyl]-2,2-dimethyl-1,3-dioxolane-4,5-dicarboxylic acid, trisodium 4-[N-(carboxylatomethyl)-N-{1-methyl-2-(4-phenoxyphenyl)-4-phenylbutyl}carbamoylhydroxymethyl]-2,2-dimethyl-1,3-dioxolane-4,5-dicarboxylate, 4-[N-(carboxymethyl)-N-{1-methyl-2-(4-phenoxyphenyl)-4-phenylbutyl}carbamoyl]-1,3-dioxolane-2,2-dicarboxylic acid, 4-[N-(carboxymethyl)-N-{1-methyl-2-(4-phenoxyphenyl)-4-phenylbutyl}carbamoyl]-5-methyl-1,3-dioxolane-2,2-dicarboxylic acid, 4-[N-(carboxymethyl)-N-{1-methyl-2-(4-phenoxyphenyl)-4-phenylbutyl}carbamoyl]-5-ethyl-1,3-dioxolane-2,2-dicarboxylic acid, 2-[N-(carboxymethyl)-N-{1-methyl-2-(4-phenoxyphenyl)-4-phenylbutyl}carbamoyl]-1,3-dioxolane-2,4-dicarboxylic acid, 4-[N-(carboxymethyl)-N-{1-methyl-2-(4-phenoxyphenyl)-4-phenylbutyl}carbamoyl]-1,3-dioxolane-2,2,5-tricarboxylic acid 2-ethyl ester, 4-[N-(carboxymethyl)-N-{1-methyl-2-(4-phenoxyphenyl)-4-phenylbutyl}carbamoyl]-1,3-dioxolane-2,2,5-tricarboxylic acid, 4-[N-(carboxymethyl)-N-{1-methyl-2-(4-phenoxyphenyl)-4-phenylbutyl}carbamoyl]-1,3-dioxolane-2,2,5-tricarboxylic acid 5-tert-butyl ester, 4-[N-(carboxymethyl)-N-{1-methyl-2-(4-phenoxyphenyl)-4-phenylbutyl}carbamoyl]-5-(N-ethylcarbamoyl)-1,3-dioxolane-2,2-dicarboxylic acid, 5-carbamoyl-4-[N-(carboxymethyl)-N-{1-methyl-2-(4-phenoxyphenyl)-4-phenylbutyl}carbamoyl]-1,3-dioxolane-2,2-dicarboxylic acid, 4-[N-(carboxymethyl)-N-{1-methyl-2-(4-phenoxyphenyl)-4-phenylbutyl}carbamoyl]-5-(hydroxymethyl)-1,3-dioxolane-2,2-dicarboxylic acid, 4-[N-(carboxymethyl)-N-{1-methyl-2-(4-phenoxyphenyl)-4-phenylbutyl}carbamoyl]-2-(N-ethylcarbamoyl)-1,3-dioxolane-2,5-dicarboxylic acid, 4-[N-(carboxymethyl)-N-{1-methyl-2-(4-phenoxyphenyl)-4-phenylbutyl}carbamoyl]-2-(N,N-dimethylcarbamoyl)-1,3-dioxolane-2,5-dicarboxylic acid, 4-[N-(carboxymethyl)-N-{1-methyl-2-(4-phenoxyphenyl)-4-phenylbutyl}carbamoyl]-2,2-bis(hydroxymethyl)-1,3-dioxolane-2,5-dicarboxylic acid, 4-[N-(carboxymethyl)-N-[2-(3-methoxy-4-phenoxyphenyl)-1-methyl-4-phenylbutyl}carbamoyl]-1,3

4-[N-(carboxymethyl)-N-{2-(3-hydroxy-4-phenoxyphenyl)-1-methyl-4-phenylbutyl}carbamoyl]-1,3-dioxolane-2,2-dicarboxylic acid, 4-[N-(carboxymethyl)-N-{1-methyl-2-(4-phenoxyphenyl)-4-phenylbutyl}carbamoyl]-1,3-dioxolane-2,2,5-tricarboxylic acid 2,2-diethyl ester, 4-[N-(carboxymethyl)-N-{1-methyl-2-(4-phenoxyphenyl)-4-phenylbutyl}carbamoyl]-1,3-dioxolane-2,2-dicarboxylic acid 2,2-diethyl ester, 4-[N-(carboxymethyl)-N-{1-methyl-2-(4-phenoxyphenyl)-4-phenylbutyl}carbamoyl]-1,3-dioxolane-2,2-dicarboxylic acid 2,2-bis(pivaloyloxymethyl)ester, 4-[N-{1-methyl-2-(4-phenoxyphenyl)-4-phenylbutyl}-N-(pivaloyloxymethoxycarbonylmethyl)carbamoyl]-1,3-dioxolane-2,2-dicarboxylic acid 2-pivaloyloxymethyl ester, 4-[N-{1-methyl-2-(4-phenoxyphenyl)-4-phenylbutyl}-N-(pivaloyloxymethoxycarbonylmethyl)carbamoyl]-1,3-dioxolane-2,2-dicarboxylic acid 2-methyl ester, 4-[N-(carboxymethyl)-N-{1-methyl-2-(4-phenoxyphenyl)-4-phenylbutyl}carbamoyl]-1,3-dioxolane-2,2-dicarboxylic acid 2-methyl ester, 4-[N-(carboxymethyl)-N-{2-(2-fluoro-4-biphenylyl)-1-methyl-4-phenylbutyl}carbamoyl]-1,3-dioxolane-2,2-dicarboxylic acid, 4-[N-(carboxymethyl)-N-{1-methyl-2-(4-phenoxyphenyl)-4-(3-thienyl)butyl}carbamoyl]-1,3-dioxolane-2,2-dicarboxylic acid, 4-[N-(carboxymethyl)-N-{2-(4-phenoxyphenyl)-1-methyl-3-(3,4-methylenedioxyphenyl)propyl}carbamoyl]-1,3-dioxolane-2,2-dicarboxylic acid, 4-[N-(carboxymethyl)-N-{3-(benzo[b]thienyl)-2-(4-biphenylyl)-1-methylpropyl}carbamoyl]-1,3-dioxolane-2,2-dicarboxylic acid, and 4-[N-(carboxymethyl)-N-[2-{4-(4-bromophenoxy)phenyl}-1-methyl-4-phenylbutyl]carbamoyl]-1,3-dioxolane-2,2-dicarboxylic acid.

Among them, preferred is, for example, (2RS)-2-[N-(carboxymethyl)-N-{(1R,2R)-2-(2-fluoro-4-biphenylyl)-1-methyl-4-phenylbutyl}carbamoyl]cyclopropane-1,1-dicarboxylic acid, 4-[N-(carboxymethyl)-N-{(1R,2R)-2-(2-fluoro-4-biphenylyl)-1-methyl-4-phenylbutyl}carbamoylmethyl] phthalic acid, 4-[N-(carboxymethyl)-N-{(1R,2R)-2-(2-fluoro-4-biphenylyl)-1-methyl-4-phenylbutyl}carbamoyl]phthalic acid, 5-[N-(carboxymethyl)-N-{(1R,2R)-2-(2-fluoro-4-biphenylyl)-1-methyl-4-phenylbutyl}carbamoyl] isophthalic acid, (4R,5R)-4-[N-(carboxymethyl)-N-{(1R,2R)-2-(2-fluoro-4-biphenylyl)-1-methyl- 4-phenylbutyl}carbamoylmethyl]-2,2-dimethyl-1,3-dioxolane-4,5-dicarboxylic acid, disodium (2R*,4S,5S)-5-[N-(carboxylatomethyl)-N-{(1R,2R)-2-(2-fluoro-4-biphenylyl)-1-methyl-4-phenylbutyl}carbamoyl]-2-ethoxy-1,3-dioxolane-4-carboxylate, disodium (2S*,4S,5S)-5-[N-(carboxylatomethyl)-N-{(1R,2R)-2-(2-fluoro-4-biphenylyl)-1-methyl-4-phenylbutyl}carbamoyl]-2-ethoxy-1,3-dioxolane-4-carboxylate, (4R,5R)-4-[N-(carboxymethyl)-N-{(1R,2R)-1-methyl-2-(4-phenoxyphenyl)-4-phenylbutyl}carbamoylmethyl]-2,2-dimethyl-1,3-dioxolane-4,5-dicarboxylic acid, trisodium (4R,5R)-4-[N-(carboxylatomethyl)-N-{(1R,2R)-1-methyl-2-(4-phenoxyphenyl)-4-phenylbutyl}carbamoylhydroxymethyl]-2,2-dimethyl-1,3-dioxolane-4,5-dicarboxylate, (4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid, (4R)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid, (4S,5S)-4-[N-(carboxymethyl)-N-{(1R,2R)-1-methyl-2-(4-phenoxyphenyl)-4-phenylbutyl}carbamoyl]-5-methyl-1,3-dioxolane-2,2-dicarboxylic acid, (4R,5R)-4-(N-(carboxymethyl)-N-{(1R,2R)-1-methyl-2-(4-phenoxyphenyl)- 4-phenylbutyl}carbamoyl]-5-methyl-1,3-dioxolane-2,2-dicarboxylic acid, (4S,5R)-4-[N-(carboxymethyl)-N-{(1R,2R)-1-methyl-2-(4-phenoxyphenyl)-4-phenylbutyl}carbamoyl]-5-methyl-1,3-dioxolane-2,2-dicarboxylic acid, (4R,5S)-4-[N-(carboxymethyl)-N-{(1R,2R)-1-methyl-2-(4-phenoxyphenyl)-4-phenylbutyl}carbamoyl]-5-methyl-1,3-dioxolane-2,2-dicarboxylic acid, (4R*,5S*)-4-[N-(carboxymethyl)-N-{(1R,2R)-1-methyl-2-(4-phenoxyphenyl)-4-phenylbutyl}carbamoyl]-5-ethyl-1,3-dioxolane-2,2-dicarboxylic acid, (4S*,5R*)-4-[N-(carboxymethyl)-N-{(1R,2R)-1-methyl-2-(4-phenoxyphenyl)-4-phenylbutyl}carbamoyl]-5-ethyl-1,3-dioxolane-2,2-dicarboxylic acid, (2S*,4R)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid, (2R*,4R)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid, (2S*,4S)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid, (2R*,4S)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid, (2S*,4R,5R)-4-[N-(carboxymethyl)-N-{(1R,2R)-1-methyl-2-(4-phenoxyphenyl)- 4-phenylbutyl}carbamoyl]-1,3-dioxolane-2,2,5-tricarboxylic acid 2-ethyl ester, (2R*,4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid 2-ethyl ester, (2S*,4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid 2-ethyl ester, (2R*,4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid 2-ethyl ester, (4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid, (4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid, (4R*,5S*)-4-[N-(carboxymethyl)-N-{(1R, 2R)-1-methyl-2-(4-phenoxyphenyl)-4-phenylbutyl}carbamoyl]-1,3-dioxolane-2,2,5-tricarboxylic acid, (4S*,5R*)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid, (4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid 5-tert-butyl ester, (4S,5S)-4-[N-(carboxymethyl)-N-{(1R,2R)-1-methyl-2-(4-phenoxyphenyl)- 4-phenylbutyl}carbamoyl]-5-(N-ethylcarbamoyl)-1,3-dioxolane-2,2-dicarboxylic acid, (4S,5S)-5-carbamoyl-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid, (4S,5R)-4-[N-(carboxymethyl)-N-{(1R,2R)-1-methyl-2-(4-phenoxyphenyl)-4-phenylbutyl}carbamoyl]-5-(hydroxymethyl)-1,3-dioxolane-2,2-dicarboxylic acid, (2S*,4S,5S)-4-[N-(carboxymethyl)-N-{(1R,2R)-1-methyl-2-(4-phenoxyphenyl)-4-phenylbutyl}carbamoyl]-2-(N-ethylcarbamoyl)-1,3-dioxolane-2,5-dicarboxylic acid, (2S*,4S,5S)-4-[N-(carboxymethyl)-N-{(1R,2R)-1-methyl-2-(4-phenoxyphenyl)-4-phenylbutyl}carbamoyl]-2-(N,N-dimethylcarbamoyl)-1,3-dioxolane-2,5-dicarboxylic acid, (4S,5S)-4-[N-(carboxymethyl)-N-((1R,2R)-1-methyl-2-(4-phenoxyphenyl)-4-phenylbutyl}carbamoyl]-2,2-bis(hydroxymethyl)-1,3-dioxolane-2,5-dicarboxylic acid, (4S)-4-[N-(carboxymethyl)-N-{(1R*,2R*)-2-(3-methoxy-4-phenoxyphenyl)-1-methyl-4-phenylbutyl}carbamoyl]-1,3-dioxolane-2,2-dicarboxylic acid, (4S)-4-[N-(carboxymethyl)-N-{(1S*,2S*)-2-(3-methoxy-4-phenoxyphenyl)-1-methyl-4-phenylbutyl}carbamoyl]-1,3-dioxolane-2,2-dicarboxylic acid, (4S)-4-[N-(carboxymethyl)-N-{(1R*,2R*)-2-(3-hydroxy-4-phenoxyphenyl)-1-methyl-4-phenylbutyl}carbamoyl]-1,3-dioxolane-2,2-dicarboxylic acid, (4S)-4-[N-(carboxymethyl)-N-{(1S*,2S*)-2-(3-hydroxy-4-phenoxyphenyl)- 1-methyl-4-phenylbutyl}carbamoyl]-1,3-dioxolane-2,2-dicarboxylic acid, (4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid 2,2-diethyl ester, (4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid 2,2-diethyl ester, (4R)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid 2,2-diethyl ester, (4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid 2,2-bis(pivaloyloxymethyl)ester, (2S*,4S)-4-[N-{(1R,2R)-1-methyl-2-(4-phenoxyphenyl)-4-phenylbutyl}-N-(pivaloyloxymethoxycarbonylmethyl)carbamoyl]-1,3-dioxolane-2,2-dicarboxylic acid 2-pivaloyloxymethyl ester, (2R*,4S)-4-[N-{(1R,2R)-1-methyl-2-(4-phenoxyphenyl)-4-phenylbutyl}-N-(pivaloyloxymethoxycarbonylmethyl)carbamoyl]-1,3-dioxolane-2,2-dicarboxylic acid 2-pivaloyloxymethyl ester, (2S*,4S)-4-[N-{(1R,2R)-1-methyl-2-(4-phenoxyphenyl)-4-phenylbutyl}-N-(pivaloyloxymethoxycarbonylmethyl)carbamoyl]-1,3-dioxolane-2,2-dicarboxylic acid 2-methyl ester, (2R*,4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid 2-methyl ester, (2S*,4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid 2-methyl ester, (4S)-4-[N-(carboxymethyl)-N-{(1R,2R)-2-(2-fluoro-4-biphenylyl)-1-methyl-4-phenylbutyl}carbamoyl]-1,3-dioxolane-2,2-dicarboxylic acid, (4S)-4-[N-(carboxymethyl)-N-{(1R*,2R*)-1-methyl-2-(4-phenoxyphenyl)-4-(3-thienyl)butyl}carbamoyl]-1,3-dioxolane-2,2-dicarboxylic acid, (4S)-4-[N-(carboxymethyl)-N-[(1R*,2R*)-2-(4-phenoxyphenyl)-1-methyl-3-(3,4-methylenedioxyphenyl)propyl}carbamoyl]-1,3-dioxolane-2,2-dicarboxylic acid, (4S)-4-[N-(carboxymethyl)-N-{(1S*,2S*)-2-(4-phenoxyphenyl)-1-methyl-3-(3,4-methylenedioxyphenyl)propyl)carbamoyl]-1,3-dioxolane-2,2-dicarboxylic acid, (4S)-4-[N-(carboxymethyl)-N-{(1R*,2R*)-3-(benzo[b]thienyl)-2-(4-biphenylyl)-1-methylpropyl)carbamoyl]-1,3-dioxolane-2,2-dicarboxylic acid, (4S)-4-[N-(carboxymethyl)-N-{(1S*,2S*)-3-(benzo[b]thienyl)-2-(4-biphenylyl)-1-methylpropyl}carbamoyl]-1,3-dioxolane-2,2-dicarboxylic acid, or (4S)-4-[N-(carboxymethyl)-N-[(1R,2R)-2-(4-(4-bromophenoxy)phenyl}-1-methyl-4-phenylbutyl]carbamoyl]-1,3-dioxolane-2,2-dicarboxylic acid.

Particularly preferred is, for example, (4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid, (4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid, (4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid, (4R*,5S*)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid, or (4S*,5R*)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid.

Now, processes for producing the compound of the present invention will be described.

The compound of the formula (I) of the present invention can be prepared, for example, by the following processes 1 to 8.

Process 1

The compound of the formula (I) can be prepared by reacting a compound of the formula (II):

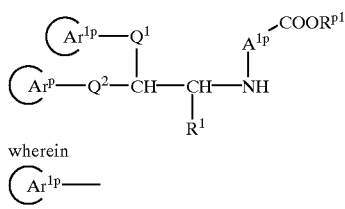

wherein

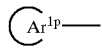

is an aryl group or a heteroaromatic ring group which may have substituent(s) selected from the group consisting of a halogen atom, a nitro group, a cyano group, a lower alkoxycarbonyl group, a lower alkylcarbamoyl group, a lower alkyl group, a lower alkenyl group, a lower fluoroalkyl group, a lower alkoxy group, an aryl group and a heteroaromatic ring group as well as a hydroxyl group, an amino group, a carboxyl group, a carbamoyl group and a lower hydroxyalkyl group, which may be protected;

is a group of the formula

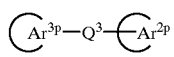

when $Q^2$ is a single bond, or a group of the formula

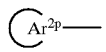

when $Q^2$ is —$(CH_2)_m$— or —$(CH_2)_n$—W—$(CH_2)_p$—; each of

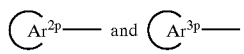

which are the same or different, is an aryl group or a heteroaromatic ring group which may have substituent(s) selected from the group consisting of a halogen atom, a nitro group, a cyano group, a lower alkoxycarbonyl group, a lower alkylamino group, a lower alkylcarbamoyl group, a lower alkyl group, a lower alkenyl group, a lower fluoroalkyl group, a lower alkoxy group and an aralkyloxy group as well as a hydroxyl group, an amino group, a carboxyl group, a carbamoyl group and a lower hydroxyalkyl group, which may be protected; $A^{1p}$ is a $C_{1-4}$ chain hydrocarbon group which may have substituent(s) selected from the group consisting of a halogen atom, a lower alkyl group and a lower alkoxy group as well as a hydroxyl group and a lower hydroxyalkyl group, which may be protected; m is an integer of from 1 to 6; each of n and p which are the same or different, is an integer of from 0 to 3; $Q^1$ is a single bond, a group of the formula —$CH_2O$—, —$OCH_2$—, —$CH_2S$— or —$SCH_2$—, or a $C_{1-6}$ chain hydrocarbon group which may have substituent(s) selected from the group consisting of a halogen atom and a lower alkyl group; $Q^2$ is a single bond, or a group of the formula —$(CH_2)_m$— or —$(CH_2)_n$—W—$(CH_2)_p$—; $Q^3$ is a single bond, an oxygen atom, a sulfur atom, a methylene group, a vinylene group, or a group of the formula —CO—, —NH—, —COO—, —OCO—, —$CH_2CH_2$—, —$OCH_2$—, —$SCH_2$—, —$CH_2O$—, —CH$_2$S—, —NHCO— or —CONH—; R$^1$ is a lower alkyl group; R$^{p1}$ is a hydrogen atom or a protecting group for a carboxyl group; and W is an oxygen atom, a sulfur atom, a vinylene group or an ethynylene group, with a carboxylic acid of the formula (III) or its reactive derivative:

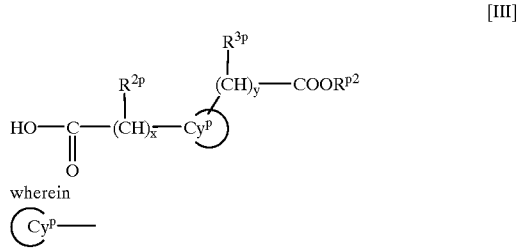

[III]

wherein

Cy$^p$— is an aryl group, a heteroaromatic ring group or an aliphatic ring group which may contain one or two oxygen atoms, which may have substituent(s) selected from the group consisting of a halogen atom, an oxo group, a nitro group, a cyano group, a lower alkylcarbamoyl group, a lower carbamoyloxyalkyl group, a lower alkylcarbamoyloxyalkyl group, a lower alkyl group, a lower fluoroalkyl group, a lower alkoxy group, a lower alkoxyalkyl group, a lower alkoxysulfonyl group, a sulfamoyl group, a lower alkylsulfamoyl group, an aryl group, a heteroaromatic ring group and a group of the formula —PO(OR$^{4p}$)(OR$^{5p}$) as well as a hydroxyl group, an amino group, a carboxyl group, a carbamoyl group, a lower hydroxyalkyl group and a sulfo group, which may be protected; each of R$^{2p}$ and R$^{3p}$ which are the same or different, is a hydrogen atom, a hydroxyl group which may be protected, or a lower alkyl group; each of R$^{4p}$ and R$^{5p}$ which are the same or different, is a hydrogen atom, a lower alkyl group or a protecting group for a phosphono group; x is an integer of from 0 to 2; y is 0 or 1; and R$^{p2}$ is a hydrogen atom, or a protecting group for a carboxyl group, to obtain a compound of the formula (IV):

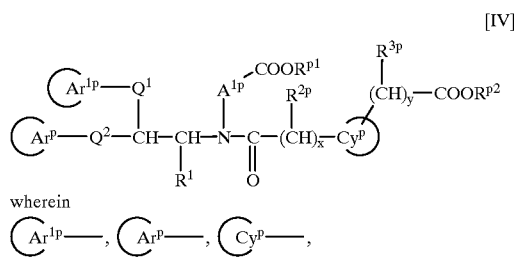

[IV]

wherein

Ar$^{1p}$—, Ar$^p$—, Cy$^p$—,

A$^{1p}$, Q$^1$, Q$^2$, R$^1$, R$^{2p}$, R$^{3p}$, R$^{p1}$, R$^{p2}$, x and y have the above-mentioned meanings, and, if necessary, removing any protecting group.

As the reactive derivative of the carboxylic acid of the formula (III), an acid halide, a mixed acid anhydride, an active ester or an active amide may, for example, be used.

When the carboxylic acid of the formula (III) is used, it is preferred to conduct the reaction in the presence of a condensing agent such as N,N'-dicyclohexylcarbodiimide, 1-ethyl-3-(3-dimethylaminopropyl)carbodiimide or 2-chloro-1,3-dimethylimidazolyl chloride.

The reaction of the compound of the formula (II) with the carboxylic acid of the formula (III) or its reactive derivative, is conducted usually by using 1 mol or an excess molar amount, preferably from 1 to 5 mols, of the carboxylic acid of the formula (III) or its reactive derivative, per mol of the compound of the formula (II).

The reaction is conducted usually in an inert solvent. The inert solvent may, for example, be a halogenated hydrocarbon such as methylene chloride, chloroform, carbon tetrachloride, dichloroethane or trichloroethylene; an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide, or a mixture of such solvents.

The reaction temperature is usually from −70° C. to the boiling point of the solvent used for the reaction, preferably from −20° C. to 100° C.

The reaction time is usually from 5 minutes to 7 days, preferably from 10 minutes to 24 hours.

The above reaction can be conducted in the presence of a base to facilitate the reaction.

As such a base, it is preferred to conduct the reaction in the presence of an inorganic base such as sodium hydroxide, potassium hydroxide, calcium hydroxide, sodium carbonate, potassium carbonate or sodium hydrogencarbonate, or an organic base such as triethylamine, N-ethyldiisopropylamine, pyridine, 4-dimethylaminopyridine or N,N-dimethylaniline.

Such a base is used usually in an amount of 1 mol or an excess molar amount, preferably from 1 to 5 mols, per mol of the reactive derivative of the carboxylic acid of the formula (III).

The acid halide of the compound of the formula (III) can be obtained by reacting the carboxylic acid of the formula (III) with a halogenating agent in accordance with a conventional method. As the halogenating agent, thionyl chloride, phosphorus trichloride, phosphorus pentachloride, phosphorus oxychloride, phosphorus tribromide, oxalyl chloride or phosgene may, for example, be used.

The mixed acid anhydride of the compound of the formula (III) can be obtained by reacting the carboxylic acid of the formula (III) with an alkyl chlorocarbonate such as ethyl chlorocarbonate or with an aliphatic carboxylic acid chloride such as acetyl chloride, in accordance with a conventional method. Further, if structurally possible, an intramolecular acid anhydride may be formed between carboxyl groups at both terminals, or when a carboxyl group is present on a ring, an intramolecular acid anhydride may be formed between such a carboxyl group and a carboxyl group to be involved in the reaction, to constitute a reactive derivative of the carboxylic acid.

The active ester of the compound of the formula (III) can be prepared by reacting the carboxylic acid of the formula (III) with an N-hydroxy compound such as N-hydroxysuccinimide, N-hydroxyphthalimide or 1-hydroxybenzotriazole, or a phenol compound such as a 4-nitrophenol, 2,4-dinitrophenol, 2,4,5-trichlorophenol or pentachlorophenol, in the presence of a condensing agent such as N,N'-dicyclohexylcarbodiimide or 1-ethyl-3-(3-dimethylaminopropyl)carbodiimide in accordance with a conventional method.

The active amide of the compound of the formula (III) can be prepared by reacting the carboxylic acid of the formula (III) with e.g. 1,1'-carbonyldiimidazole or 1,1'-carbonylbis (2-methylimidazole) in accordance with a conventional method.

In the above reaction, when a hydroxyl group, an amino group, a carboxyl group, a phosphono group or a sulfo group which will not be involved in the reaction, is present in a reactant, it is preferred to conduct the reaction after protecting such a hydroxyl group, an amino group, a carboxyl group, a phosphono group or a sulfo group appropriately by a hydroxyl-protecting group, an amino-protecting group, a carboxyl-protecting group, a phosphono-protecting group or a sulfo-protecting group and removing the protecting group after the reaction.

The hydroxyl-protecting group may, for example, be a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a p-nitrobenzyl group or a trityl group; or an acyl group such as a formyl group or an acetyl group. Particularly preferred is a methoxymethyl group, a tetrahydropyranyl group, a trityl group, a tert-butyldimethylsilyl group or an acetyl group.

The amino-protecting group may, for example, be an aralkylidene group such as a benzylidene group, a p-chlorobenzylidene group or a p-nitrobenzylidene group; an aralkyl group such as a benzyl group, a p-methoxybenzyl group, a p-nitrobenzyl group, a benzhydryl group or a trityl group; a lower alkanoyl group such as a formyl group, an acetyl group, a propionyl group, a butyryl group or a pivaloyl group; a lower haloalkanoyl group such as a trifluoroacetyl group; a lower alkoxycarbonyl group such as a methoxycarbonyl group, an ethoxycarbonyl group, a propoxycarbonyl group or a tert-butoxycarbonyl group; a lower haloalkoxycarbonyl group such as a 2,2,2-trichloroethoxycarbonyl group; an alkenyloxycarbonyl group such as a 2-propenyloxycarbonyl group; an aralkyloxycarbonyl group such as a benzyloxycarbonyl group or a p-nitrobenzyloxycarbonyl group; or a lower alkylsilyl group such as a trimethylsilyl group or a tert-butyldimethylsilyl group. Particularly preferred is an acetyl group, a trifluoroacetyl group, a tert-butoxycarbonyl group or a benzyloxycarbonyl group.

The carboxyl-protecting group may, for example, be a lower alkyl group such as a methyl group, an ethyl group, a propyl group, an isopropyl group or a tert-butyl group; a lower haloalkyl group such as a 2,2,2-trichloroethyl group; a lower alkenyl group such as 2-propenyl group; or an aralkyl group such as a benzyl group, a p-methoxybenzyl group, a p-nitrobenzyl group, a benzhydryl group or trityl group. Particularly preferred is a methyl group, an ethyl group, a tert-butyl group, a 2-propenyl group, a benzyl group, a p-methoxybenzyl group or a benzhydryl group.

For each of the phosphono- and sulfo-protecting groups, the carboxyl-protecting group may be used.

After completion of the reaction, conventional treatment is conducted to obtain a crude product of the compound of the formula (IV). The compound of the formula (IV) thus obtained may or may not be purified in accordance with a conventional method, and if necessary, reactions for removing protecting groups for a hydroxyl group, an amino group, a carboxyl group, a phosphono group and a sulfo group may be carried out in a proper combination to obtain a compound of the formula (I).

Removal of protecting groups may vary depending upon their types, but can be conducted in accordance with the methods disclosed in a literature (Protective Groups in Organic Synthesis, T. W. Greene, John Wiley & Sons (1981)) or methods similar thereto, for example by solvolysis employing an acid or a base, by chemical reduction employing a metal hydride complex or by catalytic reduction employing a palladium-carbon catalyst or Raney nickel.

Process 2

A compound of the formula (I-1):

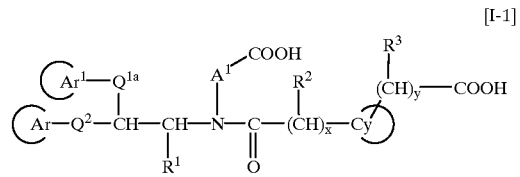

wherein $Q^{1a}$ is $-(CH_2)_v-CH=CH-(CH_2)_w-$ (wherein v and w are as defined above); and

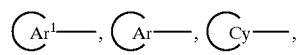

$A^1$, $Q^2$, $R^1$, $R^2$, $R^3$, x and y are as defined above, can be prepared by reacting a compound of the formula (V):

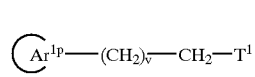

wherein $T^1$ is a triphenylphosphonio group, a dimethoxyphosphoryl group or a diethoxyphosphoryl group; v is an integer of from 0 to 4,

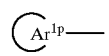

is as defined above, with a compound of the formula (VI):

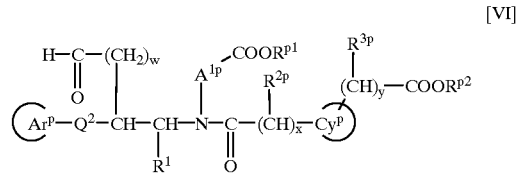

wherein w is an integer of from 0 to 4, provided that the sum of v and w does not exceed 4; and

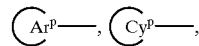

$A^{1p}$, $Q^2$, $R^1$, $R^{2p}$, $R^{3p}$, $R^{p1}$, $R^{p2}$, x and y are as defined above, to obtain a compound of the formula (IV-1):

[IV-1]

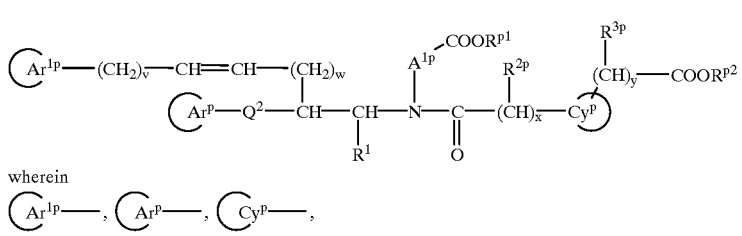

wherein $Ar^{1p}$—, $Ar^p$—, $Cy^p$—, $A^{1p}$, $Q^2$, $R^1$, $R^{2p}$, $R^{3p}$, $R^{p1}$, $R^{p2}$, v, w, x and y are as defined above, and, if necessary, removing any protecting group.

Process 2 is a process for preparing a compound of the formula (I) of the present invention wherein $Q^1$ is —(CH$_2$)$_v$—CH=CH—(CH$_2$)$_w$— (wherein v and w are as defined above) i.e. a compound of the formula (I-1).

The reaction of the compound of the formula (V) with a compound of the formula (VI) is carried out usually by employing equimolar amounts of the two reactants or using a slightly excess amount of one of them.

The reaction is carried out usually in an inert solvent. Such an inert solvent may, for example, be an ether such as ethyl ether, tetrahydrofuran or dioxane; an aromatic hydrocarbon such as benzene, toluene, chlorobenzene or xylene; an aprotic polar solvent such as dimethylformamide, ethyl acetate or hexamethylphosphoric triamide; or a mixture of such solvents.

The reaction temperature is usually from $-100°$ C. to the boiling point of the solvent used for the reaction, preferably from $-70°$ C. to $50°$ C.

The reaction time is usually from 5 minutes to 7 days, preferably from 10 minutes to 24 hours.

Further, it is preferred to carry out the above reaction in the presence of a base. The base may, for example, be sodium hydride, n-butyl lithium, sodium methoxide, potassium tert-butoxide, sodium hydroxide or potassium hydroxide.

Such a base is used in an amount of one mol or an excess molar amount, preferably frog 1 to 5 mols, per mol of the compound wherein T is a triphenylphosphonio group among compounds of the formula (V).

In the above reaction, when a hydroxyl group, an amino group, a carboxyl group, a phosphono group or a sulfo group which will not be involved in the reaction is present in a reactant, it is preferred to carry out the reaction after protecting such a hydroxyl group, an amino group, a carboxyl group, a phosphono group or a sulfo group appropriately by a hydroxyl-protecting group, an amino-protecting group, a carboxyl-protecting group, a phosphono-protecting group or a sulfo-protecting group, and removing any protecting group after the reaction.

The hydroxyl-protecting group, the amino-protecting group, the carboxyl-protecting group, the phosphono-protecting group and the sulfo-protecting group may be the protecting groups mentioned above with respect to process 1.

After completion of the reaction, a conventional treatment may be carried out to obtain a crude product of the compound of the formula (IV-1). The compound of the formula (IV-1) thus obtained may or may not be purified by a conventional method, and if necessary, reactions for removing hydroxyl-, amino-, carboxyl-, phosphono- and sulfo-protecting groups may be carried out in a proper combination to obtain a compound of the formula (I-1).

The method for removing a protecting group varies depending upon the type of the protecting group and the stability of the desired compound (I-1). However, removal of protecting groups can be suitably conducted in accordance with the methods disclosed in the above-mentioned literature or methods similar thereto.

Process 3

A compound of the formula (I-2):

[I-2]

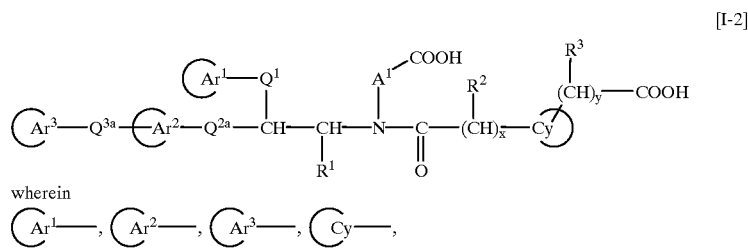

wherein $Ar^1$—, $Ar^2$—, $Ar^3$—, $Cy$—, $A^1$, $Q^1$, $Q^{2a}$, $Q^{3a}$, $R^1$, $R^2$, $R^3$, x and y are as defined above, can be obtained by reacting a compound of the formula (VII):

[VII]

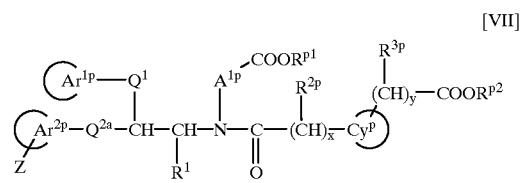

wherein $Q^{2a}$ is a single bond; Z is a leaving group;

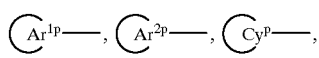

$A^{1p}$, $Q^1$, $R^1$, $R^{2p}$, $R^{3p}$, $R^{p1}$, $R^{p2}$, x and y are as defined above, with a compound of the formula (VIII):

$$[VIII]$$

$$\text{Ar}^{3p}\!-\!Q^{3a}\!-\!T^2$$

wherein $Q^{3a}$ is a single bond or a vinylene group; $T^2$ is a tributylstannyl group or a trimethylstannyl group; and $$\text{Ar}^{3p}\!-\!$$

is as defined above, in the presence of a palladium complex, to obtain a compound of the formula (IV-2):

$$[IV\text{-}2]$$

$$\text{Ar}^{3p}\!-\!Q^{3a}\!-\!\!\left(\!\text{Ar}^{2p}\!\right)\!-\!Q^{2a}\!-\!\underset{R^1}{\overset{\overset{\displaystyle(\text{Ar}^{1p}\!-\!Q^1)}{|}}{\text{CH}}}\!-\!\underset{}{\overset{\overset{\displaystyle A^{1p}\!\overset{\text{COOR}^{p1}}{\diagup}}{|}}{\text{CH}}}\!-\!\text{N}\!-\!\underset{\overset{\displaystyle\|}{\text{O}}}{\overset{\overset{\displaystyle R^{2p}}{|}}{\text{C}}}\!-\!(\text{CH})_x\!-\!\overset{\overset{\displaystyle R^{3p}}{|}}{\underset{\displaystyle}{\text{Cy}^p\!\!\diagup(\text{CH})_y\!-\!\text{COOR}^{p2}}}$$

wherein $$\left(\!\text{Ar}^{1p}\!-\!\right)\!,\ \left(\!\text{Ar}^{2p}\!-\!\right)\!,\ \left(\!\text{Ar}^{3p}\!-\!\right)\!,\ \left(\!\text{Cy}^p\!-\!\right)\!,$$

$A^{1p}$, $Q^1$, $Q^{2a}$, $Q^{3a}$, $R^1$, $R^{2p}$, $R^{3p}$, $R^{p1}$, $R^{p2}$, x and y are as defined above, and, if necessary, removing any protecting group.

Process 3 is a process for producing a compound of the formula (I) of the present invention wherein $Q^2$ is a single bond and $Q^3$ is a single bond or a vinylene group i.e. a compound of the formula (I-2).

The reaction of the compound of the formula (VII) with the compound of the formula (VIII), is conducted usually by using 1 mol or an excess molar amount, preferably from 1 to 3 mols, of the compound of the formula (VIII), and from 0.001 to 1 mol, preferably from 0.01 to 0.1 mol, of the palladium complex, per mol of the compound of the formula (VII).

The reaction is conducted usually in an inert solvent. The inert solvent may, for example, be an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide, or a mixture of such solvents.

The reaction temperature is usually from −70° C. to the boiling point of the solvent used for the reaction, preferably from −20° C. to 150° C.

The reaction time is usually from 5 minutes to 7 days, preferably from 1 hour to 2 days.

The leaving group represented by Z may, for example, be a halogen atom such as a bromine atom or an iodine atom, or a trifluoromethanesulfonyloxy group.

The palladium complex may, for example, be tetrakis(triphenylphosphine)palladium or dichlorobis(triphenylphosphine)palladium.

In the above reaction, when a hydroxyl group, an amino group, a carboxyl group, a phosphono group or a sulfo group which will not be involved in the reaction is present in a reactant, it is preferred to carry out the reaction after protecting such a hydroxyl group, an amino group, a carboxyl group, a phosphono group or a sulfo group appropriately by a hydroxyl-protecting group, an amino-protecting group, a carboxyl-protecting group, a phosphono-protecting group or a sulfo-protecting group, and removing any protecting group after the reaction.

The hydroxyl-protecting group, the amino-protecting group, the carboxyl-protecting group, the phosphono-protecting group and the sulfo-protecting group may be the protecting groups mentioned above with respect to process 1.

After completion of the reaction, a conventional treatment may be carried out to obtain a crude product of the compound of the formula (IV-2). The compound of the formula (IV-2) thus obtained may or may not be purified by a conventional method, and if necessary, reactions for removing hydroxyl-, amino-, carboxyl-, phosphono- and sulfo-protecting groups may be carried out in a proper combination to obtain a compound of the formula (I-2).

The method for removing a protecting group varies depending upon the type of the protecting group and the stability of the desired compound (I-2). However, removal of protecting groups can be suitably conducted in accordance with the methods disclosed in the above-mentioned literature or methods similar thereto.

Process 4

A compound of the formula (I-3):

$$[I\text{-}3]$$

$$R^{12}\!-\!\!\left(\!\text{Ar}\!\right)\!-\!Q^{2a}\!-\!\underset{R^1}{\overset{\overset{\displaystyle(\text{Ar}\!-\!Q^1)}{|}}{\text{CH}}}\!-\!\overset{\overset{\displaystyle A^1\!\overset{\text{COOH}}{\diagup}}{|}}{\text{CH}}\!-\!\text{N}\!-\!\underset{\overset{\displaystyle\|}{\text{O}}}{\overset{\overset{\displaystyle R^2}{|}}{\text{C}}}\!-\!(\text{CH})_x\!-\!\overset{\overset{\displaystyle R^3}{|}}{\underset{\displaystyle}{\text{Cy}\!\!\diagup(\text{CH})_y\!-\!\text{COOH}}}$$

wherein $$\left(\!\text{Ar}^1\!-\!\right)\!,\ \left(\!\text{Ar}\!-\!\right)\!,\ \left(\!\text{Cy}\!-\!\right)\!,$$

$A^1$, $Q^1$, $Q^{2a}$, $R^1$, $R^2$, $R^3$, $R^{12}$, x and y are as defined above, can be obtained by reacting a compound of the formula (IX):

$$[IX]$$

$$\underset{Z}{\overset{}{\left(\!\text{Ar}^p\!\right)}}\!-\!Q^{2a}\!-\!\underset{R^1}{\overset{\overset{\displaystyle(\text{Ar}^{1p}\!-\!Q^1)}{|}}{\text{CH}}}\!-\!\overset{\overset{\displaystyle A^{1p}\!\overset{\text{COOR}^{p1}}{\diagup}}{|}}{\text{CH}}\!-\!\text{N}\!-\!\underset{\overset{\displaystyle\|}{\text{O}}}{\overset{\overset{\displaystyle R^{2p}}{|}}{\text{C}}}\!-\!(\text{CH})_x\!-\!\overset{\overset{\displaystyle R^{3p}}{|}}{\underset{\displaystyle}{\text{Cy}^p\!\!\diagup(\text{CH})_y\!-\!\text{COOR}^{p2}}}$$

wherein $$\left(\!\text{Ar}^{1p}\!-\!\right)\!,\ \left(\!\text{Ar}^p\!-\!\right)\!,\ \left(\!\text{Cy}^p\!-\!\right)\!,$$

$A^{1p}$, $Q^1$, $Q^{2a}$, $R^1$, $R^{2p}$, $R^{3p}$, $R^{p1}$, $R^{p2}$, x, y and z are as defined above, with a compound of the formula (X):

$$R^{12}\!-\!T^2 \quad (X)$$

wherein $R^{12}$ is a lower alkenyl group, and $T^2$ is as defined above, in the presence of a palladium complex, to obtain a compound of the formula (IV-3):

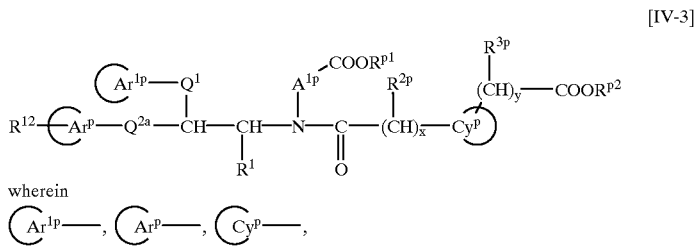

[IV-3]

wherein

, $A^{1p}$, $Q^1$, $Q^{2a}$, $R^1$, $R^{2p}$, $R^{3p}$, $R^{p1}$, $R^{p2}$, $R^{12}$, x and y are as defined above, and, if necessary, removing any protecting group.

Process 4 is a process for producing a compound of the formula (I) of the present invention wherein $Q^2$ is a single bond, and a lower alkenyl group is present on the ring of the group of the formula Ar—, i.e. a compound of the formula (I-3).

The reaction of the compound of the formula (IX) with the compound of the formula (X) can be carried out in the same manner as the step of reacting the compound of the formula (VII) with the compound of the formula (VIII) in the above process 3. Accordingly, with respect to the reaction conditions, etc., conditions similar to that process can be employed.

After completion of the reaction, a conventional treatment may be carried out as it is when no protecting group is present in the product, or after removing any protecting group, when such a protecting group is present in the product, to obtain a compound of the formula (I-3).

Removal of protecting groups and post treatment can be carried out by the methods described in the above process 3.

Process 5

A compound of the formula (I-4):

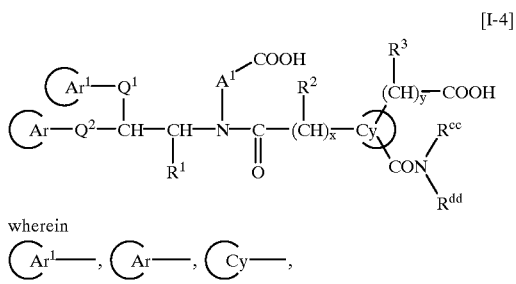

[I-4]

wherein

Ar¹—, Ar—, Cy—, $A^1$, $Q^1$, $Q^2$, $R^1$, $R^2$, $R^3$, $R^{cc}$, $R^{dd}$, x and y are as defined above, can be prepared by reacting a carboxylic acid of the formula (XI) or its reactive derivative:

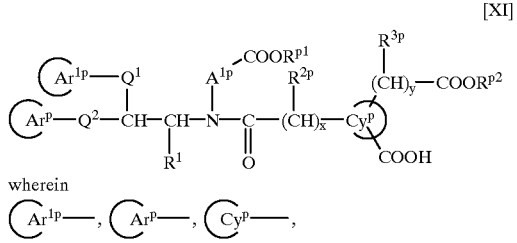

[XI]

wherein

Ar¹ᵖ—, Arᵖ—, Cyᵖ—, $A^{1p}$, $Q^1$, $Q^2$, $R^1$, $R^{2p}$, $R^{3p}$, $R^{p1}$, $R^{p2}$, x and y are as defined above, with a compound of the formula (XII):

[XII]

wherein each of $R^{cc}$ and $R^{dd}$ which are the same or different, is a hydrogen atom or a lower alkyl group, to obtain a compound of the formula (IV-4):

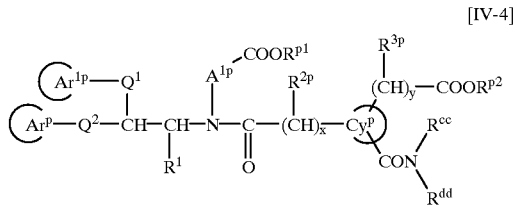

[IV-4]

wherein

Ar¹ᵖ—, Arᵖ—, Cyᵖ—, $A^{1p}$, $Q^1$, $Q^2$, $R^1$, $R^{2p}$, $R^{3p}$, $R^{p1}$, $R^{p2}$, $R^{cc}$, $R^{dd}$, x and y are as defined above, and, if necessary, removing any protecting group.

Process 5 is a process for preparing a compound of the formula (I) of the present invention wherein a carbamoyl group or a lower alkylcarbamoyl group is present on a group of the formula

i.e. a compound of the formula (I-4).

The reactive derivative of a carboxylic acid of the formula (XI) may, for example, be the same as the reactive derivative of a carboxylic acid of the formula (III) in the above Process 1.

The reaction of the carboxylic acid of the formula (XI) or its reactive derivative with a compound of the formula (XII) can be carried out in the same manner as the step for reacting the compound of the formula (II) with the carboxylic acid of the formula (III) or its reactive derivative in the above Process 1. Accordingly, with respect to the reaction conditions, etc., conditions similar to that process can be employed.

After completion of the reaction, the product is subjected to a usual treatment after removing any protecting group if such a protecting group is present or directly if no such protecting group is present, to obtain a compound of the formula (I-4).

Removal of the protecting group and the post treatment may be conducted by the methods described with respect to the above Process 1.

Further, a carboxyl-protected product of the compound of the formula (XI) can be produced in accordance with any one of the methods of the above processes 1 to 4, and a compound of the formula (XI) can be obtained by selectively removing the protecting group for a carboxyl group which is involved in the reaction of the compound.

The step of selectively removing the protecting group for a carboxyl group which is involved in the reaction, is suitably selected from various methods depending upon the type and characteristics of the protecting group. Namely, by utilizing the difference in stability against an acid, a base or deduction between the caroxyl-protecting group and other protecting groups, the protecting group may selectively removed by a conventional means such as an acid, a base or reduction. With respect to the specific conditions for such reactions, a method disclosed in a literature "Protective Groups in Organic Synthesis, T. W. Greene, John Wiley & Sons (1981)" or a method similar thereto, may be employed.

Process 6

A compound of the formula (I-5):

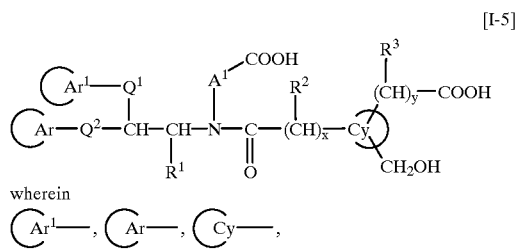

wherein $A^1$, $Q^1$, $Q^2$, $R^1$, $R^2$, $R^3$, x and y are as defined above, can be obtained by reducing a carboxylic acid of the formula (XI) or its reactive derivative:

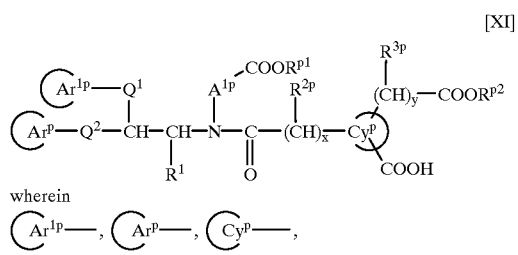

wherein $A^{1p}$, $Q^1$, $Q^2$, $R^1$, $R^{2p}$, $R^{3p}$, $R^{p1}$, $R^{p2}$, x and y are as defined above, to obtain a compound of the formula (IV-5):

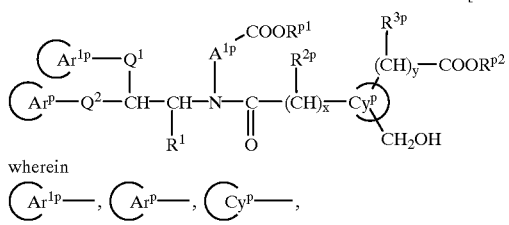

wherein $A^{1p}$, $Q^1$, $Q^2$, $R^1$, $R^{2p}$, $R^{3p}$, $R^{p1}$, $R^{p2}$, x and y are as defined above, and, if necessary, removing any protecting group.

Process 6 is a process for preparing a compound of the formula (I) of the present invention wherein a hydroxymethyl group is present on a group of the formula

i.e. a compound of the formula (I-5).

The reactive derivative of a carboxylic acid of the formula (XI) may be the same as the reactive derivative of a carboxylic acid of the formula (III) in the above Process 1.

The step of reducing the carboxylic acid of the formula (XI) or its reactive derivative to obtain a compound of the formula (IV-5), is carried out usually in an inert solvent giving no adverse effect to the reaction, preferably by reacting a reducing agent such as a metal hydride complex such as sodium borohydride to the reactive derivative of a carboxylic acid.

Such an inert solvent may, for example, be an inert solvent, for example, an ether such as dimethoxyethane, dioxane, tetrahydrofuran or diglyme; or an aprotic polar solvent such as dimethylformamide or dimethylacetamide or water, or a mixed solvent thereof. Particularly preferred is an ether such as dimethoxyethane, dioxane, tetrahydrofuran or diglyme, or a solvent mixture thereof with water.

The reducing agent is used in an amount of 1 mol or an excess mol, preferably from 1 to 5 mol, per mol of the reactive derivative of a carboxylic acid of the formula (XI).

The reaction temperature is usually from −78° C. to the boiling point of the solvent used for the reaction, preferably from −20° C. to 80° C.

The reaction time is usually from 5 minutes to 7 days, preferably from 10 minutes to 24 hours.

After completion of the reaction, the product is subjected to a usual treatment after removing any protecting group if such a protecting group is present, or directly if no such protecting group is present, to obtain a compound of the formula (I-5).

Removal of the protecting group and the post treatment may be conducted by the methods described with respect to the above Process 1.

Process 7

A compound of the formula (I-6):

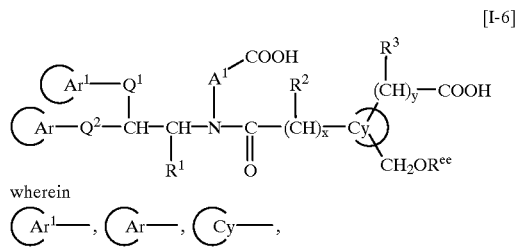

wherein $A^1$, $Q^1$, $Q^2$, $R^1$, $R^2$, $R^3$, $R^{cc}$, x and y are as defined above, can be obtained by reacting a compound of the formula (IV-5):

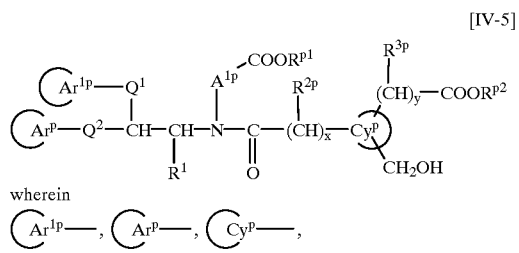

wherein $A^{1p}$, $Q^1$, $Q^2$, $R^1$, $R^{2p}$, $R^{3p}$, $R^{p1}$, $R^{p2}$, x and y are as defined above, with a compound of the formula (XIII):

$$R^{ee}\text{—}Z^a \qquad (XIII)$$

wherein $R^{cc}$ is a lower alkyl group; $Z^a$ is a leaving group, to obtain a compound of the formula (IV-6):

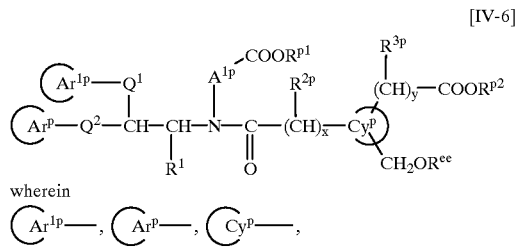

wherein $A^{1p}$, $Q^1$, $Q^2$, $R^1$, $R^{2p}$, $R^{3p}$, $R^{p1}$, $R^{p2}$, $R^{cc}$, x and y are as defined above, and, if necessary removing any protecting group.

Process 7 is a process for preparing a compound of the formula (I) of the present invention wherein a lower alkoxymethyl group is present on a group of the formula

i.e. a compound of the formula (I-6).

The reaction of the compound of the formula (IV-5) with the compound of the formula (VIII) is conducted usually by using 1 mol or an excess molar amount, preferably from 1 to 3 mols, of the compound of the formula (XIII), per mol of the compound of the formula (IV-5).

The reaction is conducted usually in an inert solvent. The inert solvent may, for example, be a halogenated hydrocarbon such as methylene chloride, chloroform, carbon tetrachloride, dichloroethane or trichloroethylene; an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide, or a mixture of such solvents.

The reaction temperature is usually from –70 ° C. to the boiling point of the solvent used for the reaction, preferably from –20° C. to 100° C.

The reaction time is usually from 5 minutes to 7 days, preferably from 10 minutes to 24 hours.

Further, the above reaction is preferably carried out in the presence of a base to facilitate the reaction. Such a base may, for example, be an inorganic base such as sodium hydride, n-butyllithium, sodium hydroxide, potassium hydroxide, calcium hydroxide, sodium carbonate, potassium carbonate or sodium hydrogen carbonate, or an organic base such as triethylamine, N-ethyldiisopropylamine, pyridine, 4-dimethylaminopyridine or N,N-dimethylaniline.

Such a base is used usually in an amount of 1 mol or an excess molar amount, preferably from 1 to 5 mols, per mol of the compound of the formula (IV-5).

The leaving group represented by $Z^a$ may, for example, be a halogen atom such as a chlorine atom, a bromine atom or an iodine atom, or an organic sulfonyloxy group such as a methanesulfonyloxy group, a p-toluenesulfonyloxy group or a benzenesulfonyloxy group.

After completion of the reaction, the product is subjected to a usual treatment after removing any protecting group if such a protecting group is present or directly if no such protecting group is present, to obtain a compound of the formula (I-6).

Removal of the protecting group and the post treatment may be conducted by the methods described with respect to the above Process 1.

Process 8

A compound of the formula (I-7):

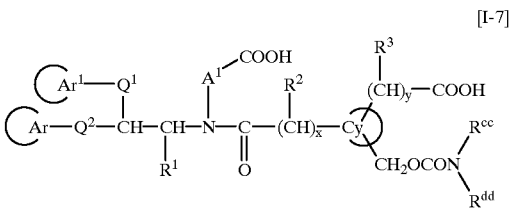

wherein $A^1$, $Q^1$, $Q^2$, $R^1$, $R^2$, $R^3$, $R^{cc}$, $R^{dd}$, x and y are as defined above, can be obtained by reacting a compound of the formula (IV-5):

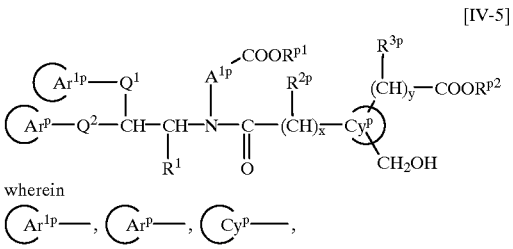

wherein $A^{1p}$, $Q^1$, $Q^2$, $R^1$, $R^{2p}$, $R^{3p}$, $R^{p1}$, $R^{p2}$, x and y are as defined above, with a carbamoyl-modifying agent selected from the group consisting of chlorosulfonyl isocyanate, a compound of the formula (XIV):

     (XIV)

wherein $R^{ff}$ is a lower alkyl group, and a compound of the formula (XV):

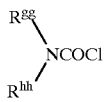     [XV]

wherein each of $R^{gg}$ and $R^{hh}$ which are the same or different, is a lower alkyl group, to obtain a compound of the formula (IV-7):

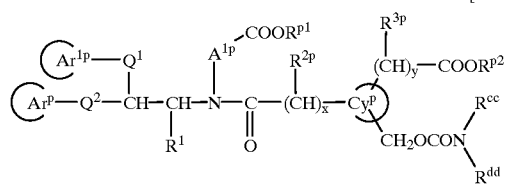     [IV-7]

wherein

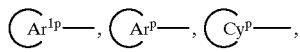

$A^{1p}$, $Q^1$, $Q^2$, $R^1$, $R^{2p}$, $R^{3p}$, $R^{p1}$, $R^{p2}$, $R^{cc}$, $R^{dd}$, x and y are as defined above, and, if necessary removing any protecting group.

Process 8 is a process for preparing a compound of the formula (I) of the present invention wherein a carbamoyloxymethyl group or a lower alkylcarbamoyloxymethyl group is present on a group of the formula

i.e. a compound of the formula (I-7).

According to the process, the desired compound can be obtained by selecting a carbamoyl-modifying agent from a group consisting of chlorosulfonyl isocyanate, the compound of the formula (XIV) and the compound of the formula (XV) depending upon the number of lower alkyl groups on the nitrogen atom of the carbamoyl group of the compound of the formula (I-7) and using it for the reaction.

Namely, by selecting and using for the reaction chlorosulfonyl isocyanate, a compound of the formula (I-7) wherein $R^{cc}$ and $R^{dd}$ are both hydrogen atoms can be produced; by selecting and using for the reaction the compound of the formula (XIV), a compound of the formula (I-7) wherein either one of $R^{cc}$ and $R^{dd}$ is a hydrogen atom, and the other is $R^{ff}$, can be obtained; and by selecting and using for the reaction the compound of the formula (XV), a compound of the formula (I-7) wherein $R^{cc}$ and $R^{dd}$ correspond to $R^{gg}$ and $R^{hh}$, respectively, can be produced.

The reaction of the compound of the formula (IV-5) with a carbamoyl-modifying agent selected from the group consisting of chlorosulfonyl isocyanate, the compound of the formula (XIV) and the compound of the formula (XV) is carried out usually by employing 1 mol or an excess molar amount, preferably from 1 to 3 mols, of the carbamoyl-modifying agent, per mol of the compound of the formula (IV-5).

The reaction is carried usually in an inert solvent. Such an inert solvent may, for example, be a halogenated hydrocarbon such as methylene chloride, chloroform, carbon tetrachloride, dichloroethane or trichloroethylene; an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide, or a mixture of such solvents.

The reaction temperature is usually from −70° C. to the boiling point of the solvent used for the reaction, preferably from −20° C. to 120° C.

The reaction time is usually from 5 minutes to 7 days, preferably from 10 minutes to 24 hours.

Further, the above reaction is preferably carried out in the presence of a base to facilitate the reaction. Such a base may, for example, be an inorganic base such as sodium hydride, sodium hydroxide, potassium hydroxide, calcium hydroxide, sodium carbonate, potassium carbonate or sodium hydrogen carbonate, or an organic base such as triethylamine, N-ethyldiisopropylamine, pyridine, 4-dimethylaminopyridine or N,N-dimethylaniline.

Such a base is used in an amount of 1 mol or an excess molar amount, preferably from 1 to 5 mols, per mol of the compound of the formula (IV-5).

When chlorosulfonyl isocyanate is selected as the carbamoyl-modifying agent, it is usually necessary to subject the product to a hydrolysis reaction after completion of the reaction.

After completion of the reaction, the product is subjected to a usual treatment after removing any protecting group if such a protecting group is present or directly if no such protecting group is present, to obtain a compound of the formula (I-7).

Removal of the protecting group and the post treatment may be conducted by the methods described with respect to the above Process 1.

Isolation and purification of the compound of the formula (I), (I-2), (I-3), (I-4), (I-5), (I-6) or (I-7), obtained by the above process can be conducted by a single use or a proper combination of conventional separating means such as column chromatography employing silica gel, adsorbent resin, etc., liquid chromatography, solvent extraction and recrystallization-reprecipitation.

The compound of the formula (I), (I-2), (I-3), (I-4), (I-5), (I-6), or (I-7) can be converted to a pharmaceutically acceptable salt or ester by a conventional method. Reversely, the conversion from the salt or ester to a free carboxylic acid can also be conducted by a conventional method.

The compounds of the formulas (II), (III), (V), (VI), (VIII), (X), (XII), (XIII), (XIV) and (XV) may be commercially available or can be prepared in accordance with the methods disclosed in literatures (J. Med. Chem., vol. 10, 717 (1967); ibid., 725; Tetrahedron Letters, vol. 36, 7459 (1995); U.S. Pat. Nos. 3,855,248; 4,182,718) or methods similar thereto, or in accordance with the following processes or the methods disclosed in Examples and Reference Examples.

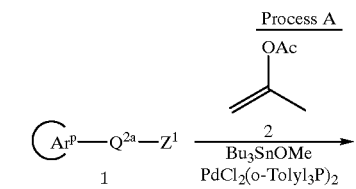

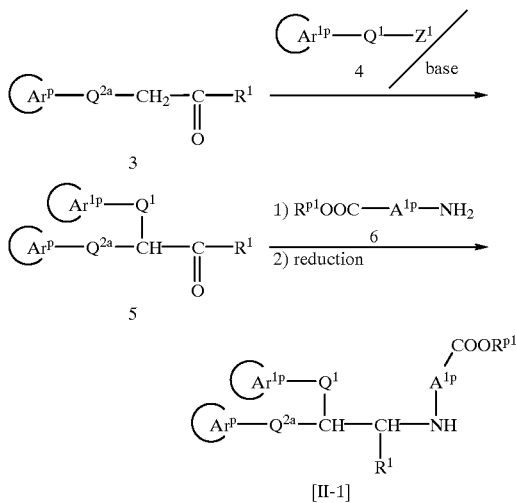

In the above formulas, Ac is an acetyl group; Bu is a butyl group; Me is a methyl group; $Z^1$ is a leaving group selected from the group consisting of a chlorine atom, a bromine atom, an iodine atom and a trifluoromethanesulfonyloxy group; and

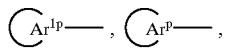

$A^{1p}$, $Q^1$, $Q^{2a}$, $R^1$ and $R^{p1}$ are as defined above.

By this process, the desired compound (II-1) can be prepared by reacting a compound of the formula 1 with propenyl acetate 2 using a palladium complex as a catalyst, to obtain a ketone compound 3, then reacting an alkylating agent of the formula 4 to the ketone compound 3 to obtain a compound of the formula 5, reacting an amine compound of the formula 6 to the compound 5, followed by reduction.

The above reaction steps will be described in detail referring to suitable reaction conditions, etc.

The first step of preparing the ketone compound 3 is conducted usually by reacting 1 mol or an excess molar amount of propenyl acetate 2, 1 mol or an excess molar amount of tributyltin methoxide and from 0.001 to 0.01 mol of dichloro[bis(tris-o-tolylphosphine)]palladium to 1 mol of the starting material compound 1 in a solvent inert to the reaction, such as tetrahydrofuran, ethyl ether, benzene or toluene.

The reaction temperature is usually from −80° C. to the boiling point of the solvent used for the reaction, preferably from 0° C. to 150° C.

The reaction time is usually from 5 minutes to 48 hours, preferably from 30 minutes to 24 hours.

The step of preparing the compound of the formula 5 from the ketone compound 3, can be conducted by reacting an equimolar amount or an excess molar amount, preferably from 1 to 2 mols, of the alkylating agent of the formula 4 to 1 mol of the ketone compound 3 in the presence of a base in an inert solvent which does not adversely affect the reaction or without using any solvent.

The inert solvent may, for example, be an ether such as ethyl ether, tetrahydrofuran or dioxane; an aromatic hydrocarbon such as benzene, toluene or xylene; an aprotic polar solvent such as dimethylformamide, dimethyl sulfoxide or hexamethylphosphoric triamide, or a mixture of such solvents.

The base to be used for this reaction, may, for example, be an alkali metal hydride such as sodium hydride, lithium hydride or potassium hydride; a lithium amide such as lithium amide, lithium diisopropylamide or lithium bis (trimethylsilyl)amide; an alkyl lithium such as methyl lithium, butyl lithium or tert-butyl lithium; an alkali metal alkoxide such as sodium methoxide, sodium ethoxide or potassium tert-butoxide; or an alkali metal hydroxide such as sodium hydroxide, potassium hydroxide or lithium hydroxide.

The base is used usually in an amount of 1 mol or an excess molar amount, preferably from 1 to 5 mols, per mol of the starting material alkylating agent 4.

The reaction temperature is usually from −100° C. to the boiling point of the solvent used for the reaction, preferably from −80° C. to 100° C. The reaction time is usually from 10 minutes to 48 hours, preferably from 30 minutes to 24 hours.

The step of preparing the desired compound (II-1) from the compound of the formula 5 can be conducted usually in an inert solvent such as methanol, ethanol, benzene, ethyl ether or tetrahydrofuran by reacting 1 mol or an excess molar amount, preferably from 1 to 2 mols, of the amine compound of the formula 6 to 1 mol of the compound of the formula 5 to preliminarily form an imine, which is subsequently reduced.

The reaction temperature in the process for forming the above imine is usually from 0° C. to the boiling point of the solvent used for the reaction, preferably from room temperature to 100° C. The reaction time is usually from 5 minutes to 48 hours, preferably from 30 minutes to 24 hours. After the formation of the imine, the reaction solution may be used as it is for the subsequent step of the reduction reaction, or the reaction solution may be distilled or subjected to a conventional separation means to isolate the imine compound, which is then subjected to the subsequent reduction.

The reduction can be carried out by using a metal hydride complex such as sodium borohydride, sodium cyanoborohydride or lithium aluminum hydride, or by catalytic reduction employing a palladium-carbon catalyst or a Raney nickel catalyst.

When a metal hydride complex is used as a reducing agent, the reducing agent is used usually in an amount of 1 mol or an excess molar amount, preferably from 1 to 5 mols, per mol of the above imine.

For the reduction, an inert solvent, for example, an alcohol such as methanol or ethanol; an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene or toluene; or a mixture of such solvents, can be used appropriately as a solvent depending upon the type of the reducing agent.

The reaction temperature is usually from 0° C. to room temperature, and the reaction time is usually from 1 hour to 6 hours.

The compounds of the formulas 1, 2, 4 and 6 may be commercially available or can be produced by a proper combination, as the case requires, of the methods disclosed in Reference Examples, or conventional methods or methods similar thereto.

Particularly, a compound of the formula 1 having an aryloxy group on the group of the formula

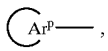

can be produced by reacting a compound of the formula 1 having a hydroxyl group on the group of the formula

with an aryl compound having a halogen atom as a leaving group, or by reacting a compound of the formula 1 having a halogen atom as a leaving group on the group of the formula

with an aryl compound having a hydroxyl group.

This reaction can be carried out usually in a solvent inert to the reaction using a copper powder, a copper(I) halide or a copper alkoxide as a catalyst.

Such an inert solvent may, for example, be pyridine, dimethylformamide, dimethyl sulfoxide or hexamethylphosphoric triamide; the copper(I) halide may, for example, be copper(I) chloride, copper(I) bromide or copper(I) iodide; and the copper alkoxide may, for example, be copper(I) methoxide, copper(I) ethoxide, copper(I) propoxide or copper(I) butoxide.

The reaction temperature is usually from room temperature to the boiling point of the solvent used for the reaction, and the reaction time is usually from 1 hour to 48 hours.

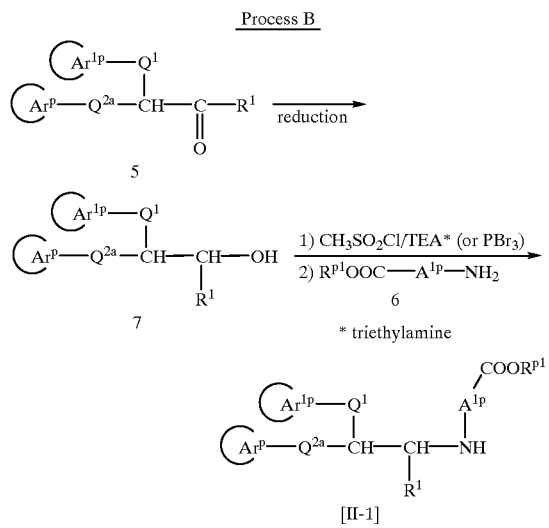

In the above formulas,

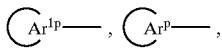

$A^{1p}$, $Q^1$, $Q^{2a}$, $R^1$ and $R^{p1}$ are as defined above.

According to this process, the desired compound (II-1) can be prepared by reacting a reducing agent such as a metal hydride complex to a compound of the formula 5 to obtain an alcohol compound 7 and reacting an amine compound of the formula 6 to the alcohol compound 7.

The above reaction steps will be described in detail referring to suitable reaction conditions, etc.

The step for reducing the compound of the formula 5 to the alcohol compound 7 can be conducted usually by using a metal hydride complex such as sodium borohydride, diisobutyl aluminum hydride, lithium aluminum hydride or lithium tri-sec-butylborohydride (L-selectride™), or by catalytic reduction employing e.g. a palladium-carbon catalyst or a Raney nickel catalyst, in an inert solvent which does not adversely affect the reaction.

When the metal hydride complex is used as the reducing agent, such a reducing agent is used usually in an amount of 1 mol or an excess molar amount, preferably from 1 to 5 mols, per mol of the starting material compound 5.

The inert solvent to be used in this reaction may be suitably selected depending upon the type of the reducing agent.

For example, when the reducing agent is sodium borohydride, an inert solvent, such as an alcohol such as methanol or ethanol; an ether such as dimethoxyethane, dioxane, tetrahydrofuran or diglyme; an aprotic polar solvent such as dimethylformamide or dimethylacetamide, or water, or a solvent mixture thereof, may be used, and particularly preferred is an alcohol such as methanol or ethanol.

For example, when the reducing agent is diisobutyl aluminum hydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; an aromatic hydrocarbon such as benzene or toluene; methylene chloride, or a solvent mixture thereof, may be used, and particularly preferred is toluene or methylene chloride.

For example, when the reducing agent is lithium aluminum hydride or lithium tri-sec-butylborohydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene or toluene, or a solvent mixture thereof, may be used, and particularly preferred is ethyl ether or tetrahydrofuran.

For the catalytic reduction, the solvent is preferably an alcohol such as methanol or ethanol.

The reaction temperature and the reaction time vary it depending upon the stability and the susceptibility to the reduction reaction of the starting material ketone compound 5, the type of the reducing agent and the type of the solvent. However, the reaction temperature is usually from −80° C. to 100° C., preferably from −70° C. to 40° C., and the reaction time is usually from 5 minutes to 2 days, preferably from 30 minutes to 24 hours.

The step of preparing the desired compound (II-1) from a compound of the formula 7 can be carried out by reacting a sulfonating agent such as methanesulfonyl chloride to the alcohol compound of the formula 7 in the presence of a base, or reacting a halogenating agent such as thionyl chloride or phosphorus tribromide thereto, to convert the hydroxyl group in the formula to a leaving group, followed by reacting an amine compound of the formula 6.

The reaction for introducing the leaving group can be conducted usually by reacting 1 mol or an excess molar amount, preferably from 1 to 2 mols, of a sulfonating agent and a base such as triethylamine to 1 mol of the alcohol compound 7 in an inert solvent such as methylene chloride, chloroform, benzene, tetrahydrofuran or ethyl acetate, or using 1 mol or an excess molar amount, preferably from 1 to 5 mols, of a halogenating agent.

The reaction temperature is usually from −70° C. to the boiling point of the solvent used for the reaction, preferably from −20° C. to 80° C., and the reaction time is usually from 5 minutes to 48 hours, preferably from 30 minutes to 24 hours.

Then, the step of reacting an amine compound 6 to the compound having the leaving group introduced, obtained by the above reaction, can be conducted usually by employing 1 mol or an excess molar amount, preferably from 1 to 50 mols, of the amine compound 6 per mol of the starting compound having the leaving group, in an inert solvent such as methylene chloride, chloroform, benzene, ethyl ether or tetrahydrofuran.

If necessary, this reaction can be conducted in the presence of a base other than the amine compound of the formula 6.

As such a base, an inorganic base such as sodium hydroxide, potassium hydroxide, calcium hydroxide, sodium carbonate, potassium carbonate or sodium hydrogencarbonate, or an organic base such as triethylamine, N-ethyldiisopropylamine, pyridine or N,N-dimethylaniline may, for example, be mentioned.

Such a base is used usually in an amount of 1 mol or an excess molar amount, preferably from 1 to 5 mols, per mol of the starting material compound.

The reaction temperature is usually from −50° C. to 150° C., preferably from −20° C. to 100° C., and the reaction time is usually from 5 minutes to 7 days, preferably from 10 minutes to 24 hours.

such as methanesulfonyl chloride in the presence of a base such as triethylamine and then reacting phthalimide (or sodium azide) in the presence of a base, to the alcohol compound of the formula 7, to obtain a phthalimide-protected form (or an azide compound) of the amine compound 8, then reacting hydrazine (or a reducing agent) to remove the phthalimide group (or reduce the azide group) to obtain an amine product of the formula 8, and finally reacting a compound of the formula 9 to the compound 8, followed by reduction.

The above reaction steps will be described in detail referring to suitable reaction conditions, etc.

For the step of producing the compound of the formula 8 from the alcohol compound 7, various synthetic methods and reaction conditions well known in organic synthetic chemistry for converting alcohol compounds to amines, may be employed. For example, it is preferred to employ a Mitsunobu reaction using diethyl azodicarboxylate, triphenylphosphine and phthalimide (or hydrogen azide or diphenylphosphoryl azide) or a method which comprises sulfonylation with a sulfonylation agent such as methanesulfonyl chloride in the presence of a base such as triethylamine, then reacting phthalimide (or sodium azide) in the presence of a base, and then treating the obtained phthalimide compound with hydrazine (or reducing the azide compound).

The above reactions are conducted usually in a solvent inert to the reaction. The inert solvent may, for example, preferably be tetrahydrofuran, dimethoxyethane, benzene or toluene in the case of the above-mentioned Mitsunobu reaction; methylene chloride, chloroform, tetrahydrofuran, benzene, ethyl acetate or dimethylformamide in the case of

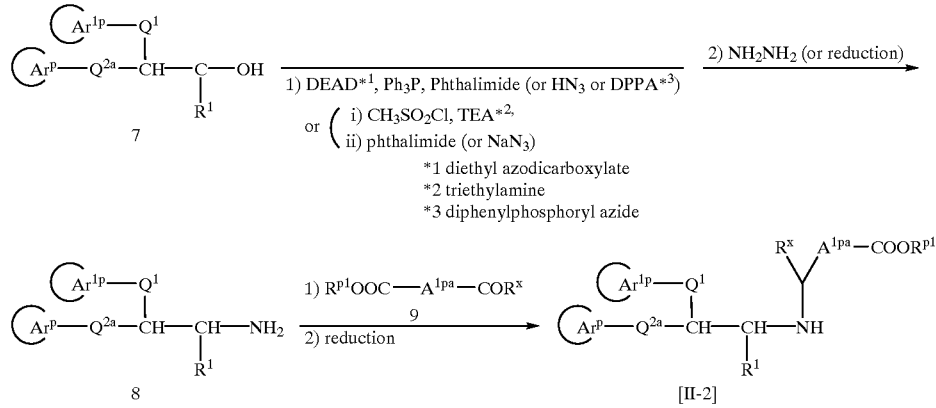

In the above formulas, $A^{1pa}$ is a $C_{1-3}$ chain hydrocarbon group which may have substituent(s) selected from the group consisting of a halogen atom, a lower alkyl group, a lower alkoxy group, and hydroxyl and lower hydroxyalkyl groups which may be protected; $R^x$ is a hydrogen atom or a lower alkyl group;

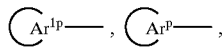

$Q^1$, $Q^{2a}$, $R^1$ and $R^{p1}$ are as defined above.

According to this process, the desired compound (II-2) can be prepared by firstly reacting diethyl azodicarboxylate, triphenylphosphine and phthalimide (or hydrogen azide or diphenylphosphoryl azide) or reacting a sulfonylation agent the sulfonylation followed by the reaction with phthalimide (or sodium azide); an alcohol such as methanol or ethanol in the next step of the phthalimide-removing reaction with hydrazine; an ether such as ethyl ether or tetrahydrofuran in the case where a metal hydride complex is used as the reducing agent in the reduction reaction of the azide compound; water-containing tetrahydrofuran in the case where phosphine reduction is conducted with triphenylphosphine or the like; and an alcohol such as methanol or ethanol in the reduction by catalytic reduction.

With respect to the amounts of the reagents to be used, in the above Mitsunobu reaction, each of diethyl azodicarboxylate, triphenylphosphine and phthalimide (or hydrogen azide or diphenylphosphoryl azide) is used in an amount of 1 mol or an excess molar amount, preferably from 1 to 5 mols, per mol of the starting material alcohol compound 7. In the reaction with the phthalimide (or sodium azide) after the sulfonylation, the sulfonylation agent such as methanesulfonyl chloride is used in an amount of 1 mol or an excess molar amount, preferably from 1 to 2 mols, per mol of the alcohol compound 7, and the base such as triethylamine used at that time is usually in an amount of 1 mol or an excess molar amount, preferably from 1 to 2 mols, per mol of the sulfonylation agent. In the next step of the reaction with phthalimide (or sodium azide) in the presence of a base, 1 mol or an excess molar amount, preferably from 1 to 5 mols of each of phthalimide and the base (or sodium azide) is used per mol of the sulfonylation agent. Here, the base to be used together with phthalimide is preferably sodium carbonate or potassium carbonate. Otherwise, without using such a base, a sodium salt or a potassium salt of phthalimide may be used by itself. Then, in the reaction for removing the phthalimide group with hydrazine, hydrazine is used in an amount of 1 mol or an excess molar amount, preferably from 1 to 10 mols, per mol of the phthalimide compound as the starting material compound. In the reduction of the azide compound with a metal hydride complex or with triphenylphosphine, the reducing agent is used usually in an amount of 1 mol or an excess molar amount, preferably from 1 to 2 mols, per mol of the azide compound.

In the case of the above Mitsunobu reaction, the reaction temperature is usually from −70° C. to 100° C., preferably from −20° C. to 50° C., and the reaction time is usually from 5 minutes to 48 hours, preferably from 30 minutes to 24 hours. In the reaction for removing the phthalimide group by hydrazine, the reaction temperature is usually from 0° C. to the boiling point of the solvent used for the reaction, preferably from room temperature to 100° C., and the reaction time is usually from 5 minutes to 48 hours, preferably from 30 minutes to 24 hours. In the reaction for converting the azide compound to the amine compound by reduction, when a metal hydride complex is used as the reducing agent, the reaction temperature is usually from −70° C. to 150° C., preferably from −20° C. to 50° C., and the reaction time is usually from 5 minutes to 48 hours, preferably from 10 minutes to 10 hours. When triphenylphosphine is used as the reducing agent, the reaction temperature is usually from room temperature to the boiling point of the solvent used for the reaction, preferably from 30° C. to 100° C., and the reaction time is usually from 10 minutes to 48 hours, preferably from 30 minutes to 24 hours. Further, in the case of the reduction by catalytic reduction, the reaction temperature is usually from 0° C. to 100° C., preferably from room temperature to 50° C., and the reaction time is usually from 10 minutes to 48 hours, preferably from 10 minutes to 24 hours.

The step for producing the desired compound (II-2) from the compound of the formula 8 is carried out usually by preliminarily forming an imine by reacting 1 mol or an excess molar amount, preferably from 1 to 2 mols of the compound of the formula 9 to 1 mol of the compound of the formula 8 in an inert solvent such as methanol, ethanol, benzene, ethyl ether or tetrahydrofuran, and then reducing it.

This step can be carried out in the same manner as the step for producing the desired compound (II-1) from the compound of the formula 5 in the above process A. Accordingly, with respect to the reaction conditions, etc., similar modes may be employed.

Further, the compound of the formula 9 may be commercially available or can be produced by a proper combination, as the case requires, of the methods disclosed in Reference Examples, or conventional methods or methods similar thereto.

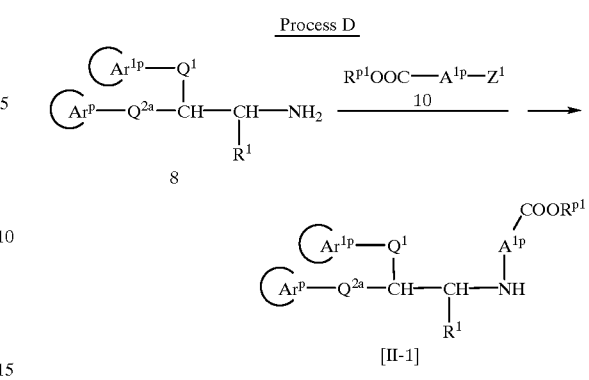

In above formulas,

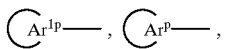

$A^{1p}$, $Q^1$, $Q^{2a}$, $R^1$, $R^{p1}$ and $Z^1$ are as defined above.

According to this process, the compound of the formula (II-1) can be prepared by reacting an alkylating agent of the formula 10 to an amine compound of the formula 8 in the presence of a suitable base.

The above reaction step will be described in detail referring to suitable reaction conditions, etc.

The above reaction is carried out usually in a solvent inert to the reaction and can be carried out by reacting 1 mol or an excess molar amount, preferably from 1 to 2 mols, of the alkylating agent of the formula 10 to 1 mol of the amine compound 8 in the presence of a base.

Such an inert solvent may, for example, be an ether such as ethyl ether, tetrahydrofuran or dioxane; an aromatic hydrocarbon such as benzene, toluene or xylene; an aprotic polar solvent such as dimethylformamide, dimethyl sulfoxide or hexamethylphosphoric triamide, or a mixture of such solvents.

The base to be used in this reaction, may, for example, be an alkali metal hydride such as sodium hydride, lithium hydride or potassium hydride; a lithium amide such as lithium amide, lithium diisopropylamide or lithium bistrimethylsilylamide; an alkyl lithium such as methyl lithium, butyl lithium or tert-butyl lithium; an alkali metal alkoxide such as sodium methoxide, sodium ethoxide or potassium tert-butoxide; an alkali metal hydroxide such as sodium hydroxide, potassium hydroxide or lithium hydroxide; or an alkali metal carbonate such as sodium carbonate or potassium carbonate.

Such a base is used usually in an amount of 1 mol or an excess molar amount, preferably from 1 to 5 mols, per mol of the starting material alkylating agent 10.

The reaction temperature is usually from −100° C. to the boiling point of the solvent used for the reaction, preferably from −80° C. to 100° C., and the reaction time is usually from 10 minutes to 48 hours, preferably from 30 minutes to 24 hours.

Process E

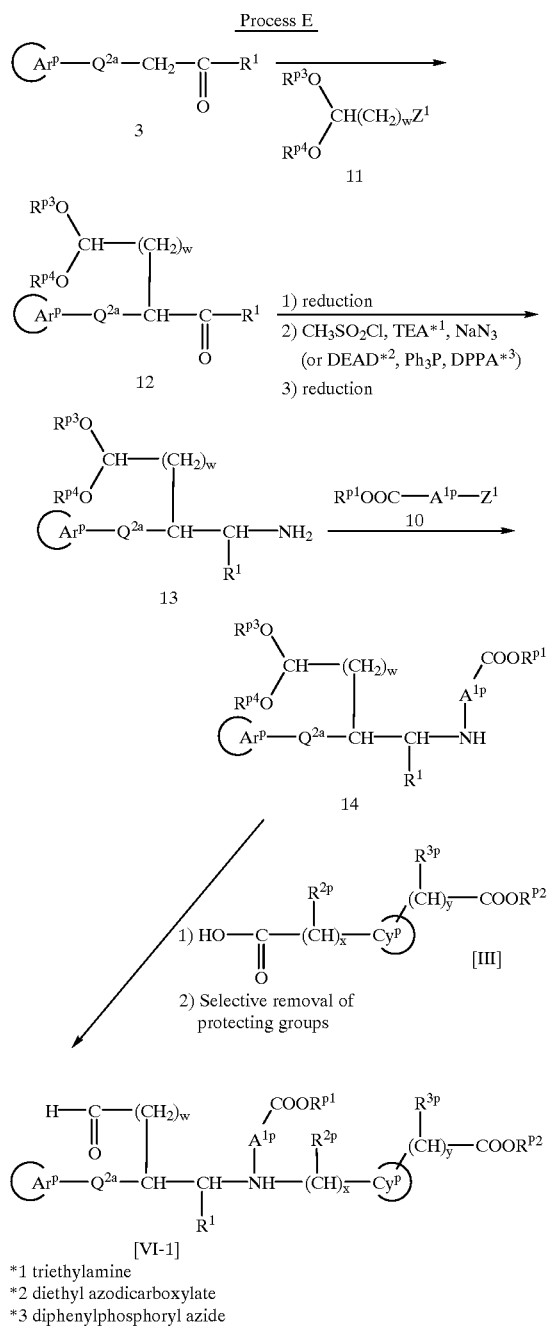

*1 triethylamine
*2 diethyl azodicarboxylate
*3 diphenylphosphoryl azide

In the above formulas, each of $R^{p3}$ and $R^{p4}$ which are the same or different, is a methyl group or an ethyl group, or $R^{p3}$ and $R^{p4}$ together form an ethylene group; and

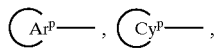

$A^{1p}, Q^{2a}, R^1, R^{2p}, R^{3p}, R^{p1}, R^{p2}$, w, x, y and $Z^1$ are as defined above.

According to this process, the desired compound (VI-1) can be prepared by firstly reacting an alkylating agent of the formula 11 to a ketone compound of the formula 3 to obtain a compound of the formula 12, reacting a reducing agent such as a metal hydride complex to the compound 12 to obtain an alcohol compound, then reacting diethyl azodicarboxylate, triphenylphosphine and phthalimide (or hydrogen azide or diphenylphosphoryl azide) or reacting a sulfonylation agent such as methanesulfonyl chloride in the presence of a base such as triethylamine, and then reacting phthalimide (or sodium azide) in the presence of a base, to obtain a phthalimide-protected form (or an azide compound) of the amine compound 13, then reacting hydrazine (or a reducing agent) to remove the phthalimide group (or reduce the azide group) to obtain an amine compound of the formula 13, reacting a compound of the formula 10 to the compound 13 to obtain a compound of the formula 14, reacting a carboxylic acid of the formula (III) or its reactive derivative to the compound, and then selectively removing the protecting groups represented by $R^{p3}$ and $R^{p4}$.

Removal of these protecting groups is carried out usually preferably in a solvent such as water-containing methanol, water-containing ethanol or water-containing tetrahydrofuran, in the presence of an acid such as hydrochloric acid, sulfuric acid or p-toluenesulfonic acid.

The reaction temperature is usually from −20° C. to 100° C., preferably from 0° C. to 50° C., and the reaction time is usually from 5 minutes to 48 hours, preferably from 10 minutes to 24 hours.

The step of producing a compound of the formula 12 from a compound of the formula 3, can be carried out in the same manner as the step of producing the compound of the formula 5 from the compound of the formula 3 in the above process A. Accordingly, with respect to the reaction conditions, etc., similar conditions may be employed.

The step of reducing the compound of the formula 12 can be carried out in the same manner as the step of producing the compound of the formula 7 from the ketone compound 5 in the above process B. Accordingly, with respect to the reaction conditions, etc., similar conditions may be employed.

The step of producing a compound of the formula 13 by aminating the reduced product obtained in the above step, can be carried out in the same manner as in the step of producing the amine compound of the formula 8 from the alcohol compound of the formula 7 in the above process C. Accordingly, with respect to the reaction conditions, etc., similar conditions may be employed.

The step of producing a compound of the formula 14 from the compound of the formula 13, can be carried out in the same manner as in the step of producing a compound of the formula (II-1) from the amine compound of the formula 8 in the above process D. Accordingly, with respect to the reaction conditions, etc., similar conditions may be employed.

The step of reacting the compound of the formula 14 with the compound of the formula (III), can be carried out in the same manner as in the step of reacting the compound of the formula (II) with the compound of the formula (III) in the above Process 1. Accordingly, with respect to the reaction conditions, etc., similar conditions may be employed.

Further, the compound of the formula 11 may be commercially available, or may be produced by a proper combination, as the case requires, of the methods disclosed in Reference Examples, or conventional methods or methods similar thereto.

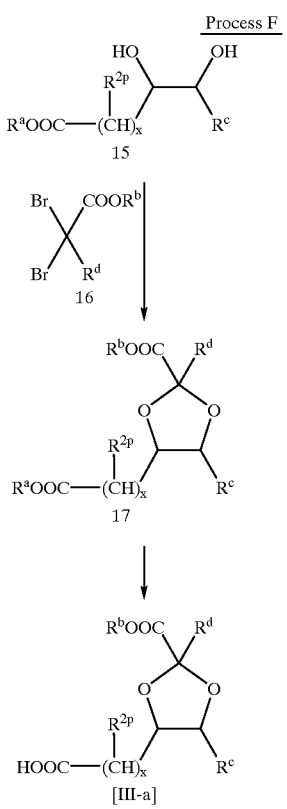

Process F

In the above formulas, $R^a$ is a tert-butyl group, a benzyl group, a benzhydryl group or a trityl group; $R^b$ is a lower alkyl group; each of $R^c$ and $R^d$ which are the same or different, is a hydrogen atom, a lower alkyl group or a lower alkoxycarbonyl group; and $R^{2p}$ and x are as defined above.

Process F is a synthesis for producing a carboxylic acid derivative of the formula (III-a) among compounds of the above formula (III).

According to this process, the desired carboxylic acid derivative (III-a) can be produced by reacting a dibromo compound of the formula 16 to a diol-compound of the formula 15 in the presence of a base to obtain a cyclic compound 17 and removing a carboxyl-protecting group $R^a$ under a mild condition.

The carboxyl-protecting group $R^a$ is preferably one which can readily be removed under a mild condition such as a weakly acidic condition or catalytic reduction, such as a tert-butyl group, a benzyl group, a benzhydryl group or a trityl group.

$R^b$ is preferably a lower alkyl group such as a methyl group or an ethyl group.

The lower alkoxycarbonyl group for $R^c$ and $R^d$ is preferably, for example, a methoxycarbonyl group or an ethoxycarbonyl group.

The step of producing the cyclic compound 17 from the diol compound of the formula 15, can be carried out by reacting 1 mol or an excess molar amount, preferably from 1 to 5 mols, of the dibromo compound of the formula 16 to one mol of the compound of the formula 15 usually in an inert solvent which gives no adverse effect to the reaction, in the presence of a base.

Such an inert solvent may, for example, be an ether such as ethyl ether, tetrahydrofuran, dimethoxyethane or dioxane; an aromatic hydrocarbon such as benzene or toluene; an aprotic polar solvent such as dimethylformamide or acetonitrile, or a mixture of such solvents.

The base may, for example, be an inorganic base such as sodium hydroxide, potassium hydroxide, sodium hydride or potassium hydride, or an organic base such as triethylamine, N-ethyldiisopropylamine or pyridine. Among them, sodium hydride or potassium hydride is, for example, preferred.

The base is used usually in an amount of 1 mol or an excess molar amount, preferably from 1 to 5 mols, per mol of the diol compound of the formula 15.

The reaction temperature is usually from −70° C. to the boiling point of the solvent used for the reaction, preferably from 0° C. to 120° C.

The reaction time is usually from 5 minutes to 7 days, preferably from 10 minutes to 24 hours.

For the step of selectively removing the protecting group represented by $R^a$ from the compound obtained by the above step, various methods are suitably selected depending upon the type and characteristics of the protecting group. Namely, the protecting group can selectively be removed by a common means such as hydrolysis by means of an acid or a base or reduction by utilizing the difference in stability against an acid, a base or reduction between $R^a$ and other protecting group $R^b$. With respect to specific methods for these reactions the methods disclosed in literatures, such as "Protective Groups in Organic Synthesis, T. W. Greene, John Wiley & Sons (1981)", or methods similar thereto, may, for example, be employed.

Further, the compound of the formula 15 may be commercially available, or may be produced by a proper combination, as the case requires, of the methods disclosed in Reference Examples or conventional methods, or methods similar thereto.

Process G

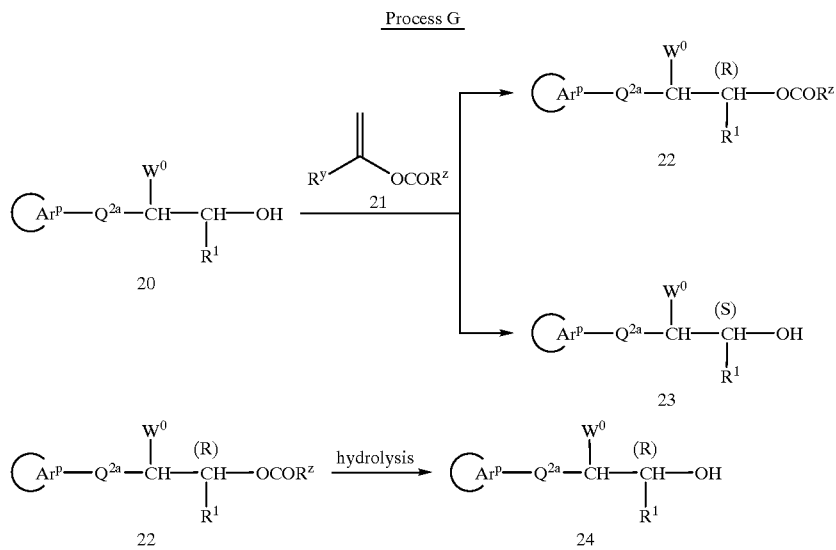

In the above formulas, $R^y$ is a hydrogen atom or a methyl group; $R^z$ is a lower alkyl group, an aryl group or an aralkyl group; $W^0$ is

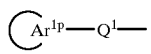

(wherein

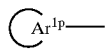

and $Q^1$ are as defined above) or

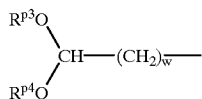

(wherein $R^{p3}$, $R^{p4}$ and w are as defined above); and

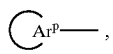

$Q^{2a}$ and $R^1$ are as defined above.

Process G is a process for preparing an optically active substance 23 or 24 of an alcohol compound 20 obtainable as a compound of the above formula 7 or a reduction product of the above formula 12.

According to this process, the desired optically active alcohol compounds 23 and 24 can be prepared by reacting a vinyl ester derivative of the formula 21 to a racemic alcohol derivative of the formula 20 in the presence of a lipase, separating the obtained optically active ester derivative 22 and the optically active alcohol derivative, and then hydrolyzing the ester group with respect to the optically active ester derivative 22.

$R^z$ of the vinyl ester derivative of the formula 21 is preferably a lower alkyl group such as a methyl group or an ethyl group; an aryl group such as a phenyl group or a naphthyl group; or an aralkyl group such as a benzyl group or a 2-phenylethyl group. Particularly preferred is a methyl group, i.e. a case wherein the compound of the formula 21 is vinyl acetate or isopropenyl acetate.

The above optical resolution reaction by lipase can be conducted usually in an inert solvent such as methylene chloride, chloroform, ethyl ether, tetrahydrofuran, benzene, toluene, hexane, heptane or acetonitrile, or by using the starting material vinyl ester derivative of the formula 21 itself as the solvent.

The vinyl ester derivative 21 is used usually in an amount of 1 mol or in a large excess molar amount, preferably from 1 to 100 mols, per mol of the starting material compound 20, and the amount of the lipase as the catalyst is from 0.01 to 100%, preferably from 0.1 to 20%, by weight, relative to the compound 20.

The type of the lipase is preferably a lipase derivative from Pseudomonas sp. such as Toyothium LIP™ (manufactured by Toyobo).

Further, the above enzymatic reaction tends to be accelerated, when the reaction is carried out in the presence of a base. As a base to be used for this purpose, an organic base such as triethylamine or diisopropylethylamine, is preferred.

The base is used usually in an amount of 0.01 mol or a slightly excess molar amount, preferably from 0.1 to 1.5 mols, relative to the starting material compound 20.

The reaction temperature is usually from 0° C. to 50° C., preferably from room temperature to 40° C. The reaction time is usually from 30 minutes to 7 days, preferably from 1 hour to 48 hours.

The hydrolytic reaction of the ester of the formula 22 can be conducted by a common method well known in the organic synthetic chemistry under an acidic or basic condition.

Process H

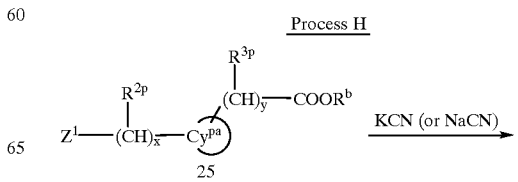

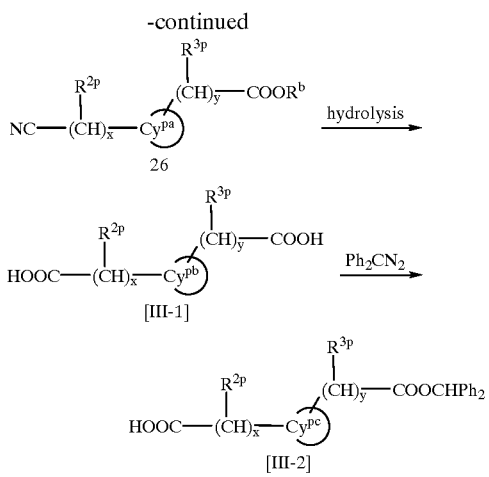

In the above formulas,

is an aryl group, a heteroaromatic ring or an aliphatic ring group which may contain one or two oxygen atoms, which may have substituent(s) selected from the group consisting of a lower alkoxycarbonyl group, a nitro group, a lower alkylcarbamoyl group, a lower carbamoyloxyalkyl group, a lower alkylcarbamoyloxyalkyl group, a lower alkyl group, a lower fluoroalkyl group, a lower alkoxy group, a lower alkoxyalkyl group, and hydroxyl, carbamoyl and lower hydroxyalkyl groups which may be protected;

is an aryl group, a heteroaromatic ring or an aliphatic ring group which may contain one or two oxygen atoms, which may have substituent(s) selected from the group consisting of a carboxyl group, a nitro group, a lower alkylcarbamoyl group, a lower carbamoyloxyalkyl group, a lower alkylcarbamoyloxyalkyl group, a lower alkyl group, a lower fluoroalkyl group, a lower alkoxy group, a lower alkoxyalkyl group, and hydroxyl, carbamoyl and lower hydroxyalkyl groups which may be protected;

is an aryl group, a heteroaromatic ring or an aliphatic ring group which may contain one or two oxygen atoms, which may have substituent(s) selected from the group consisting of a diphenylmethyloxycarbonyl group, a nitro group, a lower alkylcarbamoyl group, a lower carbamoyloxyalkyl group, a lower alkylcarbamoyloxyalkyl group, a lower alkyl group, a lower fluoroalkyl group, a lower alkoxy group, a lower alkoxyalkyl group, and hydroxyl, carbamoyl and lower hydroxyalkyl groups which may be protected; Ph is a phenyl group; and $Z^1$, $R^b$, $R^{2p}$, $R^{3p}$, x and y are as defined above.

According to this process, the desired compound (III-1) can be produced by reacting potassium cyanide or sodium cyanide to a compound 25 having a leaving group to obtain a nitrile derivative 26, and then hydrolyzing the nitrile compound 26 under an acidic or basic condition. Another desired compound i.e. the benzhydryl protected product (III-2) of the carboxylic acid, can be produced by treating the carboxylic acid (III-1) obtained as described above, with diphenyldiazomethane.

The above reaction steps will be described in detail referring to suitable reaction conditions.

The first step i.e. the reaction of reacting potassium cyanide or sodium cyanide to the compound 25 having a leaving group, can be carried out usually be using 1 mol or an excess molar amount, preferably from 1 to 5 mols, of potassium cyanide or sodium cyanide, per mol of the compound 2 having a leaving group in an inert solvent such as methanol, ethanol or dimethylformamide.

The reaction temperature is usually from 0° C. to the boiling point of the solvent used for the reaction, preferably from room temperature to 100° C., and the reaction time is usually from 10 minutes to 48 hours, preferably from 30 minutes to 24 hours.

The step of hydrolyzing the nitrile compound 26 obtained as described above to produce the desired carboxylic acid (III-1), can be carried out usually be using an acid such as hydrochloric acid, sulfuric acid or nitric acid, or a base such as sodium hydroxide or potassium hydroxide, in an inert solvent which gives no adverse effect to the reaction.

The acid and the base are usually preferably employed in their excess amounts.

Whether the condition is under acidic or basic, the inert solvent is preferably an alcohol such as methanol, ethanol, propanol, butanol or tert-butanol, or water, or a mixed solvent thereof.

The reaction temperature is usually from room temperature to the boiling point of the solvent used for the reaction, preferably from 50° C. to 150° C., and the reaction time is usually from 30 minutes to 72 hours, preferably from 1 to 48 hours.

Next, the step of treating the caroboxylic acid (III-1) with diphenyldiazomethane to obtain another desired compound i.e. the benzhydryl protected compound (III-2) of the carboxylic acid, can be carried out usually by using a limited amount of diphenyldiazomethane in an inert solvent which gives no adverse effect to the reaction.

This reaction can be regarded as a partial (selective) esterification reaction by diphenyldiazomethane of two or three carboxyl groups present in the molecule of the starting material carboxylic acid (III-1). Accordingly, along with the object, diphenyldiazomethane is used usually in its limited amount. Namely, when two carboxyl groups are present in the molecule of the starting material carboxylic acid (III-1), it is preferred to use from 1 to 1.5 mols of diphenyldiazomethane relative to 1 mol of the carboxylic acid (III-1), and when three carboxyl groups are present in the molecule of the starting material carboxylic acid (III-1), it is preferred to use from 2 to 3 mols of diphenyldiazomethane relative to 1 mol of the carboxylic acid (III-1).

The inert solvent used for the reaction, may, for example, be an ether such as tetrahydrofuran or dioxane; a halogenated hydrocarbon such as methylene chloride or chloroform; an aromatic hydrocarbon such as benzene or toluene; or acetone or ethyl acetate.

The reaction temperature is usually 0° C. to 40° C., and the reaction time is usually from 30 minutes to 24 hours.

Further, by using various protecting reagents for a carboxyl groups instead of diphenyldiazomethane, it is possible to produce various desired protected compounds.

Further, the compound of the formula 25 may be commercially available or can be produced by a proper combination, as the case requires, for the methods disclosed in Reference Example or conventional methods, or methods similar thereto.

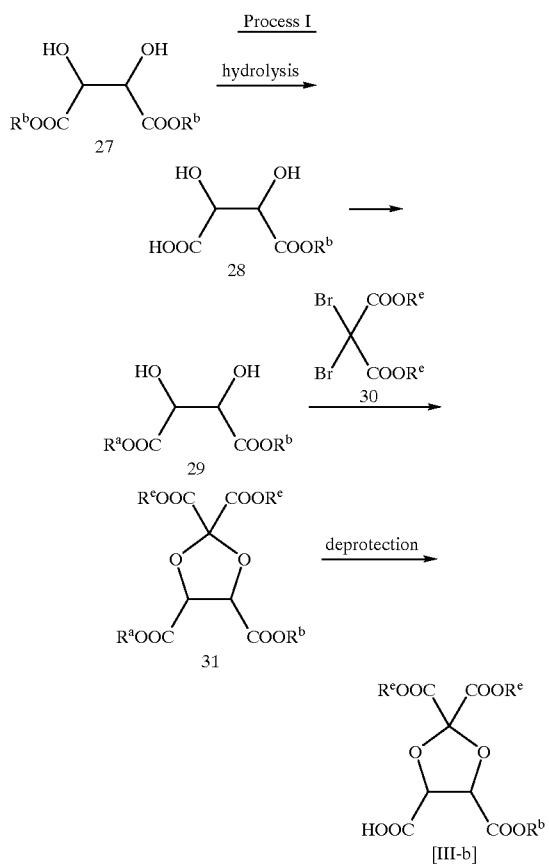

In the above formulas, $R^e$ is a lower alkyl group or a 2-(trimethylsilyl)ethyl group, or two $R^e$ bond to each other to form an isopropylidene group; and $R^a$ and $R^b$ are as defined above.

Process I is a process for producing a carboxylic acid derivative of the formula (III-b), among the compounds of the above formula (III).

According to this process, the desired carboxylic acid derivative (III-b) can be produced by hydrolyzing a lower alkyl ester derivative of D- or L-, or mesotartaric acid, of the formula 27 to obtain a corresponding monocarboxylic acid derivative, introducing a carboxyl-protecting group $R^a$ which can readily be removed, then reacting a dibromomalonic acid derivative of the formula 30 in the presence of a base to obtain a cyclic compound 31, and removing the carboxyl-protecting group $R^a$ under a mild condition.

The carboxyl-protecting group for $R^b$ or $R^e$ may, for example, be preferably a lower alkyl group such as a methyl group or an ethyl group.

The carboxyl-protecting group $R^a$ is preferably one which can readily be removed under a mild condition such as a weakly acidic condition or catalytic reduction, such as a tert-butyl group, a benzyl group, a benzhydryl group or a trityl group.

The mono-hydrolysis reaction of the ester compound of the formula 27 can be carried out usually by reacting 1 mol or a slightly excess molar amount, preferably from 1 to 1.5 mols, of the base, to one mol of the compound of the formula 27 in an inert solvent such as tetrahydrofuran, methanol or ethanol, or a mixed solvent thereof with water, in the presence of a base such as sodium hydroxide, potassium hydroxide or lithium hydroxide.

The reaction temperature is from −100° C. to 100° C., preferably from 0° C. to 50° C., and the reaction time is usually from 5 minutes to 48 hours, preferably from 8 hours to 24 hours.

The step of introducing the protecting group $R^a$ to the monocarboxylic acid derivative 28 obtained as described above, can be carried out usually by reacting an esterifying agent such as diphenyldiazomethane, N,N'-diisopropyl-O-benzylisourea or N,N'-diisopropyl-O-tert-butylisourea in an amount of 1 mol or an excess molar amount, preferably from 1 to 5 mols, per mol of the compound of the formula 28 in an inert solvent which gives no adverse effect to the reaction, thereby to obtain a diester compound of the formula 29.

As the inert solvent, methanol, ethanol, tetrahydrofuran, dioxane, acetone, dimethylformamide, methylene chloride, chloroform or ethyl acetate, may, for example, be used.

The reaction temperature is usually from room temperature to the boiling point of the solvent used for the reaction, and the reaction time is usually from 5 minutes to 7 days, preferably from 1 hour to 3 days.

The compound of the formula 29 can also be produced by introducing the protecting group $R^a$ to one of carboxyl groups of D- or L-, or mesotartaric acid and then introducing the protecting group $R^b$ to the other carboxyl group.

The step of producing the compound of the formula 31 from the compound of the formula 29 can be carried out under the same condition as the method disclosed in a literature (see U.S. Pat. No. 3,855,248).

For the step of selectively removing the protecting group represented by $R^a$ from the compound obtained in the above step, various methods may suitably be selected depending upon the type and characteristics of the protecting group. Namely, utilizing the difference in stability against an acid, a base or reduction between $R^a$ and other protecting groups $R^b$ and $R^e$, the protecting group can selectively be removed by a conventional means such as reduction or hydrolysis by means of an acid or a base. With respect to the specific methods for such reactions, the methods disclosed in a literature such as "Protective Groups in Organic Synthesis, T. W. Greene, John Wiley & Sons (1981)", or methods similar thereto, may, for example, be used.

Further, the compound of the formula 27 may be commercially available, or may be produced by a proper combination, as the case requires, of the methods disclosed in Reference Examples or conventional methods, or methods similar thereto.

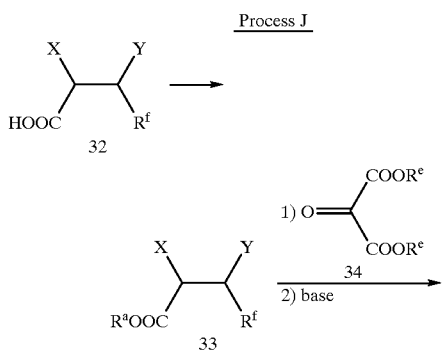

-continued

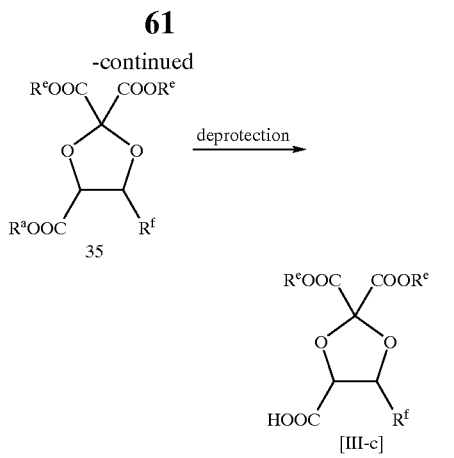

In the above formulas, $R^f$ is a hydrogen atom, a lower alkyl group, an aryl group or a heteroaromatic ring group; each of x and y which are different, is a halogen atom or a hydroxyl group; and $R^a$ and $R^e$ are as defined above.

Process J is a process for producing a carboxylic acid derivative of the formula (III-c) among compounds of the above formula (III).

According to this process, the desired carboxylic acid derivative (III-c) can be produced by introducing a carboxyl-protecting group $R^a$ which can easily be removed, to a halohydroxycarboxylic acid derivative of the formula 32, then mixing this with a ketomalonic acid derivative of the formula 34 to form a hemiketal, further reacting it in the presence of a base to form a cyclic compound 35, and removing the carboxyl-protecting group $R^a$ under a mild condition.

The carboxyl-protecting group for $R^e$ is preferably a lower alkyl group such as a methyl group or an ethyl group.

The carboxyl-protecting group $R^a$ is preferably one which can easily be removed under a mild condition such as a weakly acidic condition or catalytic reduction, such as a tert-butyl group, a benzyl group, a benzhydryl group or a trityl group.

The step of introducing the protecting group $R^a$ to the carboxylic acid derivative of the formula 32, can be carried out, for example, by reacting an esterifying agent such as diphenyldiazomethane, N,N'-diisopropyl-O-benzylisourea or N,N'-diisopropyl-O-tert-butylisourea in an amount of 1 mol or an excess molar amount, preferably from 1 to 5 mols, to 1 mol of the compound of the formula 32, in an inert solvent which gives no adverse effect to the reaction, to obtain a compound of the formula 33.

As the inert solvent, methanol, ethanol, tetrahydrofuran, dioxane, acetone, dimethylformamide, methylene chloride, chloroform or ethyl acetate may, for example, be used.

The reaction temperature is usually from room temperature to the boiling point of the solvent used for the reaction, and the reaction time is usually from 5 minutes to 7 days, preferably from 1 hour to 3 days.

The step of producing the compound of the formula 35 from the compound of the formula 33, can be carried out under the same condition as the method disclosed in a literature (see U.S. Pat. No. 4,182,718).

For the step of selectively removing the protecting group represented by $R^a$ from the compound obtained in the above step, various methods may suitably be selected depending upon the type and characteristics of the protecting group. Namely, by utilizing the difference in stability against an acid, a base or reduction between $R^a$ and other protecting group $R^e$, the protecting group can selectively be removed by a conventional means such as reduction or hydrolysis by means of an acid or a base. With respect to specific methods for these reactions, the methods disclosed in a literature "Protective Groups in Organic Synthesis, T. W. Greene, John Wiley & Sons (1981)", or methods similar thereto, can be used.

Further, the compound of the formula 32 may be commercially available, or may be produced by a proper combination, as the case requires, of the methods disclosed in Reference Examples or conventional methods, or methods similar thereto. With respect to such specific methods, the methods disclosed in a literature "J. Med. Chem., 1985, No. 28, p. 463–477" or methods similar thereto may be used by using e.g. a commercially available α-amino acid as the starting material.

Process K

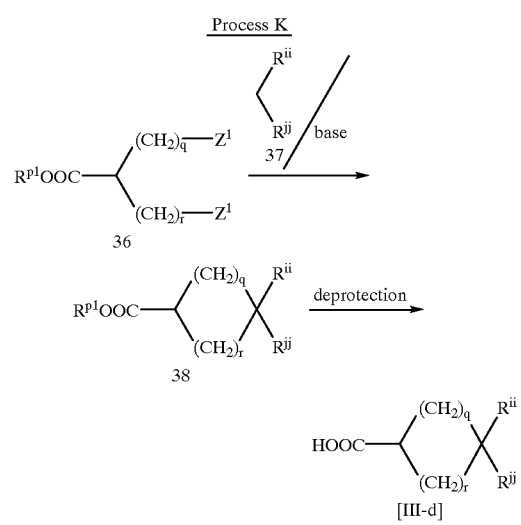

In the above formulas, each of q and r which are the same or different, is an integer of from 0 to 5; each of $R^{ii}$ and $R^{jj}$ which are the same or different, is a lower alkoxysulfonyl group, a sulfamoyl group, a lower alkylsulfamoyl group, a group of the formula $-PO(OR^{4p})(OR^{5p})$, or a carboxyl group which may be protected (provided that the sum of q and r is from 1 to 5, and the methylene group not adjacent to $Z^1$ may be replaced by an oxygen atom to have an ether structure); and $R^{4p}$, $R^{5p}$, $R^{p1}$ and $Z^1$ are as defined above.

Process K is a process for producing a carboxylic acid derivative of the formula (III-d) among compounds of the above formula (III).

According to this process, the desired carboxylic acid derivative (III-d) can be produced by reacting a compound of the formula 37 to the compound of the formula 36 in the presence of a base to obtain a compound of the formula 38, and removing the carboxyl-protecting group $R^{p1}$.

The step of producing the compound of the formula 38 from the compound of the formula 36, can be carried out by reacting the compound of the formula 37 in an amount of 1 mol or an excess molar amount, preferably from 1 to 2 mols, to 1 mol of the compound of the formula 36, in an inert solvent which gives no adverse effect to the reaction in the presence of a base.

Such an inert solvent may, for example, be an ether such as ethyl ether, tetrahydrofuran or dioxane; an aromatic hydrocarbon such as benzene, toluene or xylene; an aprotic polar solvent such as dimethylformamide, dimethyl sulfoxide or hexamethylphosphoric triamide, or a mixture of such solvents.

The base to be used for this reaction, may, for example, be an alkali metal hydride such as sodium hydride, lithium hydride or potassium hydride; a lithium amide such as lithium amide, lithium diisopropyl amide or lithium bistrimethylsilylamide; an alkali metal alkoxide such as sodium methoxide, sodium ethoxide or potassium tert-butoxide; or an alkali metal hydroxide such as sodium hydroxide, potassium hydroxide or lithium hydroxide.

Such a base is used in an amount of 1 mol or an excess molar amount, preferably from 1 to 5 mols, per mol of the compound of the formula 36 as the starting material.

The reaction temperature is usually from −100° C. to the boiling point of the solvent used for the reaction, preferably from −80° C. to 100° C., and the reaction time is usually from 10 minutes to 48 hours, preferably from 30 minutes to 24 hours.

For the step of selectively removing the protecting group represented by $R^{p1}$ from the compound obtained in the above step, various methods may suitably be selected depending upon the type and characteristics of the protecting group. Namely, by utilizing the difference in stability against an acid, a base or reduction between $R^{p1}$ and other protecting groups, the protecting group can selectively be removed by a conventional means such as reduction or hydrolysis by means of an acid or a base. With respect to specific methods for these reactions, the methods disclosed in a literature, such as "Protective Groups in Organic Synthesis, T. W. Greene, John Wiley & Sons (1981)", or the methods similar thereto, may be used.

Further, the compound of the formula 36 or 37 may be a commercial product, or can be produced by a proper combination, as the case requires, of the methods of Reference Examples or conventional methods, or methods similar thereto.

A compound of the formula (II'-a):

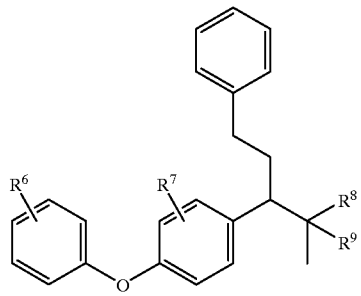

[II'-a]

wherein each of $R^6$ and $R^7$ which are the same or different, is a hydrogen atom, a halogen atom, a lower alkoxy group or an aralkyloxy group; $R^8$ is a hydrogen atom, $R^9$ is a hydroxy group, an amino group or a group of the formula —$OCOR^8$ or —$NHCH_2COOR^{p1}$, or $R^8$ and $R^9$ together form an oxo group; $R^z$ is a lower alkyl group, an aryl group or an aralkyl group; and $R^{p1}$ is a hydrogen atom or a protecting group for a carboxyl group, and a compound of the formula (III'-bb):

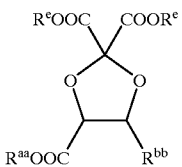

[III'-bb]

wherein $R^{aa}$ is a hydrogen atom, a tert-butyl group, a benzyl group, a benzhydryl group or a trityl group; $R^{bb}$ is a hydrogen atom, a lower alkyl group, an aryl group, a heteroaromatic ring group or a group of the formula —$COOR^b$; $R^b$ is a lower alkyl group; $R^e$ is a lower alkyl group or a 2-(trimethylsilyl)ethyl group, or two $R^e$ bond to each other to form an isopropylidene group, are important intermediates for producing the compound of the formula (I) and novel compounds not disclosed in literatures.

The present invention relates also to the compound of the formula (II'-a) and the compound of the formula (III'-bb).

In the formula (II'-a), each of $R^6$ and $R^7$ which are the same or different, is a hydrogen atom, a halogen atom, a lower alkoxy group or an aralkyloxy group, but a hydrogen atom, a chlorine atom, a bromine atom, a methoxy group, an ethoxy group or a benzyloxy group, is, for example, preferred.

$R^6$ and $R^7$ may, respectively, be substituted at optional positions for substitution on the respective benzene rings.

$R^8$ is a hydrogen atom, $R^9$ is an hydroxyl group, an amino group or a group of the formula —$OCOR^z$ or —$NHCH_2COOR^{p1}$, or $R^8$ and $R^9$ together form an oxo group.

$R^z$ is a lower alkyl group, an aryl group or an aralkyl group, but a methyl group, an ethyl group, a phenyl group, a naphthyl group, a benzyl group or a 2-phenylethyl group, is, for example, preferred.

$R^{p1}$ is a hydrogen atom or a protecting group for a carboxyl group, but a protecting group for a carboxyl group, such as a methyl group, an ethyl group, a tert-butyl group or a benzyl group, is, for example, preferred.

Among compounds of the formula (II'-a), a compound wherein $R^8$ is a hydrogen atom and $R^9$ is a group of the formula —$NHCH_2COOR^{p1}$ (wherein $R^{p1}$ is as defined above), is a compound covered by the compound of the above formula (II). Accordingly, the desired compound of the formula (I) can be produced by reacting such a compound with a carboxylic acid of the formula (III) or its reactive derivative, in accordance with the above Process 1.

In the formula (III'-bb), $R^{aa}$ is a hydrogen atom, a tert-butyl group, a benzyl group, a benzhydryl group or a trityl group.

$R^{bb}$ is a hydrogen atom, a lower alkyl group, an aryl group, a heteroaromatic ring group or a group of the formula —$COOR^b$, but a hydrogen atom or a group of the formula —$COOR^b$ is, for example, preferred.

$R^b$ is a lower alkyl group, but a methyl group, an ethyl group or a tert-butyl group, is, for example, preferred.

$R^e$ is a lower alkyl group or a 2-(trimethylsilyl)ethyl group, or two $R^e$ bond to each other to form an isopropylidene group. As the lower alkyl group, a methyl group, an ethyl group or a tert-butyl group, is, for example, preferred.

Among compounds of the formula (III'-bb), a compound wherein $R^{aa}$ is a hydrogen atom, is a compound covered by the compound of the above formula (III). Accordingly, the desired compound of the formula (I) can be produced by reacting such a compound or its reactive derivative with the compound of the formula (II) in accordance with the above Process 1.

Pharmacological Test 1 (Inhibitory Activities Against Protein-farnesyl Transferase)

To demonstrate the usefulness of the present invention, 50% inhibitory concentrations ($IC_{50}$ values) of the compounds of the present invention against the protein-farnesyl transferase (PFT) activities, were obtained.

(1) Preparation of PFT

PFT was separated in such a manner that a soluble fraction of rat's brain was fractionated by means of 30%–50% saturated ammonium sulfate, further dialyzed and then subjected to column chromatography by Q-cephalose™ (manufactured by Pharmacia) (Reiss et al, Cell, vol. 62, p. 81–88 (1990)).

(2) Method for measuring PFT activities

Measurement of PFT activities was conducted by using, as a prenyl acceptor, H-ras protein or a substance that biotin was added to N-terminal of a peptide corresponding to a 7 amino acid residue at C terminal of K-rasB protein (biotin-added Lys-Thr-Ser-Cys-Val-Ile-Met) and, as a prenyl donor, [$^3$H]-labeled farnesylpyrophosphate (FPP) (Reiss et al, Methods: A Companion to a Methods in Enzymology, vol. 1, No. 3, p. 241–245 (1990)).

The [$^3$H]-labeled farnesylpyrophosphate (22.5 Ci/mmol) was purchased from New England Nuclear Co. Non-labeled farnesylpyrophosphate was chemically synthesized from ditriethylammonium phosphate, trans-trans-farnesol and trichloroacetonitrile and purified by XAD-2-resin column and diethylaminoethylcellulose (Cornforth et al, Methods in Enzymology, vol. 15, p. 385–390 (1969)).

H-ras protein was expressed in *Escherichia coli* and purified (Gibbs et al, Proc. Natl. Acad. Sci., vol. 81, p. 5704–5708 (1984)).

The PFT reaction solution containing H-ras protein as the prenyl acceptor was 25 μl, and its composition was 50 mM Hepes pH7.5/50 μM $ZnCl_2$/5 mM $MgCl_2$/20 mM KCl/5 mM DTT/0.6 μM all trans [$^3$H]-farnesylpyrophosphate/25 μM H-ras protein/PFT derived from rat brain (Q-sephalose fraction). The reaction temperature was 37° C., the preincubation time was 10 minutes, and the reaction time was 20 minutes.

The PFT reaction solution containing biotin-added Lys-Thr-Ser-Cys-Val-Ile-Met as the prenyl acceptor, was 25 μl, and its composition was 50 mM tris-Cl pH7.5/50 μM $ZnCl_2$/5 mM $MgCl_2$/20 mM KCl/1 mM DTT/0.2% n-octyl-β-D-glucopyranoside/0.6 μM all trans [$^3$H]-farnesylpyrophosphate/3.6 μM biotin-added Lys-Thr-Ser-Cys-Val-Ile-Met/PFT derived from rat brain (Q-sephalose fraction). The reaction temperature was 37° C., the preincubation time was 10 minutes, and the reaction time was 20 minutes.

The enzymatic reaction product containing H-ras protein as the prenyl acceptor, was analyzed by SDS-PAGE (sodium dodecylsulfate/polyacrylamide gel electrophoresis). The [$^3$H]-labeled enzymatic reaction product was boiled for 3 minutes in a buffer solution containing 2% SDS/50 mM Tris-Cl pH6.8/10% sucrose/5% 2-mercaptoethanol, then subjected to electrophoresis with a slab gel of 12% polyacrylamide, whereby the [$^3$H]-labeled H-ras protein was fluorography-enhanced by EN$^3$HANCE™ (manufactured by New England Nuclear Co.) and then visualized by autoradiography (James et al, Science, vol. 260, No. 25, p. 1937–1942 (1993)).

The measurement of PFT activities using H-ras protein as the prenyl receptor, was also analyzed by a rapid separate method. The mixed solution for measurement wherein no prenyl donor was present, was preincubated, and a prenyl group transferring reaction was initiated by an addition of [$^3$H]-FPP and terminated at an appropriate time by an addition of 0.5 ml of 4% SDS. Further, 0.5 ml of 30% trichloroacetic acid was added thereto and thoroughly mixed. Then, the reaction solution was left to stand at 4° C. for 60 minutes to let H-ras protein precipitate. This reaction solution was subjected to filtration under reduced pressure by Whatman GF/B filter. The filter was washed 6 times with 2 ml of 6% trichloroacetic acid, and mixed with 8 ml of scintillation cocktail (Clearsol I™, manufactured by Nacalai Tesque Co.). Then, counting was carried out by a Beckmann TRI-CARB2500TR scintillation counter.

Measurement of PFT activities was also carried out by using biotin-added Lys-Thr-Ser-Cys-Val-Ile-Met as the prenyl acceptor. The mixed solution for measurement containing biotin-added Lys-Thr-Ser-Cys-Val-Ile-Met as the prenyl acceptor and containing no prenyl donor, was preliminarily thermally equilibrated, and then a prenyl group transferring reaction was initiated by an addition of [$^3$H]-FPP and terminated at an appropriate time by an addition of 0.2 ml of 2 mg/ml bovine serum albumin/2% sodium dodecylsulfate/150 mM NaCl. Further, 0.02 ml of avidin agarose (Pierce) was added thereto, and the mixture was shaked for 30 minutes to let the [$^3$H]-farnesyl group-transferred biotin-added Lys-Thr-Ser-Cys-Val-Ile-Met sufficiently bond to the avidin agarose. Then, avidin agarose was washed four times with 1 ml of 2 mg/ml bovin serum albumin (BSA)/4% sodium dodecylsulfate/150 mM NaCl, and mixed with 1 ml of scintillation cocktail (Clearsol™, manufactured by Nacalai Tesque). Then, counting was carried out by a Beckmann TRI-CARB2500TR scintillation counter.

The biotin-added Lys-Thr-Ser-Cys-Val-Ile-Met heptapeptide used as an artificial substrate, was synthesized in a solid phase by an Applied biosystems model 431A peptide synthesizer, and an α-amino terminal of the solid phase Lys-Thr-Ser-Cys-Val-Ile-Met heptapeptide which was bound to a resin, was biotin-modified by N-hydroxysuccinimide biotin, then cut off from the resin and purified by reversed phase high performance liquid chromatography (HPLC).

The addition of the compound of the present invention to the PFT reaction system was carried out by preliminarily adding dimethyl sulfoxide in an amount of 1% by volume (0.25 μl) of the reaction solution.

The 50% inhibitory concentrations ($IC_{50}$ values) of the compounds of the present invention against PFT activities, are shown in Table 1.

TABLE 1

| 50% inhibitory concentrations against PFT activities | |
|---|---|
| Compound | $IC_{50}$ (nM) |
| Example 9 | 0.16 |
| Example 21 | 0.098 |
| Example 22 | 0.095 |
| Example 23 (4R*, 5S*)-isomer | 0.085 |
| Example 23 (4S*, 5R*)-isomer | 0.075 |
| Example 31 | 0.22 |
| Example 32 | 0.20 |

Pharmacological Test Example 2 (Inhibitory Activities Against Farnesyl-modification of Ras Protein)

Using the compounds of the present invention, inhibitory activities against farnesyl-modification of Ras protein in NIH3T3 cells transformed by activated ras gene, were measured.

The NIH3T3 cells transformed by activated ras gene, were seeded on a culture plate and cultured for 3 days. Then, a compound of the preset invention in a predetermined concentration was added to the culture. In accordance with the method disclosed in J. Biol. Chem., vol. 268, p. 18415 (1993), the cells were cultured for 24 hours and then taken off from the plate, and the cells were dissolved. After centrifugal separation for 5 minutes under 12000 g, the supernatant was used as a cell extract. The cell extract was subjected to SDS polyacrylamide gel electrophoresis to separate farnesyl-modified Ras protein and non-farnesyl-modified Ras protein. The protein on the gel was transferred onto a nitrocellulose membrane, and an anti-Ras protein antibody was reacted as a probe (primary antibody reaction). An anti-primary antibody, a peroxidase inclusion (secondary antibody), was reacted, and then Ras protein was detected by a chemical fluorescence enhancing kit. The proportion of non-farnesyl-modified Ras protein was quantified by a densitometer and taken as the inhibitory activity.

The 50% inhibitory concentrations ($IC_{50}$ values) of the compounds of the present invention against farnesyl-modification of Ras protein are shown in Table 2.

TABLE 2

| Compound | 50% inhibitory concentrations against farnesyl-modification of Ras protein $IC_{50}$ ($\mu M$) |
|---|---|
| Example 9 | 0.24 |
| Example 21 | 2.1 |
| Example 22 | 1.9 |
| Example 23 (4R*, 5S*)-isomer | 2.1 |
| Example 23 (4S*, 5R*)-isomer | 2.0 |
| Example 31 | 0.55 |
| Example 32 | 0.59 |

Pharmacological Test Example 3 (Therapeutic Effects to NIH3T3 Cells Transformed by Activated Ras Gene (NIH/ras))

The compounds of the present invention exhibit excellent antitumor effects, as shown by the following Pharmacological Test Example.

The antitumor effects of the compounds of the present invention against NIH/ras cells are shown in Tables 3 and 4.

TABLE 3

Effects of the compound of Example 9 against NIH/ras

| Tumor[1] | Dose[2] Intra-peritoneal (mg/kg/injection) | Weight of tumor[3] Average (g) ± standard deviation | Growth inhibition[4] (%) |
|---|---|---|---|
| NIH/ras | 0 | 0.073 ± 0.042 | 0 |
|  | 20 | 0.024 ± 0.018* | 67 |
|  | 40 | 0.015 ± 0.013** | 80 |
|  | 80 | 0.008 ± 0.006** | 90 |
|  | 160 | 0.002 ± 0.001** | 98 |

[1]Tumor inoculation: $10^6$ cells were inoculated subcutaneously to a female nude mouse.
[2]Dose: Each dose was intra-peritonealy administered once a day from the first day to the sixth day after the inoculation of the cells,.
[3]Weight of tumor: On the seventh day after inoculation of the cells, the tumors were weighed.
[4]Growth inhibition: (1-(average weight of tumor of the treated group/average weight of tumor of the control group)) × 100
* and **: Statistical analyses by u-test are 5% and 1%, respectively.

TABLE 4

Effects of the compound of Example 22 against NIH/ras

| Tumor[1] | Dose[2] Subcutaneous (mg/kg/injection) | Volume of tumor[3] Average ($cm^3$) ± standard deviation | Growth inhibition[4] (%) |
|---|---|---|---|
| NIH/ras | 0 | 0.652 ± 0.136** | 0 |
|  | 10 | 0.164 ± 0.073** | 75 |
|  | 20 | 0.052 ± 0.030** | 92 |
|  | 40 | 0.010 ± 0.009** | 99 |

[1]Tumor inoculation: $10^6$ cells were inoculated subcutaneously to a female nude mouse.
[2]Dose: Each dose was subcutaneously administered once a day from the first day to the tenth day after the inoculation of the cells.
[3]Volume of tumor: On the eighth day after inoculation of the cells, volume of the tumors were measured.
[4]Growth inhibition: (1-(average volume of tumor of the treated group/average volume of tumor of the control group)) × 100
**Statistical analysis by u-test was 1%.

From the forgoing results, the compounds of the present invention have excellent inhibitory activities against protein-farnesyl transferase (PFT) and thus useful as antitumor agents, for example, against colon cancers, pancreatic cancers, myloid leukemias, lung cancer, carcinoma cutaneum or thyroid gland cancer, particularly against pancreatic cancers.

Further, the protein-farnesyl transferase (PFT) inhibitor of the present invention is capable of inhibiting transfection of ras and capable of inhibiting reactivation of HIV gene transformed into the host cells, and thus is useful also as an anti-HIV agent.

The compound of the formula (I) of the present invention can be orally or parenterally administered, and it may be formulated into a formulation suitable for such administration, so that it can be used as an antitumor agent or an anti-HIV agent. To use the compound of the present invention for clinical purpose, it may be formulated into various formulations by an addition of pharmaceutically acceptable additives to meet the type of administration and then administered. As such additives, various additives which are commonly used in the field of drug formulations, may be used, including, for example, gelatin, lactose, saccharose, titanium oxide, starch, crystalline cellulose, hydroxypropylmethylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene hardened castor oil, polyvinylpyrrolidone, magnesium stearate, light silicic anhydride, talc, vegetable oil, benzyl alcohol, gum arabic, propylene glycol, polyalkylene glycol, cyclodextrin and hydroxypropylcyclodextrin, etc.

A drug formulation to be prepared as a mixture with such additives, may, for example, be a solid formulation such as a tablet, a capsule, a granule, a powder or a suppository; or a liquid formulation such as a syrup, an elixir or an injection drug. These formulations can be prepared in accordance with conventional methods commonly employed in the field of drug formulations. Further, in the case of a liquid formulation, it may be of the type which is to be dissolved or suspended in water or in other suitable medium at the time of its use. Particularly, in the case of an injection drug, it may be dissolved or suspended in a physiological saline or in a glucose solution, and a buffering agent or a preserving agent may further be added.

These formulations may contain the compound of the present invention in a proportion of from 1.0 to 100 wt %, preferably from 1.0 to 60 wt % of the total amount. These formulations may further contain therapeutically effective other compounds.

When the compound of the present invention is used as an antitumor agent or an anti-HIV agent, its dose and the frequency of administration vary depending upon the sex, the age, the body weight and the diseased degree of the patient and the type and the range of the intended treating effects. However, in the case of an oral administration, it is preferred to administer from 0.01 to 20 mg/kg per day for an adult all at once or in a few times in a divided fashion. In the case of parenteral administration, it is preferred to administer from 0.002 to 10 mg/kg per day for an adult all at once or in a few times in a divided fashion.

The therapeutically effective other compounds may, for example, be drugs which bring about a decrease of farnesyl pyrophosphate in vivo.

The drugs which bring about a decrease of farnesyl pyrophosphate in vivo, are not particularly limited so long as they are drugs having such activities and which are acceptable as pharmaceuticals. However, biosynthesis-inhibitors against farnesyl pyrophosphate are, for example, preferred. Among them, drugs which inhibit a biosynthesis process of farnesyl pyrophosphate, such as hydroxymethylglutaryl CoA synthase-inhibitors or hydroxymethylglutary CoA reductase-inhibitors represented by e.g. lovastatin, simvastatin, pravastatin and fluvastatin disclosed, for example, in Nature, vol. 343, p. 425–430 (1990), are preferred. Particularly preferred are hydroxymethylglutaryl CoA reductase-inhibitors such as lovastatin, simvastatin, pravastatin and fluvastatin.

The composition comprising the compound of the present invention and the above drug, can be formulated in the same manner as in the case where the compound of the present invention is used as a single drug. Such a formulation may contain the protein-farnesyl transferase inhibitor and the drug which brings about a decrease of a farnesyl pyrophosphate in vivo, as active ingredients, in an amount of from 1.0 to 100 wt %, preferably from 1.0 to 60 wt %, of the entire drug.

Further, the weight ratio of the protein-farnesyl transferase inhibitor and the drug which brings about a decrease of a farnesyl pyrophosphoric acid in vivo, may be from 0.001:1 to 1000:1. However, the weight ratio is particularly preferably from 0.01:1 to 100:1.

BEST MODE FOR CARRYING OUT THE INVENTION

Now, the present invention will be described in further detail with reference to Examples and Reference Examples, but the present invention is by no means restricted by such Examples.

EXAMPLE 1

Preparation of (2RS)-2-[N-(carboxymethyl)-N-{(1R,2R)-2-(2-fluoro-4-biphenylyl)-1-methyl-4-phenylbutyl}carbamoyl]cyclopropane- 1,1-dicarboxylic acid 73 mg of N-(tert-butoxycarbonylmethyl)-{(1R,2R)-2-(2-fluoro-4-biphenylyl)-1-methyl-4-phenylbutyl}amine obtained in Reference Example 1, 140 mg of 2,2-di-tert-butyl 1,2,2-cyclopropanetricarboxylate obtained in Reference Example 2 and 1.0 ml of triethylamine, were dissolved in 1 ml of chloroform, and a solution of 91 mg of 2-chloro-1,3-dimethylimidazolinium chloride in 1 ml of chloroform, was added under cooling with ice, followed by stirring at the same temperature for 20 minutes and then stirring at room temperature for two hours. The reaction solution was poured into water and extracted with ethyl acetate. The extract solution was washed with a saturated sodium chloride aqueous solution and then dried over anhydrous sodium sulfate. The drying agent was filtered off, and then, the solvent was distilled off under reduced pressure. The residue was purified by silica gel column chromatography (hexane/ethyl acetate=5/1), to obtain 114 mg (yield: 98%) of a tri-tert-butyl ester of the above identified compound as a colorless oily substance.

2 ml of formic acid was added to 78 mg of the above ester, followed by stirring at room temperature for 18 hours. The reaction solution was evaporated to dryness under reduced pressure to obtain 60 mg (yield: quantitative) of the above identified compound as a colorless oily substance.

$^1$H-NMR(CD$_3$OD) δ:0.80–1.05(3H, m), 1.50–1.90(2H, m), 2.00–3.40(6H, m), 3.60–4.60(3H, m), 6.95–7.50(13H, m).

FAB-MS:548(M+H).

EXAMPLE 2

Preparation of 4-[N-(carboxymethyl)-N-{(1R,2R)-2-(2-fluoro-4-biphenylyl)-1-methyl-4-phenylbutyl}carbamoylmethyl]phthalic acid The above identified compound was obtained by carrying out the same reaction as in Example 1 except that instead of 2,2-di-tert-butyl 1,2,2-cyclopropanetricarboxylate used as the starting material in Example 1, 3,4-bis (diphenylmethyloxycarbonyl)phenylacetic acid obtained in Reference Example 3, was used.

$^1$H-NMR(CD$_3$COCD$_3$) δ:0.85–1.00(3H, m), 1.75–3.00 (5H, m), 3.50–4.00(5H, m), 7.00–7.80(16H, m).

FAB-MS:598(M+H).

EXAMPLE 3

Preparation of 4-[N-(carboxymethyl)-N-{(1R,2R)-2-(2-fluoro-4-biphenylyl)-1-methyl-4-phenylbutyl}carbamoyl] phthalic acid 61 mg of N-(tert-butoxycarbonylmethyl)-{(1R,2R)-2-(2-fluoro-4-biphenylyl)-1-methyl-4-phenylbutyl}amine obtained in Reference Example 1, 39 mg of trimellitic anhydride and 85 μl of triethylamine, were dissolved in 3 ml of chloroform, and a solution of 91 mg of 2-chloro-1,3-dimethylimidazolinium chloride in 1 ml of chloroform, was added under cooling with ice, followed by stirring at room temperature for two hours. To the reaction solution, 1 ml of a saturated sodium hydrogen carbonate aqueous solution was added, followed by vigorously stirring at room temperature for one hour. Then, it was acidified with 1N hydrochloric acid and extracted with ethyl acetate. The extract solution was washed with a saturated sodium chloride aqueous solution and then dried over anhydrous sodium sulfate. The solvent was distilled off under reduced pressure. To the residue, 2 ml of trifluoroacetic acid was added, followed by stirring at room temperature for one hour. Then, the reaction solution was concentrated under reduced pressure. The residue was purified by medium pressure liquid chromatography (Lobar column™, Size A, RP-8, manufactured by Merck Co.; acetonitrile/0.1% trifluoroacetic acid aqueous solution=1/1), followed by treatment with chloroform-hexane to obtain 33 mg (yield: 42%) of the above identified compound as white powder.

$^1$H-NMR(CD$_3$COCD$_3$) δ:1.08(3H, d, J=6.3 Hz), 1.80–3.30(5H, m), 3.90–4.40(3H, m), 6.95–7.90(16H, m).

FAB-MS:584(M+H).

EXAMPLE 4

Preparation of 5-[N-(carboxymethyl)-N-{(1R,2R)-2-(2-fluoro-4-biphenylyl)-1-methyl-4-phenylbutyl}carbamoyl] isophthalic acid 72 mg of N-(methoxycarbonylmethyl)-{(1R,2R)-2-(2-fluoro-4-biphenylyl)-1-methyl-4-phenylbutyl}amine obtained in the same manner as in Reference Example 1, 50 mg of diethyl trimesate and 74 μl of triethylamine, were dissolved in 3 ml of chloroform, and a solution of 45 mg of 2-chloro-1,3-dimethylimidazolinium chloride in 1 ml of chloroform, was added under cooling with ice, followed by stirring at room temperature for 3 hours. The reaction solution was poured into water and extracted with ethyl acetate. The extract solution was dried over anhydrous magnesium sulfate. The drying agent was filtered off, and then the solvent was distilled off under reduced pressure. The residue was purified by silica gel column chromatography (hexane/ethyl acetate=3/1), to obtain 60 mg (yield: 51%) of a triester of the above identified compound as a colorless oily substance.

60 mg of the above ester was dissolved in 4 ml of a 50% tetrahydrofuran aqueous solution, and 115 mg of lithium hydroxide monohydrate was added, followed by stirring at room temperature for 18 hours. The reaction solution was acidified with 1N hydrochloric acid and then, extracted with ethyl ether. The organic layer was dried over anhydrous magnesium sulfate and then, the solvent was distilled off under reduced pressure. The residue was purified by medium pressure liquid chromatography (Lobar column™, Size A, RP-8, manufactured by Merck Co.; acetonitrile/0.1% trifluoroacetic acid aqueous solution=1/1), followed by treatment with chloroform-hexane to obtain 32 mg (yield: 60%) of the above identified compound as white solid.

$^1$H-NMR(CD$_3$COCD$_3$) δ:1.05–1.15(3H, m), 1.80–3.50 (5H, m), 3.90–4.42(3H, m), 6.95–7.65(13H, m), 8.49 and 8.53(total 2H, each s), 8.70 and 8.85(total 1H, each s).

FAB-MS:584(M+H).

EXAMPLE 5

Preparation of (4R,5R)-4-[N-(carboxymethyl)-N-{(1R,2R)-2-(2-fluoro-4-biphenylyl)-1-methyl-4-phenylbutyl}carbamoylmethyl]-2,2-dimethyl-1,3-dioxolane-4,5-dicarboxylic acid The above identified compound was obtained by carrying out the same reaction as in Example 4 except that instead of diethyl trimesate used as the starting material in Example 4, dimethyl 2-(carboxymethyl)-2,3-O-isopropylidene-L-tartarate obtained in Reference Example 4, was used.

$^1$H-NMR(CD$_3$COCD$_3$) δ:0.80–1.10(3H, m), 1.27, 1.41, 1.47 and 1.51(total 6H, each s), 1.80–3.20(7H, m), 3.50–4.05(3H, m), 4.85–5.00(1H, m), 7.00–7.60(13H, m).

FAB-MS:622(M+H).

EXAMPLE 6

Disodium (2R*,4S,5S)-5-[N-(carboxylatomethyl)-N-{(1R,2R)-2-(2-fluoro-4-biphenylyl)-1-methyl-4-phenylbutyl}carbamoyl]-2-ethoxy-1,3-dioxolane-4-carboxylate, and disodium (2S*,4S,5S)-5-[N-(carboxylatomethyl)-N-{(1R,2R)-2-(2-fluoro-4-biphenylyl)-1-methyl-4-phenylbutyl}carbamoyl]-2-ethoxy-1,3-dioxolane-4-carboxylate 166 mg of N-(methoxycarbonylmethyl)-{(1R,2R)-2-(2-fluoro-4-biphenylyl)-1-methyl-4-phenylbutyl}amine obtained in the same manner as in Reference Example 1, 107 mg of 4-methyl (2RS,4S,5S)-2-ethoxy-1,3-dioxolane-4,5-dicarboxylate and 200 μl of triethylamine, were dissolved in 7 ml of chloroform, and a solution of 45 mg of 2-chloro-1,3-dimethylimidazolinium chloride in 1 ml of chloroform, was added under cooling with ice, followed by stirring at room temperature for 15 hours. The reaction solution was poured into water and extracted with chloroform. The extract solution was washed with water, a saturated sodium hydrogen carbonate aqueous solution and a saturated sodium chloride aqueous solution and then, dried over anhydrous magnesium sulfate. The drying agent was filtered off, and then, the solvent was distilled off under reduced pressure. The residue was purified by silica gel thin layer chromatography (Kieselgel™60F$_{254}$, Art™5744; hexane/acetone=2/1), and then further, using silica gel thin layer chromatography (Kieselgel™60F$_{254}$, Art™5744; hexane/ethyl acetate=2/1), 77 mg (yield: 31%) of a dimethyl ester of the above identified compound named as (2R*)-isomer for the sake of convenience and 51 mg (yield: 21%) of a dimethyl ester of the above identified compound named as (2S*)-isomer were separated and obtained, respectively, as colorless foams.

13 mg and 12 mg of the above esters were, respectively, dissolved in 4 ml of 50% tetrahydrofuran aqueous solution separately, and 48 μl and 42 μl of sodium hydroxide aqueous solutions were added, followed by stirring at room temperature for 18 hours. The solvent was distilled off under reduced pressure to obtain 13 mg (yield: quantitative) of the above identified compound named as (2R*)-isomer for the sake of convenience and 12 mg (yield: quantitative) of the above identified compound named as (2S*)-isomer, respectively, as white solid.

Disodium (2R*,4S,5S)-5-[N-(carboxylatomethyl)-N-{(1R,2R)-2-(2-fluoro-4-biphenylyl)-1-methyl-4-phenylbutyl}carbamoyl]-2-ethoxy-1,3-dioxolane-4-carboxylate $^1$H-NMR(CD$_3$OD) δ:0.88–1.28(6H, m), 2.00–2.41(5H, m), 2.71–2.74(1H, m), 3.43–3.71(3H, m), 4.37–5.16(3H, m), 5.98–6.05(1H, m), 7.05–7.58(13H, m).

FAB-MS:624(M+2Na—H).

Disodium (2S*,4S,5S)-5-[N-(carboxylatomethyl)-N-{(1R,2R)-2-(2-fluoro-4-biphenylyl)-1-methyl-4-phenylbutyl}carbamoyl]-2-ethoxy-1,3-dioxolane-4-carboxylate $^1$H-NMR(CD$_3$OD) δ:0.92–1.03(3H, m), 1.16–1.22(3H, m), 2.09–2.39(4H, m), 3.65–3.73(2H, m), 3.65–3.73(2H, m), 3.98–4.22(2H, m), 4.70–5.48(2H, m), 5.93 and 6.07 (total 1H, each s), 7.05–7.58(13H, m).

FAB-MS:624(M+2Na—H).

EXAMPLE 7

Preparation of (4R,5R)-4-[N-(carboxymethyl)-N-{(1R,2R)-1-methyl-2-(4-phenoxyphenyl)-4-phenylbutyl}carbamoylmethyl]-2,2-dimethyl-1,3-dioxolane-4,5-dicarboxylic acid The above identified compound was obtained by carrying out the same reaction as in Example 4 except that instead of N-(methoxycarbonylmethyl)-{(1R,2R)-2-(2-fluoro-4-biphenylyl)-1-methyl-4-phenylbutyl}amine used as the starting material in Example 4, N-(methoxycarbonylmethyl)-{(1R,2R)-1-methyl-2-(4-phenoxyphenyl)-4-phenylbutyl}amine obtained in Example 51, was used, and instead of diethyl trimesate, dimethyl 2-(carboxymethyl)-2,3-O-isopropylidene-L-tartarate obtained in Reference Example 4, was used.

$^1$H-NMR(CD$_3$OD) δ:0.83–0.95(3H, m), 1.27, 1.41, 1.46 and 1.51(total 6H, each s), 1.80–3.20(7H, m), 3.50–4.05(3H, m), 4.85–5.00(1H, m), 6.93–7.40(14H, m).

FAB-MS:620(M+H).

EXAMPLE 8

Preparation of trisodium (4R,5R)-4-[N-(carboxylatomethyl)-N-{(1R,2R)-1-methyl-2-(4-phenoxyphenyl)-4-phenylbutyl}carbamoylhydroxymethyl]-2,2-dimethyl-1,3-dioxolane-4,5-dicarboxylate 11.6 mg of N-(methoxycarbonylmethyl)-{(1R,2R)-1-methyl-2-(4-phenoxyphenyl)-4-phenylbutyl}amine obtained in Example 51, 9.6 mg of dimethyl 2-(1-acetoxycarboxymethyl)-2,3-O-isopropylidene-L-tartarate obtained in Reference Example 6 and 20 μl of triethylamine, were dissolved in 0.5 ml of chloroform, and a solution of 9.7 mg of 2-chloro-1,3-dimethylimidazolinium chloride in 0.5 ml of chloroform, was added under cooling with ice, followed by stirring at room temperature for 4 hours. The reaction solution was purified by silica gel thin layer chromatography (Kieselgel™60F$_{254}$, Art™5744; hexane/acetone=2/1), to obtain 11.0 mg (yield: 53%) of a condensate as a colorless foam.

10.0 mg of the above condensate was dissolved in 0.6 ml of tetrahydrofuran, and 60 μl of a 1N sodium hydroxide aqueous solution was added, followed by stirring at room temperature for 13 hours. The solvent was distilled off under reduced pressure, and then, methanol was added to the residue. Precipitated crystals were collected by filtration to obtain 5.7 mg (yield: 65%) of the above identified compound as white powder.

$^1$H-NMR(CD$_3$OD) δ:0.79–1.00(3H, m), 1.32, 1.38, 1.49 and 1.68(total 6H, each s), 1.80–3.20(5H, m), 3.50–4.05(3H, m), 4,50–5.35(2H, m), 6.93–7.40(14H, m).

FAB-MS:658(M+Na).

EXAMPLE 9

Preparation of (4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid The above identified compound was obtained by the same method as in Example 4 except that instead of N-(methoxycarbonylmethyl)-{(1R,2R)-2-(2-fluoro-4-biphenylyl)-1-methyl-4-phenylbutyl}amine used as the starting material in Example 4, N-(ethoxycarbonylmethyl)-{(1R,2R)-1-methyl-2-(4-phenoxyphenyl)-4-phenylbutyl}amine obtained in Example 49, was used, and instead of diethyl trimesate, 2,2-diethyl (4S)-1,3-dioxolane-2,2,4-tricarboxylate obtained in Example 56, was used.

$^1$H-NMR(CD$_3$OD) δ:0.80 and 0.97(total 3H, each d, J=6.7 and 6.5 Hz), 1.75–2.70(5H, m), 3.60–4.00(2H, m), 4.25–4.60(3H, m), 5.00–5.10 and 5.23–5.31(total 1H, each m), 6.95–7.40(14H, m).

FAB-MS:578(M+H).

Compounds of Examples 10 to 14 were obtained by carrying out the same reaction as in Example 9 except that instead of 2,2-diethyl (4S)-1,3-dioxolane-2,2,4-tricarboxylate used as the starting material in Example 9, the corresponding carboxylic acid derivatives obtained by the same method as in Example 56, were used.

EXAMPLE 10

(4R)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid $^1$H-NMR(CD$_3$OD) δ:0.83–0.90 and 0.99(total 3H, each m and d, J=6.5 Hz), 1.70–2.47 and 2.60–2.75(total 5H, each m), 3.50–3.75, 3.90–4.15 and 4.20–4.45(total 5H, m), 5.08–5.13 and 5.23–5.30(total 1H, each m), 6.95–7.40(14H, m).

FAB-MS:578(M+H).

EXAMPLE 11

(4S,5S)-4-[N-(carboxymethyl)-N-{(1R,2R)-1-methyl-2-(4-phenoxyphenyl)-4-phenylbutyl}carbamoyl]-5-methyl-1,3-dioxolane-2,2-dicarboxylic acid $^1$H-NMR(CD$_3$COCD$_3$) δ:1.00 and 1.10(total 3H, each d, J=8.7 and 7.5 Hz), 1.45 and 1.53(total 3H, each d, each J=6.6 Hz), 1.80–2.50 and 2.75–3.10(total 5H, each m), 3.80–4.50(3H, m), 4.63–4.72 (1H, m), 5.35 and 5.71(total 1H, each d, each J=6.6 Hz), 7.00–7.50(14H, m).

FAB-MS:592(M+H).

EXAMPLE 12

(4R,5R)-4-[N-(carboxymethyl)-N-{(1R,2R)-1-methyl-2-(4-phenoxyphenyl)-4-phenylbutyl}carbamoyl]-5-methyl-1,3-dioxolane-2,2-dicarboxylic acid $^1$H-NMR(CD$_3$COCD$_3$) δ:0.90–1.00 and 1.17(total 3H, m and d, J=6.5 Hz), 1.45 and 1.53(total 3H, each d, each J=6.3 Hz), 1.80–2.50(4H, m), 2.85–3.00(1H, m), 3.80–4.50 and 4.60–4.73(total 4H, each m), 5.30 and 5.82(total 1H, each d, J=6.5 and 6.3 Hz), 7.00–7.55(14H, m).

FAB-MS:592(M+H).

EXAMPLE 13

(4S,5R)-4-[N-(carboxymethyl)-N-{(1R,2R)-1-methyl-2-(4-phenoxyphenyl)-4-phenylbutyl}carbamoyl]-5-methyl-1,3-dioxolane-2,2-dicarboxylic acid $^1$H-NMR(CD$_3$COCD$_3$) δ:0.93 and 1.07(total 3H, each d, each J=6.5 Hz), 1.32 and 1.40(total 3H, each d, each J=6.3 Hz), 1.80–2.50(4H, m), 2.80–3.00(1H, m), 3.85–4.20 and 4.45–5.12(total 5H, each m), 7.00–7.55(14H, m).

FAB-MS:592(M+H).

EXAMPLE 14

(4R,5S)-4-[N-(carboxymethyl)-N-{(1R,2R)-1-methyl-2-(4-phenoxyphenyl)-4-phenylbutyl}carbamoyl]-5-methyl-1,3-dioxolane-2,2-dicarboxylic acid $^1$H-NMR(CD$_3$COCD$_3$) δ:0.98–1.03 and 1.07(total 3H, m and d, each J=6.5 Hz), 1.40 and 1.45(total 3H, each d, J=6.4 and 6.3 Hz), 2.00–2.50(4H, m), 2.85–3.00(1H, m), 3.90(1H, d, J=17.0 Hz), 4.25(1H, d, J=17.0 Hz), 4.25–4.36(1H, m), 4.60–4.72 (1H, m), 4.90 and 5.25(total 1H, each d, each J=5.0 Hz), 7.00–7.55 (14H, m).

FAB-MS:592(M+H).

EXAMPLE 15

(4R*,5S*)-4-[N-(carboxymethyl)-N-{(1R,2R)-1-methyl-2-(4-phenoxyphenyl)-4-phenylbutyl}carbamoyl]-5-ethyl-1,3-dioxolane-2,2-dicarboxylic acid, and (4S*,5R*)-4-[N-(carboxymethyl)-N-{(1R,2R)-1-methyl-2-(4-phenoxyphenyl)-4-phenylbutyl}carbamoyl]-5-ethyl-1,3-dioxolane-2,2-dicarboxylic acid 96 mg of N-(ethoxycarbonylmethyl)-{(1R,2R)-1-methyl-2-(4-phenoxyphenyl)-4-phenylbutyl}amine obtained in Example 49, 66 mg of 2,2-diethyl (4RS,5SR)-5-ethyl-1,3-dioxolane-2,2,4-tricarboxylate obtained in Example 67 and 96 μl of triethylamine, were dissolved in 1 ml of chloroform, and a solution of 58 mg of 2-chloro-1,3-dimethylimidazolinium chloride in 0.5 ml of chloroform, was added under cooling with ice, followed by stirring at room temperature for 30 minutes. The reaction solution was poured into water and extracted with chloroform. The extract solution was washed with water, a saturated sodium hydrogen carbonate aqueous solution and a saturated sodium chloride aqueous solution and then, dried over anhydrous magnesium sulfate. The drying agent was filtered off, and then, the solvent was distilled off under reduced pressure. The residue was subjected to silica gel thin layer chromatography (Kieselgel™60F$_{254}$, Art™5744; hexane/ethyl acetate=3/1) to separate triethylesters of the above identified compounds named as (4R*,5S*)-isomer and (4S*,5R*)-isomer, for the sake of convenience, and they were obtained in an amounts of 59 mg (yield: 40%) and 60 mg (yield: 41%), respectively, as colorless oily substances.

59 mg and 60 mg of the above esters were, respectively, dissolved in 4 ml of 50% tetrahydrofuran aqueous solutions separately, and 1 ml of sodium hydroxide aqueous solutions were added thereto, respectively, followed by stirring at room temperature for 1 hour. The reaction solutions were acidified with 1N hydrochloric acid and then, extracted with ethyl ether, followed by drying over anhydrous magnesium sulfate. The drying agent was filtered off, and then, the solvent was distilled off under reduced pressure, to obtain 50 mg (yield: 90%) of the above identified compound named as (4R*,5S*)-isomer for the sake of convenience and 55 mg (yield: 97%) of the above identified compound named as (4S*,5R*)-isomer, respectively, as colorless foams.

(4R*,5S*)-4-[N-(carboxymethyl)-N-{(1R,2R)-1-methyl-2-(4-phenoxyphenyl)-4-phenylbutyl}carbamoyl]-5-ethyl-1,3-dioxolane-2,2-dicarboxylic acid $^1$H-NMR(CD$_3$COCD$_3$) δ:0.98–1.16(6H, m), 1.40–3.12 (7H, m), 3.95–4.60(4H, m), 5.35 and 5.70(total 1H, each d, each J=6.6 Hz), 7.00–7.50(14H, m).

FAB-MS:606(M+H).

(4S*,5R*)-4-[N-(carboxymethyl)-N-{(1R,2R)-1-methyl-2-(4-phenoxyphenyl)-4-phenylbutyl}carbamoyl]-5-ethyl-1,3-dioxolane-2,2-dicarboxylic acid $^1$H-NMR(CD$_3$COCD$_3$) δ:0.85–1.18(6H, m), 1.75–2.50 (7H, m), 2.85–3.10(1H, m), 3.90–4.52(4H, m), 5.28 and 5.83(total 1H, each d, each J=6.5 Hz), 7.00–7.53(14H, m).

FAB-MS:606(M+H).

EXAMPLE 16

Preparation of (2S*,4R)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid, and (2R*,4R)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid (1) Preparation of 4-tert-butyl 2-ethyl (2RS,4R)-2-[N-(tert-butoxycarbonylmethyl)-N-{(1R,2R)-1-methyl-2-(4-phenoxyphenyl)-4-phenylbutyl}carbamoyl]-1,3-dioxolane-2,4-dicarboxylate 100 mg of N-(tert-butoxycarbonylmethyl)-{(1R,2R)-1-methyl-2-(4-phenoxyphenyl)-4-phenylbutyl}amine obtained in Example 50, 72 mg of 4-tert-butyl 2-ethyl (2RS,4R)-1,3-dioxolane-2,2,4-tricarboxylate obtained in Reference Example 7 and 153 μl of triethylamine, were dissolved in 2 ml of chloroform, and a solution of 61 mg of 2-chloro-1,3-dimethylimidazolinium chloride in 1 ml of chloroform, was added under cooling with ice, followed by stirring at the same temperature for 1 hour. The reaction solution was poured into water and extracted with ethyl acetate. The extract solution was washed with a saturated sodium chloride aqueous solution and then dried over anhydrous sodium sulfate. The drying agent was filtered off, and then, the solvent was distilled off under reduced pressure. The residue was purified by silica gel column chromatography (hexane/ethyl acetate=5/1) to obtain 122 mg (yield: 79%) of the above identified compound as a colorless oily substance.

(2) Preparation of 2-ethyl (2RS,4R)-2-[N-(carboxymethyl)-N-{(1R,2R)-1-methyl-2-(4-phenoxyphenyl)-4-phenylbutyl}carbamoyl]-1,3-dioxolane-2,4-dicarboxylate 122 mg of 4-tert-butyl 2-ethyl (2RS,4R)-2-[N-(tert-butoxycarbonylmethyl)-N-{(1R,2R)-1-methyl-2-(4-phenoxyphenyl)-4-phenylbutyl}carbamoyl]-1,3-dioxolane-2,4-dicarboxylate was dissolved in 3 ml of formic acid, followed by stirring at room temperature for 3 hours. Formic acid was distilled off under reduced pressure to obtain 96 mg (yield: 89%) of the above identified compound as a colorless oily substance.

(3) Preparation of (2S*,4R)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid, and (2R*,4R)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid 77 mg of 2-ethyl (2RS,4R)-2-[N-(carboxymethyl)-N-{(1R,2R)-1-methyl-2-(4-phenoxyphenyl)-4-phenylbutyl}carbamoyl]-1,3-dioxolane-2,4-dicarboxylate was dissolved in 2 ml of tetrahydrofuran, and 0.6 ml of a 1N sodium hydroxide aqueous solution was added, followed by stirring at room temperature for 2 days. The reaction solution was acidified with 1N hydrochloric acid and then extracted with ethyl ether. The extract solution was washed with a saturated sodium chloride aqueous solution and then dried over anhydrous magnesium sulfate. The drying agent was filtered off, and then, the solvent was distilled off under reduced pressure. The residue was purified by medium pressure liquid chromatography (Lobar column™, Size A, RP-8, manufactured by Merck Co.; acetonitrile/0.1% trifluoroacetic acid aqueous solution=1/1), to obtain 43 mg (yield: 59%) of the above identified compound as a preceding fraction of medium pressure liquid chromatography, named as (2S*,4R)-isomer, for the sake of convenience, as white solid, and 24 mg (yield: 33%) of the above identified compound as a later fraction of medium pressure liquid chromatography, named as (2R*,4R)-isomer, for the sake of convenience, as a colorless foam.

(2S*,4R)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid $^1$H-NMR(CD$_3$OD) δ:0.90 and 0.94(total 3H, each d, each J=6.5 Hz), 1.75–2.45(4H, m), 2.55–2.68(1H, m), 3.66 and 3.74(total 1H, each d, each J=17.1 Hz), 3.93 and 3.97(total 1H, each d, each J=17.1 Hz), 4.03–4.41(3H, m), 4.48–4.57 (1H, m), 6.92–7.00(4H, m), 7.01–7.16(4H, m), 7.17–7.28 (4H, m), 7.28–7.38(2H, m).

FAB-MS:578(M+H).

(2R*,4R)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid $^1$H-NMR(CD$_3$COCD$_3$) δ:0.96 and 1.00(total 3H, each d, each J=6.6 Hz), 1.79–2.10(1H, m), 2.12–2.45(3H, m), 2.75–2.87(1H, m), 3.75(1H, d, J=17.0 Hz), 4.05(1H, d, J=17.0 Hz), 4.18–4.43 (3H, m), 4.74–5.00(1H, m), 6.98–7.06(4H, m), 7.07–7.17(4H, m), 7.17–7.26(2H, m), 7.28–7.38(4H, m).

FAB-MS:578(M+H).

EXAMPLE 17

Preparation of (2S*,4S)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid (1) Preparation of 4-tert-butyl 2-ethyl (2S*,4S)-2-[N-(ethoxycarbonylmethyl)-N-{(1R,2R)-1-methyl-2-(4-phenoxyphenyl)-4-phenylbutyl}carbamoyl]-1,3-dioxolane-2,4-dicarboxylate 239 mg of N-(ethoxycarbonylmethyl)-{(1R,2R)-1-methyl-2-(4-phenoxyphenyl)-4-phenylbutyl}amine obtained in Example 49, 166 mg of 4-tert-butyl 2-ethyl (2S*,4S)-1,3-dioxolane-2,2,4-tricarboxylate obtained in Reference Example 8 and 238 μl of triethylamine, were dissolved in 5 ml of chloroform, and a solution of 145 mg of 2-chloro-1,3-dimethylimidazolinium chloride in 3 ml of chloroform, was added under cooling with ice, followed by stirring at the same temperature for 1 hour. The reaction solution was poured into water and extracted with ethyl acetate. The extract solution was washed with a saturated sodium chloride aqueous solution and then, dried over anhydrous sodium sulfate. The drying agent was filtered off, and then, the solvent was distilled off under reduced pressure. The residue was purified by silica gel column chromatography (hexane/ethyl acetate=5/1) to obtain 310 mg (yield: 78%) of the above identified compound as a colorless oily substance.

(2) Preparation of (2S*,4S)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid 310 mg of 4-tert-butyl 2-ethyl (2S*,4S)-2-[N-(ethoxycarbonylmethyl)-N-{(1R,2R)-1-methyl-2-(4-phenoxyphenyl)-4-phenylbutyl}carbamoyl]-1,3-dioxolane-2,4-dicarboxylate was dissolved in 4 ml of formic acid, followed by stirring at room temperature for 2 hours. The reaction solution was evaporated to dryness under reduced pressure, and then, the residue was dissolved in 6 ml of a 50% tetrahydrofuran aqueous solution. 3 ml of a 1N sodium hydroxide aqueous solution was added, followed by stirring at room temperature for 6 hours. The reaction solution was acidified with 1N hydrochloric acid and then extracted with ethyl ether. The organic layer was dried over anhydrous magnesium sulfate. The drying agent was filtered off, and then, the solvent was distilled off under reduced pressure. The residue was purified by medium pressure liquid chromatography (Lobar column™, Size B, RP-8, manufactured by Merck Co.; acetonitrile/0.1% trifluoroacetic acid aqueous solution=1/1) to obtain 216 mg (yield: 84%) of the above identified compound as a colorless foam.

$^1$H-NMR(CD$_3$COCD$_3$) δ:0.99(3H, d, J=6.4 Hz), 1.80–2.45(4H, m), 2.75–2.88(1H, m), 3.75(1H, d, J=17.0 Hz), 4.10(1H, d, J=17.0 Hz), 4.14–4.45(3H, m), 4.86 and 4.97(total 1H, each dd, J=4.0, 7.2 Hz and 3.6, 7.2 Hz), 7.00–7.45(14H, m).

FAB-MS:578(M+H).

EXAMPLE 18

Preparation of (2R*,4S)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid The above identified compound was obtained by the same method as in Example 17 except that instead of 4-tert-butyl 2-ethyl (2S*,4S)-1,3-dioxolane-2,2,4-tricarboxylate used as the starting material in Example 17, 4-tert-butyl 2-ethyl (2R*,4S)-1,3-dioxolane-2,2,4-tricarboxylate was used.

$^1$H-NMR(CD$_3$COCD$_3$) δ:1.02(3H, d, J=6.4 Hz), 1.80–2.40(4H, m), 2.83–2.95(1H, m), 3.89(1H, d, J=17.1 Hz), 4.18(1H, d, J=17.1 Hz), 4.26(1H, dd, J=6.0 and 8.8 Hz), 4.22–4.40(1H, m), 4.67(1H, dd, J=7.3 and 8.8 Hz), 4.90(1H, dd, J=6.0 and 7.3 Hz), 7.03–7.45 (14H, m).

FAB-MS:578(M+H).

EXAMPLE 19

Preparation of 2-ethyl (2S*,4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylate, and 2-ethyl (2R*,4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylate (1) Preparation of 5-tert-butyl 2,2-diethyl (4R,5R)-4-[N-(tert-butoxycarbonylmethyl)-N-{(1R,2R)-1-methyl-2-(4-phenoxyphenyl)-4-phenylbutyl}carbamoyl]-1,3-dioxolane-2,2,5-tricarboxylate 860 mg of N-(tert-butoxycarbonylmethyl)-{(1R,2R)-1-methyl-2-(4-phenoxyphenyl)-4-phenylbutyl}amine obtained in Example 50, 1.04 g of 5-tert-butyl 2,2-diethyl (4R,5R)-1,3-dioxolane-2,2,4,5-tetracarboxylate obtained in Example 68, and 2.02 ml of triethylamine, were dissolved in 20 ml of chloroform, and a solution of 816 mg of 2-chloro-1,3-dimethylimidazolinium chloride in 10 ml of chloroform, was added under cooling with ice, followed by stirring at the same temperature for 1 hour. The reaction solution was poured into water and extracted with ethyl acetate. The extract solution was washed with a saturated sodium chloride aqueous solution and then, dried over anhydrous sodium sulfate. The drying agent was filtered off and then, the solvent was distilled off under reduced pressure. The residue was purified by silica gel column chromatography (hexane/ethyl acetate=5/1) to obtain 1.45 g (yield: 95%) of the above identified compound as a colorless oily substance.

(2) Preparation of 5-tert-butyl 2-ethyl (2RS,4R,5R)-4-[N-(tert-butoxycarbonylmethyl)-N-{(1R,2R)-1-methyl-2-(4-phenoxyphenyl)-4-phenylbutyl}carbamoyl]-1,3-dioxolane-2,2,5-tricarboxylate 1.45 g of 5-tert-butyl 2,2-diethyl (4R,5R)-4-[N-(tert-butoxycarbonylmethyl)-N-{(1R,2R)-1-methyl-2-(4-phenoxyphenyl)-4-phenylbutyl}carbamoyl]-1,3-dioxolane-2,2,5-tricarboxylate was dissolved in a mixed liquid comprising 20 ml of tetrahydrofuran and 10 ml of water, and 1.83 ml of a 1N sodium hydroxide aqueous solution was added, followed by stirring at room temperature for 18 hours. The reaction solution was acidified by an addition of 1N hydrochloric acid and then extracted with ethyl acetate. The extract solution was washed with a saturated sodium chloride aqueous solution and then dried over anhydrous magnesium sulfate. The drying agent was filtered off and then, the solvent was distilled off under reduced pressure. The residue was purified by silica gel column chromatography (hexane/ethyl acetate=1/1→1/3) to obtain 580 mg (yield: 40%) of the above identified compound as a colorless foam.

(3) Preparation of 2-ethyl (2S*,4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylate, and 2-ethyl (2R*,4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylate 30 ml of formic acid was added to 580 mg of 5-tert-butyl 2-ethyl (2RS,4R,5R)-4-[N-(tert-butoxycarbonylmethyl)-N-{(1R,2R)-1-methyl-2-(4-phenoxyphenyl)-4-phenylbutyl}carbamoyl]-1,3-dioxolane-2,2,5-tricarboxylate, followed by stirring at room temperature for 15 hours. Formic acid was distilled off under reduced pressure. Then, the residue was purified by medium pressure liquid chromatography (Lobar column™, Size C, RP-8, manufactured by Merck Co.; acetonitrile/0.1% trifluoroacetic acid aqueous solution=1/1), to obtain 185 mg (yield: 37%) of the above identified compound as a preceding fraction of the medium pressure liquid chromatography, named as (2S*,4R,5R)-isomer, for the sake of convenience, and 203 mg (yield:41%) of the above identified compound as a later fraction of the medium pressure liquid chromatography, named as (2R*,4R,5R)-isomer, for the sake of convenience, respectively.

2-ethyl (2S*,4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylate $^1$H-NMR(CD$_3$COCD$_3$) δ:0.90–1.13(3H, m), 1.13–1.30 (3H, m), 1.80–2.40(4H, m), 2.80–2.95(1H, m), 3.65–4.75 (5H, m), 5.13–5.35, 5.45–5.55 and 5.90–5.97(total 2H, each m), 6.90–7.50(14H, m).

FAB-MS:650(M+H).

2-ethyl (2R*,4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylate ¹H-NMR(CD₃COCD₃) δ:0.93–1.15(3H, m), 1.15–1.30 (3H, m), 1.80–2.40(4H, m), 2.85–3.02(1H, m), 3.90–4.00, 4.00–4.30 and 4.40–4.60(total 5H, each m), 5.12–5.22, 5.45–5.55 and 5.95–6.05(total 2H, each m), 6.90–7.25 and 7.35–7.50(total 14H, each m).

FAB-MS:650(M+H).

EXAMPLE 20

Preparation of 2-ethyl (2S*,4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylate, and 2-ethyl (2R*,4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylate 992 mg of 5-tert-butyl 2-ethyl (2RS,4S,5S)-4-[N-(tert-butoxycarbonylmethyl)-N-{(1R,2R)-1-methyl-2-(4-phenoxyphenyl)-4-phenylbutyl}carbamoyl]-1,3-dioxolane-2,2,5-tricarboxylate obtained by treating in the same manner as in Example 19(1) and (2) except that instead of 5-tert-butyl 2,2-diethyl (4R,5R)-1,3-dioxolane-2,2,4,5-tetracarboxylate used as the starting material in Example 19(1), 5-tert-butyl 2,2-diethyl (4S,5S)-1,3-dioxolane-2,2,4,5-tetracarboxylate obtained in Example 70 was used, was purified by means of high performance chromatography for fractionation (CapcellpakC18, UG, column temperature: 40° C., acetonitrile/0.5% phosphoric acid aqueous solution=3/1) to obtain 380 mg (yield: 38%) of a di-tert-butyl ester of the above identified compound as a preceding fraction of the high performance liquid chromatography, named as (2S*,4S,5S)-isomer for the sake of convenience and 394 mg (yield: 38%) of a di-tert-butyl ester of the above identified compound as a later fraction of the high performance liquid chromatography named as (2R*,4S,5S)-isomer for the sake of convenience, respectively, as colorless foams.

137 mg and 75 mg of the above esters were, respectively, dissolved in 3 ml of formic acid, separately, followed by stirring at room temperature for 2 hours. The solvent was distilled off under reduced pressure to obtain 116 mg (yield: quantitative) of the above identified compound named as (2S*,4S,5S)-isomer for the sake of convenience and 63 mg (yield: quantitative) of the above identified compound named as (2S*,4S,5S)-isomer, respectively, as colorless foams.

2-ethyl (2S*,4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylate ¹H-NMR(CD₃COCD₃) δ:0.89 and 1.08(total 3H, each d, J=6.9 and 6.6 Hz), 1.20–1.30(3H, m), 1.80–2.60(4H, m), 2.75–2.95 (1H, m), 3.80–4.30 and 4.50–5.00(total 5H, each m), 5.28, 5.43, 5.44 and 5.72(total 2H, each d, J=4.5, 4.4, 4.5 and 4.4 Hz), 7.00–7.50(14H, m).

FAB-MS:650(M+H).

2-ethyl (2R*,4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylate ¹H-NMR(CD₃COCD₃) δ:0.94 and 1.10(total 3H, each m, each J=6.6 Hz), 1.20–1.33(3H, m), 1.83–2.50(4H, m), 2.87–3.03(1H, m), 3.85–4.30 and 4.45–5.05(total 5H, each m), 5.28 and 5.30 (total 1H, each d, J=3.1 and 3.8 Hz), 5.60 and 5.91(total 1H, each d, J=3.1 and 3.8 Hz), 7.00–7.50 (14H, m).

FAB-MS:650(M+H).

EXAMPLE 21

Preparation of (4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid 305 mg of 5-tert-butyl 2,2-diethyl (4R,5R)-4-[N-(tert-butoxycarbonylmethyl)-N-{(1R,2R)-1-methyl-2-(4-phenoxyphenyl)-4-phenylbutyl}carbamoyl]-1,3-dioxolane-2,2,5-tricarboxylate obtained in Example 19(1), was dissolved in 4 ml of formic acid, followed by stirring at room temperature for 2 hours. Formic acid was distilled off under reduced pressure, and the residue was azeotropically distilled twice with toluene.

The residue was dissolved in 10 ml of a 50% tetrahydrofuran aqueous solution, and 3 ml of a 1N sodium hydroxide aqueous solution was added, followed by stirring at room temperature for 1.5 hours. The reaction solution was acidified with 1N hydrochloric acid and then, extracted with ethyl ether and dried over anhydrous magnesium sulfate. The drying agent was filtered off, and then, the solvent was distilled off under reduced pressure to obtain 225 mg (yield: 94%) of the above identified compound as a colorless foam.

¹H-NMR(CD₃COCD₃) δ:0.98 and 1.11(total 3H, each d, each J=6.6 Hz), 1.80–2.50(4H, m), 2.88–3.02(1H, m), 3.95 (1H, d, J=17.2 Hz), 4.25(1H, d, J=17.2 Hz), 4.40–4.60(1H, m), 5.22, 5.24, 5.57 and 6.05(total 2H, each d, J=3.7, 3.7, 3.5 and 3.5 Hz), 7.00–7.55(14H, m).

FAB-MS:622(M+H).

EXAMPLE 22

Preparation of (4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid The above identified compound was obtained by carrying out the same reaction as in Example 19(1) except that instead of 5-tert-butyl 2,2-diethyl (4R,5R)-1,3-dioxolane-2,2,4,5-tetracarboxylate used as the starting material in Example 19(1), 5-tert-butyl 2,2-diethyl (4S,5S)-1,3-dioxolane-2,2,4,5-tetracarboxylate obtained in Example 70, was used, followed by treatment in the same manner as in Example 21.

¹H-NMR(CD₃COCD₃) δ:0.94 and 1.09(total 3H, each d, J=6.7 and 6.9 Hz), 1.82–2.50(4H, m), 2.83–3.00(1H, m), 3.90–4.30 and 4.50–5.05(total 3H, each m), 5.31 and 5.35 (total 1H, each d, J=3.3 and 3.7 Hz), 5.60 and 5.87(total 1H, each d, J=3.3 and 3.7 Hz), 7.00–7.50(14H, m).

FAB-MS:622(M+H).

EXAMPLE 23

Preparation of (4R*,5S*)-4-[N-(carboxymethyl)-N-{(1R,2R)-1-methyl-2-(4--phenoxyphenyl)-4--phenylbutyl}carbamoyl]-1,3-dioxolane-2,2,5-tricarboxylic acid, and (4S*,5R*)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid 396 mg of N-(tert-butoxycarbonylmethyl)-{(1R,2R)-1-methyl- 2-(4-phenoxyphenyl)-4-phenylbutyl}amine obtained in Example 50, 321 mg of 5-tert-butyl 2,2-diethyl (4RS,5SR)-1,3-dioxolane-2,2,4,5-tetracarboxylate obtained in Example 72, and 270 μl of N-methylmorpholine, were dissolved in 3 ml of chloroform, and a solution of 225 mg of 2-chloro-1,3-dimethylimidazolinium chloride in 2 ml of chloroform, was added under cooling with ice, followed by stirring at the same temperature for 30 minutes. The reaction solution was poured into water and then extracted with chloroform and dried over anhydrous magnesium sulfate. The drying agent was filtered off, and then, the solvent was distilled off under reduced pressure. The residue was roughly purified by silica gel column chromatography (hexane/ethyl acetate=5/1) and then purified by means of high performance chromatography for fractionation (Senshupak5301N, hexane/ethyl acetate=5/1) to obtain 256 mg (yield: 36%) of an ester of the above identified compound as a preceding fraction of the high performance liquid chromatography named as (4R*,5S*)-isomer for the sake of convenience, and 183 mg (yield: 26%) of an ester of the above identified compound as a later fraction of the high performance liquid chromatography named as (4S*,5R*)-isomer for the sake of convenience, respectively, as colorless oily substances.

76 mg and 127 mg of the above esters were, respectively, treated in the same manner as in Example 21, separately, to obtain 50 mg (yield: 84%) of the above identified compound named as (4R*,5S*)-isomer for the sake of convenience, and 172 mg (yield: 88%) of the above identified compound named as (4S*,5R*)-isomer, respectively, as colorless foams.

(4R*,5S*)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid $^1$H-NMR(CD$_3$COCD$_3$) δ:0.88 and 1.08(total 3H, each d, each J=6.5 Hz), 1.73–3.00(5H, m), 3.92, 4.15 and 4.53(total 2H, each d, J=17.0, 17.0 and 19.0 Hz), 4.35–4.48(1H, m), 5.21, 5.31, 5.67 and 6.16(total 2H, each d, each J=7.3 Hz), 6.95–7.50(14H, m).

FAB-MS:622(M+H).

(4S*,5R*)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid $^1$H-NMR(CD$_3$COCD$_3$) δ:0.85 and 1.05(total 3H, each d, J=6.3 and 6.6 Hz), 1.70–2.95(5H, m), 3.65–4.60(3H, m), 5.15, 5.23, 5.65 and 5.80(total 2H, each d, J=6.7, 7.4, 7.4 and 7.3 Hz), 6.90–7.45(14H, m).

FAB-MS:622(M+H).

EXAMPLE 24

Preparation of 5-tert-butyl (4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylate (1) Preparation of 5-tert-butyl 2,2-bis{2-(trimethylsilyl)ethyl} (4S,5S)-4-[N-(benzyloxycarbonylmethyl)-N-{(1R,2R)-1-methyl-2-(4-phenoxyphenyl)-4-phenylbutyl}carbamoyl]-1,3-dioxolane-2,2,5-tricarboxylate The above identified compound was obtained by carrying out the same reaction as in Example 19(1) except that instead of N-(tert-butoxycarbonylmethyl)-{(1R,2R)-1-methyl-2-(4-phenoxyphenyl)-4-phenylbutyl}amine used as the starting material in Example 19(1), N-(benzyloxycarbonylmethyl)-{(1R,2R)-1-methyl-2-(4-phenoxyphenyl)-4-phenylbutyl}amine obtained in Example 52, was used, and instead of 5-tert-butyl 2,2-diethyl (4R,5R)-1,3-dioxolane-2,2,4,5-tetracarboxylate, 5-tert-butyl 2,2-bis{2-(trimethylsilyl)ethyl} (4S,5S)-1,3-dioxolane-2,2,4,5-tetracarboxylate obtained in Example 73, was used.

(2) Preparation of 2,2-bis{2-(trimethylsilyl)ethyl} 5-tert-butyl (4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylate 20 mg of 5-tert-butyl (4S,5S)-4-[N-(benzyloxycarbonylmethyl)-N-{(1R,2R)-1-methyl-2-(4-phenoxyphenyl)-4-phenylbutyl}carbamoyl]-1,3-dioxolane-2,2,5-tricarboxylate was dissolved in 0.5 ml of N,N-dimethylformamide, and 103 μl of a 1M tetrahydrofuran solution of tetrabutylammonium fluoride, was added, followed by stirring at room temperature for one hour. Water was poured into the reaction solution, and 1N hydrochloric acid was added, followed by extraction with ethyl ether. The extract solution was washed with a saturated sodium chloride aqueous solution and then, dried over anhydrous magnesium sulfate. The drying agent was filtered off and then, the solvent was distilled off under reduced pressure. The residue was purified by medium pressure liquid chromatography (Lobar column™, Size A, RP-8, manufactured by Merck Co.; acetonitrile/0.1% trifluoroacetic acid aqueous solution=1/1) to obtain 15 mg (yield: 94%) of a benzylester of the above identified compound as a colorless oily substance.

15 mg of the above ester was dissolved in 1 ml of 1,4-dioxane, and 10 mg of a 10% palladium-carbon catalyst was added, followed by catalytic reduction for 3 hours at room temperature under hydrogen normal pressure. The catalyst was filtered off, and then, the filtrate was evaporated to dryness under reduced pressure. The residue was purified by medium pressure liquid chromatography (Lobar column™, Size A, RP-8, manufactured by Merck Co.; acetonitrile/0.1% trifluoroacetic acid aqueous solution=1/1) to obtain 6.6 mg (yield: 50%) of the above identified compound.

$^1$H-NMR(CD$_3$COCD$_3$) δ:0.85–1.20(3H, m), 1.25–1.53 (9H, m), 1.78–2.53(4H, m), 2.80–3.00(1H, m), 3.85–5.15 (3H, m), 5.15–5.20(1H, m), 5.15–5.58 and 5.76–5.80(total 1H, each m), 7.00–7.50(14H, m).

FAB-MS:678(M+H).

EXAMPLE 25

Preparation of (4S,5S)-4-N-(carboxymethyl)-N-{(1R,2R)-1-methyl-2-(4-phenoxyphenyl)-4-phenylbutyl}carbamoyl]-5-(N-ethylcarbamoyl)-1,3-dioxolane-2,2-dicarboxylic acid (1) Preparation of 2,2-bis{2-(trimethylsilyl)ethyl} (4S,5S)-4-[N-(benzyloxycarbonylmethyl)-N-{(1R,2R)-1-methyl-2-(4-phenoxyphenyl)-4-phenylbutyl}carbamoyl]-1,3-dioxolane-2,2,5-tricarboxylate 307 mg of 5-tert-butyl 2,2-bis{2-(trimethylsilyl)ethyl} (4S,5S)-4-[N-(benzyloxycarbonylmethyl)-N-{(1R,2R)-1-methyl-2-(4-phenoxyphenyl)-4-phenylbutyl}carbamoyl]-1,3-dioxolane-2,2,5-tricarboxylate (compound of Example 24(1)), 5 ml of formic acid and 1 ml of chloroform, were mixed and stirred at room temperature for 5 hours. The reaction solution was concentrated under reduced pressure. The residue was purified by silica gel column chromatography (chloroform/methanol=30/1→10/1) to obtain 108 mg (yield: 37%) of the above identified compound.

(2) Preparation of 2,2-bis{2-(trimethylsilyl)ethyl} (4S,5S)-4-[N-(benzyloxycarbonylmethyl)-N-{(1R,2R)-1-methyl-2-(4-phenoxyphenyl)-4-phenylbutyl}carbamoyl]-5-(N-ethylcarbamoyl)-1,3-dioxolane-2,2-dicarboxylate 25 mg of 2,2-bis{2-(trimethylsilyl)ethyl} (4S,5S)-4-[N-(benzyloxycarbonylmethyl)-N-{(1R,2R)-1-methyl-2-(4-phenoxyphenyl)-4-phenylbutyl}carbamoyl]-1,3-dioxolane-2,2,5-tricarboxylate, 5 mg of ethylamine hydrochloride and 45 μl of triethylamine, were dissolved in 1 ml of chloroform, and a solution of 18 mg of 2-chloro-1,3-dimethylimidazolinium chloride in 0.3 ml of chloroform, was added under cooling with ice, followed by stirring at the same temperature for 2 hours. The reaction solution was poured into water and extracted with chloroform and dried over anhydrous magnesium sulfate. The drying agent was filtered off, and then, the solvent was distilled off under reduced pressure. The residue was purified by silica gel column chromatography (hexane/ethyl acetate=2/1) to obtain 18 mg (yield: 70%) of the above identified compound as a colorless oily substance.

(3) Preparation of (4S,5S)-4-[N-(carboxymethyl)-N-{(1R,2R)-1-methyl-2-(4-phenoxyphenyl)-4-phenylbutyl}carbamoyl]-5-(N-ethylcarbamoyl)-1,3-dioxolane-2,2-dicarboxylate 10 mg (yield: 80%) of the above identified compound was obtained as a colorless oily substance by treating in the same manner as in Example 24(2) 18 mg of 2,2-bis{2-(trimethylsilyl)ethyl} (4S,5S)-4-[N-(benzyloxycarbonylmethyl)-N-{(1R,2R)-1-methyl-2-(4-phenoxyphenyl)-4-phenylbutyl}carbamoyl]-5-(N-ethylcarbamoyl)-1,3-dioxolane-2,2-dicarboxylate.

$^1$H-NMR(CD$_3$COCD$_3$) δ:0.85–1.20(6H, m), 1.80–2.48 (4H, m), 2.85–3.00(1H, m), 3.20–3.40(2H, m), 3.96(1H, d, J=17.0 Hz), 4.16 (1H, d, J=17.0 Hz), 4,50–4.85(1H, m), 5.18–5.25(1H, m), 5.50–5.53 and 5.73–5.75(total 1H, each m), 7.00–7.43(14H, m), 7.50–7.60(1H, br s).

FAB-MS:649(M+H).

EXAMPLE 26

Preparation of (4S,5S)-5-carbamoyl-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid The above identified compound was obtained as white solid by carrying out the same reaction as in Example 25 except that instead of ethylamine hydrochloride used as the starting material in Example 25(2), ammonium chloride was used.

$^1$H-NMR(CD$_3$COCD$_3$) δ:0.93–1.33(3H, m), 1.80–2.45 (4H, m), 2.85–3.00(1H, m), 3.98(1H, d, J=17.1 Hz), 4.17 (1H, d, J=17.1 Hz), 4.50–4.83(1H, m), 5.24–5.30(1H, m), 5.53 and 5.86(total 1H, each d, each J=3.2 Hz), 7.00–7.43 (14H, m), 7.50–7.70 and 7.88–7.93(total 2H, each br s).

FAB-MS:621(M+H).

EXAMPLE 27

Preparation of (4S,5R)-4-[N-(carboxymethyl)-N-{(1R,2R)-1-methyl-2-(4-phenoxyphenyl)-4-phenylbutyl}carbamoyl]-5-(hydroxymethyl)-1,3-dioxolane-2,2-dicarboxylic acid 60 mg of 2,2-bis{2-(trimethylsilyl)ethyl} (4S,5S)-4-[N-(benzyloxycarbonylmethyl)-N-{(1R,2R)-1-methyl-2-(4-phenoxyphenyl)-4-phenylbutyl}carbamoyl]-1,3-dioxolane-2,2,5-tricarboxylate (compound of Example 25(1)) and 18 μl of triethylamine, were dissolved in 2 ml of tetrahydrofuran, and 17 μl of isobutyl chloroformate was added under cooling with ice, followed by stirring at the same temperature for 30 minutes. Then, 0.3 ml of water and 12 mg of sodium borohydride were added, followed by stirring for further one hour. The reaction solution was poured into water and extracted with ethyl acetate. Then, the extract solution was dried over anhydrous magnesium sulfate. The drying agent was filtered off, and then, the solvent was distilled off under reduced pressure. The residue was purified by silica gel column chromatography (hexane/ethyl acetate=2/1) to obtain 29 mg (yield: 50%) of a triester of the above identified compound as a colorless oily substance.

22 mg of the above ester was treated in the same manner as in Example 25(3) to obtain 8.2 mg (yield: 55%) of the above identified compound as a colorless oily substance.

$^1$H-NMR(CD$_3$COCD$_3$)δ:0.85–1.10(3H, m), 1.80–2.50 (4H, m), 2.85–3.00(1H, m), 3.62–4.00 and 4.15–4.30(total 4H, each m), 4,50–4.83(1H, m), 5.21(1H, d, J=3.2 Hz), 5.57(1H, d, J=3.2 Hz), 6.90–7.50(14H, m).

FAB-MS:608(M+H).

EXAMPLE 28

Preparation of (2S*,4S,5S)-4-[N-(carboxymethyl)-N-{(1R,2R)-1-methyl-2-(4-phenoxyphenyl)-4-phenylbutyl}carbamoyl]-2-(N-ethylcarbamoyl)-1,3-dioxolane-2,5-dicarboxylic acid The above identified compound was obtained by carrying out treatment in the same manner as in Example 25(2) except that instead of 2,2-bis{2-(trimethylsilyl)ethyl} (4S,5S)-4-[N-(benzyloxycarbonylmethyl)-N-{(1R,2R)-1-methyl-2-(4-phenoxyphenyl)-4-phenylbutyl}carbamoyl]-1,3-dioxolane-2,2,5-tricarboxylate, 5-tert-butyl 2-ethyl (2R*,4S,5S)-4-[N-(tert-butoxycarbonylmethyl)-N-{(1R,2R)-1-methyl-2-(4-phenoxyphenyl)-4-phenylbutyl}carbamoyl]-1,3-dioxolane-2,2,5-tricarboxylate obtained in Example 20, was used, and carrying out the same reaction as in Example 21.

$^1$H-NMR(CD$_3$COCD$_3$) δ:0.83–1.00(6H, m), 1.80–2.55 (4H, m), 2.80–2.97(1H, m), 3.20–3.35(2H, m), 3.95, 4.13 and 4.55(total 2H, each d, each J=17.0 Hz), 4.00–4.23 and 4.48–4.51(total 1H, each m), 5.40, 5.44, 5.52 and 5.89(total 2H, each d, each J=3.5 Hz), 7.00–7.50(14H, m), 7.83–7.95 and 8.10–8.20(total 1H, each m).

FAB-MS:649(M+H).

EXAMPLE 29

Preparation of (2S*,4S,5S)-4-[N-(carboxymethyl)-N-{(1R,2R)-1-methyl-2-(4-phenoxyphenyl)-4-phenylbutyl}carbamoyl]-2-(N,N-dimethylcarbamoyl)-1,3-dioxolane-2,5-dicarboxylic acid The above identified compound was obtained by carrying out the same reaction as in Example 28, except that instead of ethylamine hydrochloride used as the starting material in Example 25(2), dimethylamine hydrochloride was used.

$^1$H-NMR(CD$_3$COCD$_3$) δ:1.01 and 1.08(total 3H, each d, each J=6.7 Hz), 1.80–2.50(4H, m), 2.80–3.00(1H, m), 3.03 and 3.07 (total 6H, each s), 4.03(1H, d, J=17.0 Hz), 4.25(1H, d, J=17.0 Hz), 4.50–4.65(1H, m), 5.43, 5.63 and 6.05(total 2H, each d, each J=3.2 Hz), 7.00–7.25(11H, m), 7.35–7.43 (2H, m), 7.50–7.70(1H, m).

FAB-MS:649(M+H).

EXAMPLE 30

Preparation of (4S,5S)-4-[N-(carboxymethyl)-N-{(1R,2R)-1-methyl-2-(4-phenoxyphenyl)-4-phenylbutyl}carbamoyl]-2,2-bis(hydroxymethyl)-1,3-dioxolane-2,5-dicarboxylic acid The above identified compound was obtained by carrying out treatment in the same manner as in Example 27 except that instead of 2,2-bis{2-(trimethylsilyl)ethyl} (4S,5S)-4-[N-(benzyloxycarbonylmethyl)-N-{(1R,2R)-1-methyl-2-(4-phenoxyphenyl)-4-phenylbutyl}carbamoyl]-1,3-dioxolane-2,2,5-tricarboxylate used as the starting material in Example 27, 5-tert-butyl 2-ethyl (2R*,4S,5S)-4-[N-(tert-butoxycarbonylmethyl)-N-{(1R,2R)-1-methyl-2-(4-phenoxyphenyl)-4-phenylbutyl}carbamoyl]-1,3-dioxolane-2,2,5-tricarboxylate obtained in Example 20, was used, and then carrying out the same reaction as in Example 21.

$^1$H-NMR(CD$_3$COCD$_3$) δ:0.80–1.10(3H, m), 1.80–2.50 (4H, m), 2.80–2.95(1H, m), 3.40–3.90 and 4.15–4.65(total 7H, each m), 6.13–6.18, 6.30–6.40 and 6.48–6.50(total 2H, each m), 7.00–7.50(14H, m).

FAB-MS:594(M+H).

EXAMPLE 31

Preparation of (4S)-4-[N-(carboxymethyl)-N-{(1R*,2R*)-2-(3-methoxy-4-phenoxyphenyl)-1-methyl-4-phenylbutyl}carbamoyl]-1,3-dioxolane-2,2-dicarboxylic acid, and (4S)-4-[N-(carboxymethyl)-N-{(1S*,2S*)-2-(3-methoxy-4-phenoxyphenyl)-1-methyl-4-phenylbutyl}carbamoyl]-1,3-dioxolane-2,2-dicarboxylic acid (1) Preparation of 2,2-dimethyl (4S)-4-[N-(ethoxycarbonylmethyl)-N-{(1R*,2R*)-2-(3-methoxy-4-phenoxyphenyl)-1-methyl-4-phenylbutyl}carbamoyl]-1,3-dioxolane-2,2-dicarboxylate, and 2,2-diethyl (4S)-4-[N-

(ethoxycarbonylmethyl)-N-{(1S*,2S*)-2-(3-methoxy-4-phenoxyphenyl)-1-methyl-4-phenylbutyl}carbamoyl]-1,3-dioxolane-2,2-dicarboxylate The treatment was carried out in the same manner as in Example 19(1) except that instead of N-(tert-butoxycarbonylmethyl)-{(1R,2R)-1-methyl-4-phenyl-2-(4-phenoxyphenyl)butyl}amine used as the starting material in Example 19(1), N-(ethoxycarbonylmethyl)-{(1RS,2RS)-2-(3-methoxy-4-phenoxyphenyl)-1-methyl-4-phenylbutyl}amine obtained in Example 54 was used, and instead of 5-tert-butyl 2,2-diethyl (4R,5R)-1,3-dioxolane-2,2,4,5-tetracarboxylate, 2,2-diethyl (4S)-1,3-dioxolane-2,2,4-tricarboxylate obtained in Example 56, was used, and purification was carried out by medium pressure liquid chromatography (Lobar column™, Size A; hexane/ethyl acetate=2/1) to obtain the above identified compound as a preceding fraction of the medium pressure liquid chromatography named as (1R*,2R*)-isomer for the sake of convenience, and the above identified compound as a later fraction of the medium pressure liquid chromatography named as (1S*,2S*)-isomer for the sake of convenience, respectively, as colorless foams.

(2) Preparation of (4S)-4-[N-(carboxymethyl)-N-{(1R*,2R*)-2-(3-methoxy-4-phenoxyphenyl)-1-methyl-4-phenylbutyl}carbamoyl]-1,3-dioxolane-2,2-dicarboxylic acid, and (4S)-4-[N-(carboxymethyl)-N-{(1S*,2S*)-2-(3-methoxy-4-phenoxyphenyl)-1-methyl-4-phenylbutyl}carbamoyl]-1,3-dioxolane-2,2-dicarboxylic acid 29 mg and 25 mg of the compounds obtained in the above (1), were, respectively, dissolved in 1 ml of tetrahydrofuran separately, and 0.5 ml of an aqueous sodium hydroxide solution was added, followed by stirring at room temperature for 18 hours. The reaction solutions were acidified with 1N hydrochloric acid and then, extracted with ethyl ether and dried over anhydrous magnesium sulfate. The drying agent was filtered off, and then, solvent was distilled off under reduced pressure to obtain 24 mg (yield: 95%) of the above identified compound named as (1R*,2R*)-isomer for the sake of convenience, and 19 mg (yield: 89%) of the above identified compound named as (1S*,2S*)-isomer, respectively, as white solid.

(4S)-4-[N-(carboxymethyl)-N-{(1R*,2R*)-2-(3-methoxy-4-phenoxyphenyl)-1-methyl-4-phenylbutyl}carbamoyl]-1,3-dioxolane-2,2-dicarboxylic acid $^1$H-NMR(CD$_3$COCD$_3$) δ:0.99 and 1.12(total 3H, each d, each J=7.2 Hz), 1.79–3.02(5H, m), 3.50–4.68(8H, m), 5.38–5.42 and 5.65–5.73(total 1H, each m), 6.82–7.33(13H, m).

FAB-MS :608(M+H).

(4S)-4-[N-(carboxymethyl)-N-{(1S*,2S*)-2-(3-methoxy-4-phenoxyphenyl)-1-methyl-4-phenylbutyl}carbamoyl]-1,3-dioxolane-2,2-dicarboxylic acid $^1$H-NMR(CD$_3$COCD$_3$) δ:0.97–1.14(3H, m), 1.75–3.02(5H, m), 3.51–4.52(8H, m), 5.35–5.40 and 5.80–5.85(total 1H, each m), 6.83–7.33(13H, m).

FAB-MS:608(M+H).

EXAMPLE 32

Preparation of (4S)-4-[N-(carboxymethyl)-N-{(1R*,2R*)-2-(3-hydroxy-4-phenoxyphenyl)-1-methyl-4-phenylbutyl}carbamoyl]-1,3-dioxolane-2,2-dicarboxylic acid, and (4S)-4-[N-(carboxymethyl)-N-{(1S*,2S*)-2-(3-hydroxy-4-phenoxyphenyl)-1-methyl-4-phenylbutyl}carbamoyl]-1,3-dioxolane-2,2-dicarboxylic acid The same reaction as in Example 31(1) was carried out except that instead of N-(ethoxycarbonylmethyl)-{(1RS,2RS)-2-(3-methoxy-4-phenoxyphenyl)-1-methyl-4-phenylbutyl}amine used as the starting material in Example 31(1), N-(ethoxycarbonylmethyl)-{(1RS,2RS)-2-(3-benzyloxy-4-phenoxyphenyl)-1-methyl-4-phenylbutyl}amine obtained in Example 55 was used, and then the benzyl ether was converted to a hydroxy product by a conventional method, followed by the same treatment as in the above Example (2) to obtain the above identified compounds, respectively.

(4S)-4-[N-(carboxymethyl)-N-{(1R*,2R*)-2-(3-hydroxy-4-phenoxyphenyl)-1-methyl-4-phenylbutyl}carbamoyl]-1,3-dioxolane-2,2-dicarboxylic acid $^1$H-NMR(CD$_3$COCD$_3$) δ:0.96 and 1.12(total 3H, each d, each J=7.2 Hz), 1.79–2.95(5H, m), 3.50–5.03(5H, m), 5.38–5.42 and 5.71–5.76(total 1H, each m), 6.83–7.37(13H, m).

FAB-MS:594(M+H).

Preparation of (4S)-4-[N-(carboxymethyl)-N-{(1S*,2S*)-2-(3-hydroxy-4-phenoxyphenyl)-1-methyl-4-phenylbutyl}carbamoyl]-1,3-dioxolane-2,2-dicarboxylic acid $^1$H-NMR(CD$_3$COCD$_3$) δ:1.06 and 1.13(total 3H, each d, each J=7.2 Hz), 1.80–2.92(5H, m), 3.51–4.52(5H, m), 5.35–5.42 and 5.83–5.92(total 1H, each m), 6.82–7.37(13H, m).

FAB-MS:594(M+H).

EXAMPLE 33

Preparation of 2,2-diethyl (4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylate 18 mg of 5-tert-butyl 2,2-diethyl (4R,5R)-4-[N-(tert-butoxycarbonylmethyl)-N-{(1R,2R)-1-methyl-2-(4-phenoxyphenyl)-4-phenylbutyl}carbamoyl]-1,3-dioxolane-2,2,5-tricarboxylate (compound of Example 19(1)) was dissolved in 2 ml of formic acid, followed by stirring at room temperature for 3 days. Formic acid was distilled off under reduced pressure. Then, the residue was purified by medium pressure liquid chromatography (Lobar column™, Size A, RP-8, manufactured by Merck Co.; acetonitrile/0.1% trifluoroacetic acid aqueous solution=1/1→7/3) to obtain 8.5 mg (yield: 55%) of the above identified compound as a colorless oily substance.

$^1$H-NMR(CD$_3$COCD$_3$) δ:0.90–1.10(3H, m), 1.10–1.30(6H, m), 1.80–2.40(4H, m), 2.80–2.95(1H, m), 3.75–4.40(6H, m), 4,53–4.64(1H, m), 5.20–5.32 and 5.44–5.50(total 2H, each m), 7.00–7.50(14H, m).

FAB-MS:678(M+H).

EXAMPLE 34

Preparation of 2,2-diethyl (4S)-4-[N-(carboxymethyl)-N-{(1R 2R)-1-methyl-2-(4-phenoxyphenyl)-4-phenylbutyl}carbamoyl]-1,3-dioxolane-2,2-dicarboxylate The above identified compound was obtained by the same method as in Example 1 except that instead of N-(tert-butoxycarbonylmethyl)-{(1R,2R)-2-(2-fluoro-4-biphenylyl)-1-methyl-4-phenylbutyl}amine used as the starting material in Example 1, N-(tert-butoxycarbonylmethyl)-{(1R,2R)-1-methyl-2-(4-phenoxyphenyl)-4-phenylbutyl}amine obtained in Example 50, was used, and instead of 2,2-diethyl 1,2,2-cyclopropanetricarboxylate, 2,2,-diethyl (4S)-1,3-dioxolane-2,2,4-tricarboxylate obtained in Example 56, was used.

$^1$H-NMR(CD$_3$OD) δ:0.82 and 1.00(total 3H, each d, J=6.9 and 6.3 Hz), 1.15–1.35(6H, m), 1.65–2.60(5H, m), 3.40–4.70(9H, m), 4.88–5.12(1H, m), 6.90–7.40(14H, m).

FAB-MS:634(M+H).

EXAMPLE 35
Preparation of 2,2-diethyl (4R)-4-[N-(carboxymethyl)-N-{(1R,2R)-1-methyl-2-(4-phenoxyphenyl)-4-phenylbutyl}carbamoyl]-1,3-dioxolane-2,2-dicarboxylate The above identified compound was obtained by the same method as in Example 34 except that instead of 2,2-diethyl (4S)-1,3-dioxolane-2,2,4-tricarboxylate used as the starting material in Example 34, 2,2-diethyl (4R)-1,3-dioxolane-2,2,4-tricarboxylate, was used.

$^1$H-NMR(CD$_3$OD) δ:0.85–1.10(3H, m), 1.15–1.35(6H, m), 1.80–2.65(5H, m), 3.35–3.50, 3.90–4.65 and 4.95–5.05 (total 10H, m), 6.90–7.40(14H, m).

FAB-MS:634(M+H).

EXAMPLE 36
Preparation of 2,2-bis(pivaloyloxymethyl) (4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylate (1) Preparation of (4S)-4-[N-(tert- butoxycarbonylmethyl)-N-{(1R,2R)-1-methyl-2-(4-phenoxyphenyl)-4-phenylbutyl}carbamoyl]-1,3-dioxolane-2,2-dicarboxylic acid 4.98 g of N-(tert-butoxycarbonylmethyl)-{(1R,2R)-1-methyl-2-(4-phenoxyphenyl)-4-phenylbutyl}amine, 2.45 g of 2,2-diethyl (4S)-1,3-dioxolane-2,2,4-tricarboxylate, and 3.88 ml of triethylamine, were dissolved in 50 ml of chloroform, and a solution of 2.37 g of 2-chloro-1,3-dimethylimidazolinium chloride in 20 ml of chloroform, was added under cooling with ice, followed by stirring at the same temperature for one hour. The reaction solution was poured into water and extracted with chloroform. The extract solution was washed with a saturated sodium chloride aqueous solution and then, dried over anhydrous sodium sulfate. The drying agent was filtered off, and then, the solvent was distilled off under reduced pressure. The residue was purified by silica gel column chromatography (hexane/ethyl acetate=5/1) to obtain 4.98 g (yield: 81%) of a diethyl ester of the above identified compound as a colorless oily substance.

4.15 g of the above ester was dissolved in a mixed liquid comprising 200 ml of tetrahydrofuran and 200 ml of water, and 13 ml of a 1N sodium hydroxide aqueous solution was added, followed by stirring at room temperature for 12 hours. The reaction solution was acidified by an addition of 1N hydrochloric acid and then, extracted with ethyl ether. The extract solution was washed with a saturated sodium chloride aqueous solution and then dried over anhydrous magnesium sulfate to obtain 3.81 g (yield: quantitative) of the above identified compound as a colorless foam.

(2) Preparation of 2,2-bis(pivaloyloxymethyl) (4S)-4-[N-(tert-butoxycarbonylmethyl)-N-{(1R,2R)-1-methyl-2-(4-phenoxyphenyl)-4-phenylbutyl}carbamoyl]-1,3-dioxolane-2,2-dicarboxylate 1.0 g of (4S)-4-[N-(tert-butoxycarbonylmethyl)-N-{(1R,2R)-1-methyl-2-(4-phenoxyphenyl)-4-phenylbutyl}carbamoyl]-1,3-dioxolane-2,2-dicarboxylic acid was dissolved in 20 ml of ethanol, a solution having 514 mg of cesium carbonate dissolved in 5 ml of water, was added. The solvent was distilled off under reduced pressure. The residue was azeotropically distilled three times with toluene and dried. The obtained cesium salt was dissolved in 20 ml of dimethylformamide, and 1.91 g of pivaloyloxymethyl iodide was added, followed by stirring at room temperature for 2.5 hours. The reaction solution was poured into water and extracted with ethyl ether. The organic layer was dried over anhydrous magnesium sulfate. The drying agent was filtered off, and then, the solvent was distilled off under reduced pressure. The residue was purified by silica gel column chromatography (hexane/ethyl acetate=20/1→5/1) to obtain 926 mg (yield: 67%) of the above identified compound as a colorless oily substance.

(3) Preparation of 2,2-bis(pivaloyloxymethyl) (4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylate 926 mg of 2,2-bis(pivaloyloxymethyl) (4S)-4-[N-(tert-butoxycarbonylmethyl)-N-{(1R,2R)-1-methyl-2-(4-phenoxyphenyl)-4-phenylbutyl}carbamoyl]-1,3-dioxolane-2,2-dicarboxylate was dissolved in 12 ml of formic acid and left to stand at room temperature for 2 hours. Then, formic acid was distilled off under reduced pressure. The residue was purified by silica gel column chromatography (hexane/ethyl acetate=5/1→1/1) to obtain 723 mg (yield: 85%) of the above identified compound as a colorless foam.

$^1$H-NMR(CDCl$_3$) δ:0.85 and 1.03(total 3H, each d, J=6.3 and 6.5 Hz), 1.15–1.28(18H, m), 1.70–2.65(5H, m), 3.55–4.00 and 4.29–4.73(total 5H, m), 4.85–4.93 and 5.03–5.10(total 1H, each m), 5.65–5.85(4H, m), 6.95–7.40 (14H, m).

FAB-MS:806(M+H).

EXAMPLE 37
Preparation of 2-pivaloyloxymethyl (2S*,4S)-4-[N-{(1R 2R)-1-methyl-2-(4-phenoxyphenyl)-4-phenylbutyl}-N-(pivaloyloxymethoxycarbonylmethyl)carbamoyl]-1,3-dioxolane-2,2-dicarboxylate (1) Preparation of 2-benzyl (2R*,4S)-4-[N-(tert-butoxycarbonylmethyl)-N-{(1R,2R)-1-methyl-2-(4-phenoxyphenyl)-4-phenylbutyl}carbamoyl]-1,3-dioxolane-2,2-dicarboxylate, and 2-benzyl (2S*,4S)-4-[N-(tert-butoxycarbonylmethyl)-N-{(1R,2R)-1-methyl-2-(4-phenoxyphenyl)-4-phenylbutyl}carbamoyl]-1,3-dioxolane-2,2-dicarboxylate 1.0 g of (4S)-4-[N-(tert-butoxycarbonylmethyl)-N-{(1R,2R)-1-methyl-2-(4-phenoxyphenyl)-4-phenylbutyl}carbamoyl]-1,3-dioxolane-2,2-dicarboxylic acid (compound of Example 36(1)), 147 μl of benzyl alcohol and 657 μl of triethylamine, were dissolved in 20 ml of chloroform, and a solution of 400 mg of 2-chloro-1,3-dimethylimidazolinium chloride in 5 ml of chloroform, was added under cooling with ice, followed by stirring at the same temperature for one hour. The reaction solution was poured into water and extracted with chloroform. The extract solution was dried over anhydrous magnesium sulfate. The drying agent was filtered off, and then, the solvent was distilled off under reduced pressure. The residue was purified by medium pressure liquid chromatography (Lobar column™, Size C, RP-8, manufactured by Merck Co.; acetonitrile/0.1% trifluoroacetic acid aqueous solution=3/2→4/1→acetonitrile), to obtain 183 mg (yield: 16%) of the above identified compound as a preceding fraction of the medium pressure liquid chromatography named as (2S*, 4S)-isomer for the sake of convenience, and 591 mg (yield: 52%) of the above identified compound as a later fraction of the medium pressure liquid chromatography named as (2R*, 4S)-isomer for the sake of convenience, respectively, as colorless foams.

(2) Preparation of 2-benzyl (2R*,4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylate 200 mg of 2-benzyl (2R*,4S)-4-[N-(tert-butoxycarbonylmethyl)-N-{(1R,2R)-1-methyl-2-(4- phenoxyphenyl)-4-phenylbutyl}carbamoyl]-1,3-dioxolane-2,2-dicarboxylate was dissolved in 20 ml of formic acid, followed by stirring at room temperature for 2 hours. Formic acid was distilled off under reduced pressure, and the residue was azeotropically distilled with toluene to obtain 181 mg (yield: 98%) of the above identified compound as a white foam.

(3) Preparation of 2-pivaloyloxymethyl (2S*,4S)-4-[N-{(1R,2R)-1-methyl-2-(4-phenoxyphenyl)-4-phenylbutyl}-N-(pivaloyloxymethoxycarbonylmethyl)carbamoyl]-1,3-dioxolane-2,2-dicarboxylate 181 mg of 2-benzyl (2R*,4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylate was treated in the same manner as in Example 36(2) to obtain 158 mg (yield: 65%) of a benzyl ester of the above identified compound as a colorless oily substance. 153 mg of the above ester was dissolved in 3 ml of ethyl acetate, and 30 mg of a 10% palladium-carbon catalyst was added, followed by catalytic reduction for 30 minutes at room temperature under hydrogen normal pressure. The catalyst was filtered off, and then, the filtrate was evaporated to dryness under reduced pressure to obtain 136 mg (yield: quantitative) of the above identified compound.

$^1$H-NMR(CDCl$_3$) δ:0.79 and 0.95(total 3H, each d, J=6.5 and 6.3 Hz), 1.15–1.30(18H, m), 1.70–3.00(5H, m), 3.45–3.60, 3.65–3.75, 3.93–4.03 and 4.30–4.73(total 5H, m), 4.85–4.93 and 5.05–5.10(total 1H, each m), 5.65–5.85 (4H, m), 6.95–7.40(14H, m).

FAB-MS:806(M+H).

EXAMPLE 38

Preparation of 2-pivaloyloxymethyl (2R*,4S)-4-[N-{(1R,2R)-1-methyl-2-(4-phenoxyphenyl)-4-phenylbutyl}-N-(pivaloyloxymethoxycarbonylmethyl)carbamoyl]-1,3-dioxolane-2,2-dicarboxylate The above identified compound was obtained by carrying out treatment in the same manner as in Example 37(2) and (3) except that 2-benzyl (2S*,4S)-4-[N-(tert-butoxycarbonylmethyl)-N-{(1R,2R)-1-methyl-2-(4-phenoxyphenyl)-4-phenylbutyl}carbamoyl]-1,3-dioxolane-2,2-dicarboxylate obtained in Example 37(1) was used as the starting material.

$^1$H-NMR(CDCl$_3$) δ:0.72–1.03(3H, m), 1.05–1.35(18H, m), 1.69–2.60(5H, m), 3.43–4.59(5H, m), 4.80–5.00 and 5.10–5.20 (total 1H, each m), 5.64–5.91(4H, m), 6.93–7.41 (14H, m).

FAB-MS:806(M+H).

EXAMPLE 39

Preparation of 2-methyl (2S*,4S)-4-[N-{(1R,2R)-1-methyl-2-(4-phenoxyphenyl)-4-phenylbutyl}-N-(pivaloyloxymethoxycarbonylmethyl)carbamoyl]-1,3-dioxolane-2,2-dicarboxylate 2-benzyl (2R*,4S)-4-[N-(tert-butoxycarbonylmethyl)-N-{(1R,2R)-1-methyl-2-(4-phenoxyphenyl)-4-phenylbutyl}carbamoyl]-1,3-dioxolane-2,2-dicarboxylate obtained in Example 37(1) was methyl-esterified by means of an excess diazomethane, and then treated in the same manner as in Example 37(2) and (3) to obtain the above identified compound.

$^1$H-NMR(CDCl$_3$) δ:0.61–0.90(3H, m), 1.09 and 1.12 (total 9H, each s), 1.65–2.75(5H, m), 3.50 and 3.65(total 3H, each s), 3.48–3.88(2H, m), 4.17–4.45(3H, m), 4.95–5.05 and 5.25–5.34 (total 1H, each m), 5.60–5.85(2H, m), 6.85–7.38 (14H, m).

FAB-MS:706(M+H).

EXAMPLE 40

Preparation of 2-methyl (2R*,4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylate 18 mg of 2-benzyl 2-methyl (2R*,4S)-4-[N-(tert-butoxycarbonylmethyl)-N-{(1R,2R)-1-methyl-2-(4-phenoxyphenyl)-4-phenylbutyl}carbamoyl]-1,3-dioxolane-2,2-dicarboxylate obtained by methyl-esterifying 2-benzyl (2S*,4S)-4-[N-(tert-butoxycarbonylmethyl)-N-{(1R,2R)-1-methyl-2-(4-phenoxyphenyl)-4-phenylbutyl}carbamoyl]-1,3-dioxolane-2,2-dicarboxylate obtained in Example 37(1) by means of excess diazomethane, was dissolved in 1 ml of formic acid, followed by stirring at room temperature for one hour. Formic acid was distilled off under reduced pressure, and then, the residue was azeotropically distilled with toluene and then dissolved in 3 ml of 1,4-dioxane. 30 mg of a 10% palladium-carbon catalyst was added, followed by catalytic reduction for 30 hours at room temperature under hydrogen normal pressure. The catalyst was filtered off, and then, the filtrate was evaporated to dryness under reduced pressure to obtain 14 mg (yield: 98%) of the above identified compound.

$^1$H-NMR(CD$_3$COCD$_3$) δ:0.81–1.07(3H, m), 1.80–2.47 (5H, m), 3.67 and 3.72(total 3H, each s), 3.83(1H, d, J=16.8 Hz), 4.07(1H, d, J=16.8 Hz), 4.32–4.76(3H, m), 4.93–4.98 and 5.33–5.38(total 1H, each m), 6.99–7.47(14H, m).

FAB-MS:592(M+H).

EXAMPLE 41

Preparation of 2-methyl (2S*,4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylate The above identified compound was obtained by carrying out the same reaction as in Example 40 except that 2-benzyl (2R*,4S)-4-[N-(tert-butoxycarbonylmethyl)-N-{(1R,2R)-1-methyl-2-(4-phenoxyphenyl)-4-phenylbutyl}carbamoyl]-1,3-dioxolane-2,2-dicarboxylate prepared in Example 37(1) was used.

$^1$H-NMR(CD$_3$COCD$_3$) δ:0.94 and 1.09(total 3H, each d, each J=7.2 Hz), 1.82–3.02(5H, m), 3.76 and 3.77(total 3H, each s), 3.92–4.66(5H, m), 5.33–5.42 and 5.70–5.80(total 1H, each m), 6.99–7.27(10H, m), 7.32–7.48(4H, m).

FAB-MS:592(M+H).

EXAMPLE 42

Preparation of (4S)-4-[N-(carboxymethyl)-N-{(1R,2R)-2-(2-fluoro-4-biphenylyl)-1-methyl-4-phenylbutyl}carbamoyl]-1,3-dioxolane-2,2-dicarboxylic acid The above identified compound was obtained by the same method as in Example 9.

$^1$H-NMR(CD$_3$COCD$_3$) δ:1.01 and 1.13(total 3H, each d, each J=7.5 Hz), 1.93–3.12(5H, m), 3.98–4.74(5H, m), 5.38–5.43 and 5.73–5.80(total 1H, each m), 7.10–7.65(13H, m).

FAB-MS:580(M+H).

Compounds of Examples 43 to 47 were obtained by the same method as in Example 31.

EXAMPLE 43

(4S)-4-[N-(carboxymethyl)-N-{(1R*,2R*)-1-methyl-2-(4-phenoxyphenyl)-4-(3-thienyl)butyl}carbamoyl]-1,3-dioxolane-2,2-dicarboxylic acid $^1$H-NMR(CD$_3$COCD$_3$) δ:0.80–1.20(3H, m), 1.80–3.20 (5H, m), 3.40–4.75(5H, m), 5.28–5.40 and 5.70–5.80(total 1H, each m), 6.80–7.50(12H, m).

FAB-MS:582(M–H).

EXAMPLE 44

(4S)-4-[N-(carboxymethyl)-N-{(1R*,2R*)-2-(4-phenoxyphenyl)-1-methyl-3-(3,4-methylenedioxyphenyl) propyl}carbamoyl]-1,3-dioxolane-2,2-dicarboxylic acid ¹H-NMR(CD₃COCD₃) δ:1.03 and 1.18(total 3H, each d, each J=6.5 Hz), 2.68–3.40(3H, m), 4.10–4.70(5H, m), 5.42–5.48 and 5.83–5.93(total 3H, each m), 6.35–6.60(3H, m), 6.85–7.40(9H, m).

FAB-MS:608(M+H).

EXAMPLE 45

(4S)-4-[N-(carboxymethyl)-N-{(1S*,2S*)-2-(4-phenoxyphenyl)-1-methyl-3-(3,4-methylenedioxyphenyl)propyl}carbamoyl]-1,3-dioxolane-2,2-dicarboxylic acid ¹H-NMR(CD₃COCD₃) δ:1.01 and 1.16(total 3H, each d, each J=6.5 Hz), 2.68–2.86 and 3.10–3.52(total 3H, each m), 4.10–4.86 (5H, m), 5.42–5.48 and 5.80–5.83(total 1H, each m), 5.89(2H, brs), 6.38–6.60(3H, m), 6.85–7.45(9H, m).

FAB-MS:608(M+H).

EXAMPLE 46

(4S)-4-[N-(carboxymethyl)-N-{(1R*,2R*)-3-(benzo[b]thienyl)-2-(4-biphenylyl)-1-methylpropyl}carbamoyl]-1,3-dioxolane-2,2-dicarboxylic acid ¹H-NMR(CD₃COCD₃) δ:1.04 and 1.18(total 3H, each d, J=6.4 and 6.6 Hz), 3.20–4.00(3H, m), 4.20–4.80(5H, m), 5.47 and 5.85(total1H, each dd, J=2.6, 6.9 Hz and 2.6, 6.5 Hz), 6.90–7.80 (14H, m). p FAB-MS:604(M+H).

EXAMPLE 47

(4S)-4-[N-(carboxymethyl)-N-{(1S*,2S*)-3-(benzo[b]thienyl)-2-(4-biphenylyl)-1-methylpropyl}carbamoyl]-1,3-dioxolane-2,2-dicarboxylic acid ¹H-NMR(CD₃COCD₃) δ:1.00–1.10 and 1.19(total 3H, m and d, J=6.5 Hz), 3.30–3.60, 3.85–3.87 and 4.15–4.75(total 8H, each m), 5.47 and 6.00(total 1H, each dd, J=2.4, 6.9 Hz and 2.4, 6.5 Hz), 6.90–7.73(14H, m).

FAB-MS :604(M+H).

EXAMPLE 48

Preparation of (4S)-4-[N-(carboxymethyl)-N-{(1R,2R)-2-{4-(4-bromophenoxy)phenyl}-1-methyl-4-phenylbutyl}carbamoyl]-1,3-dioxolane-2,2-dicarboxylic acid The above identified compound was obtained by the same method as in Example 9.

¹H-NMR(CD₃COCD₃) δ:0.95 and 1.09(total 3H, each d, each J=6.3 and 6.6 Hz), 1.80–2.45(4H, m), 2.80–3.10(1H, m), 3.98–4.70(5H, m), 5.38–5.43 and 5.73–5.80(total 1H, each m), 7.10–7.65(13H, m).

FAB-MS:657(M+H).

EXAMPLE 49

Preparation of N-(ethoxycarbonylmethyl)-{(1R,2R)-1-methyl-2-(4-phenoxyphenyl)-4-phenylbutyl}amine (1) Preparation of 4-phenoxyphenylacetone 75.0 g of 4-bromodiphenyl ether, 129 ml of tributyltin methoxide, 45.0 g of isopropenyl acetate and 2,47 g of dichlorobis{tri(o-tolyl)phosphine}palladium, were dissolved in 300 ml of toluene and refluxed under heating for 3 hours. The reaction solution was left to cool to room temperature, and then, a saturated potassium fluoride aqueous solution was added, followed by stirring for one hour. Then, the product was subjected to celite filtration and washed with ethyl acetate. The filtrate and washing liquid were put together. Then, the organic layer was separated and washed with a saturated sodium chloride aqueous solution and then dried over anhydrous magnesium sulfate. The drying agent was filtered off, and then, the solvent was distilled off under reduced pressure. The residue was purified by silica gel column chromatography (hexane/ethyl acetate=15/1→10/1) to obtain 56.3 g (yield: 83%) of the above identified compound as yellow solid.

¹H-NMR(CDCl₃)δ:2.18(3H, s), 3.67(2H, s), 6.90–7.40 (9H, m).

(2) Preparation of 3-(4-phenoxyphenyl)-5-phenylpentan-2-one 11.2 g of 60% oily sodium hydride was suspended in 200 ml of dimethylformamide, and a solution of 56.0 g of 4-phenoxyphenylacetone in 100 ml of dimethylformamide, was added under cooling with ice with stirring, followed by stirring at the same temperature for 5 minutes and at room temperature for 30 minutes. Then, the reaction solution was again cooled with ice, and 52.0 g of phenethyl bromide was added. The reaction solution was gradually returned to room temperature and then stirred for 30 minutes, and water was added to the reaction solution, followed by extraction with ethyl ether. The organic layer was washed with a saturated sodium chloride aqueous solution and then dried over anhydrous magnesium sulfate. The drying agent was filtered off, and then, the solvent was distilled off under reduced pressure. The residue was purified by silica gel column chromatography (hexane/ethyl acetate=10/1) to obtain 50.6 g (yield: 61%) of the above identified compound as a pale yellow oily substance.

¹H-NMR(CDCl₃) δ:1.90–2.10(1H, m), 2.05(3H, s), 2,25–2.60 (3H, m), 2.68(1H, dd, J=6.8, 7.9 Hz), 6.95–7.40 (14H, m).

(3) Preparation of (2RS,3SR)-3-(4-phenoxyphenyl)-5-phenylpentan-2-ol 50.6 g of 3-(4-phenoxyphenyl)-5-phenylpentan-2-one was dissolved in 1280 ml of tetrahydrofuran, and 180 ml of a 1M tetrahydrofuran solution of tri-sec-butyllithium borohydride was added under cooling to −78° C. with stirring, followed by stirring at the same temperature for one hour. To the reaction solution, 224 ml of a 4N sodium hydroxide aqueous solution was added under cooling with ice with stirring, and then 118 ml of a 30% hydrogen peroxide aqueous solution was gradually dropwise added, followed by stirring at 0° C. for one hour. Ethyl ether and water were added to the reaction solution, followed by extraction. The organic layer was washed with a saturated sodium thiosulfate aqueous solution and a saturated sodium chloride aqueous solution and then dried over anhydrous magnesium sulfate. The drying agent was filtered off, and then, the solvent was distilled off under reduced pressure. The residue was purified by silica gel column chromatography (hexane/ethyl acetate=5/1) to obtain 47.2 g (yield: 95%) of the above identified compound as a colorless oily substance.

¹H-NMR(CDCl₃) δ:1.18(3H, d, J=6.6 Hz), 1.28(1H, d, J=3.8 Hz), 1.88–2.13(2H, m), 2.35–2.60(3H, m), 3.83–3.95 (1H, m), 6.95–7.40(14H, m).

(4) Preparation of (2S,3R)-3-(4-phenoxyphenyl)-5-phenylpentan-2-ol 47.2 g of (2RS,3SR)-3-(4-phenoxyphenyl)-5-phenylpentan-2-ol was dissolved in 470 ml of vinyl acetate, and 19.4 ml of triethylamine was added. Then, 4.7 g of immobilized lipase (Toyothium LIP) was added, followed by stirring at 30° C. for 2 days. The enzyme was filtered off and then, washed with ethyl acetate. The filtrate and the washing liquid were put together, and the solvent was distilled off under reduced pressure. The residue was purified by silica gel column chromatography (hexane/ethyl acetate=10/1→5/1) to obtain 23.8 g of (2R,3S)-2-acetoxy-3-(4-phenoxyphenyl)-5-phenylpentane and 22.2 g of the above identified compound, respectively, as colorless oily substances. Further, the absolute configuration of the above-identified compound was determined by Mosher method (J. Am. Chem. Soc., vol. 113, p. 4092 (1991)).

(2S,3R)-3-(4-phenoxyphenyl)-5-phenylpentan-2-ol $^1$H-NMR(CDCl$_3$) δ:1.18(3H, d, J=6.6 Hz), 1.28(1 H, d, J=3.8 Hz), 1.88–2.13(2H, m), 2.35–2.60(3H, m), 3.83–3.95 (1H, m), 6.95–7.40(14H, m).

(2R,3S)-2-acetoxy-3-(4-phenoxyphenyl)-5-phenylpentane $^1$H-NMR(CDCl$_3$) δ:1.12(3H, d, J=6.6 Hz), 1.96(3H, s), 1.85–2.20(2H, m), 2.30–2.60(2H, m), 2.68–2.78(1H, m), 5.10–5.20(1H, m), 6.95–7.40(14H, m).

(5) Preparation of (1R,2R)-2-(4-phenoxyphenyl)-1-methyl-4-phenylbutylamine 22.2 g of (2S,3R)-3-(4-phenoxyphenyl)-5-phenylpentan-2-ol and 26.3 of triphenylphosphine were dissolved in 200 ml of tetrahydrofuran, and 17.5 g of diethyl azodicarboxylate and then 27.0 g of diphenylphosphoryl azide were added under cooling with ice in a nitrogen atmosphere. Then, the mixture was returned to room temperature and stirred for 3 hours. The solvent was distilled off under reduced pressure and the residue was roughly purified by silica gel column chromatography (hexane/ethyl acetate=15/1) to obtain a crude azide product.

The above azide product was refluxed under heating for 8 hours in 440 ml of 10% water-containing tetrahydrofuran together with 17.5 g of triphenylphosphine. The reaction solution was concentrated under reduced pressure. Then, the residue was purified by silica gel column chromatography (hexane/ethyl acetate=10/1→ethyl acetate→chloroform/methanol=10/1) to obtain 15.6 g (yield: 71%) of the above identified compound as a colorless oily substance.

$^1$H-NMR(CDCl$_3$) δ:0.93(3H, d, J=6.5 Hz), 1.85–2.20(2H, m), 2.30–2.55(3H, m), 3.02(1H, qint., J=6.6 Hz), 6.90–7.38 (14H, m).

(6) Preparation of N-(ethoxycarbonylmethyl)-{(1R,2R)-2-(4-phenoxyphenyl)-1-methyl-4-phenylbutyl}amine 2.20 g of (1R,2R)-2-(4-phenoxyphenyl)-1-methyl-4-phenylbutylamine was dissolved in 30 ml of dimethylformamide, and 1.00 g of potassium carbonate was added. Then, 0.77 ml of ethyl bromoacetate was added at room temperature, followed by stirring for 3 hours. The reaction solution was poured into water and extracted with ethyl acetate. The organic layer was washed with water and a saturated sodium chloride aqueous solution and then, dried over anhydrous magnesium sulfate. The drying agent was filtered off, and then, the solvent was distilled off under reduced pressure, and the residue was purified by silica gel column chromatography (hexane/ethyl acetate=3/1) to obtain 2.27 g (yield: 83%) of the above identified compound as a colorless oily substance.

$^1$H-NMR(CDCl$_3$) δ:0.88(3H, d, J=6.3 Hz), 1.26(3H, t, J=7.1 Hz), 1.85–2.63(5H, m), 2.73–2.83(1H, m), 3.40(2H, s), 4.17 (2H, q, J=7.1 Hz), 6.96–7.34(14H, m).

Compounds of Examples 50 to 53 were obtained by carrying out the same reaction as in Example 49 except that instead of ethyl bromoacetate used in Example 49(6), the corresponding bromoacetic acid esters were used.

EXAMPLE 50

N-(tert-butoxycarbonylmethyl)-{(1R,2R)-1-methyl-2-(4-phenoxyphenyl)-4-phenylbutyl}amine $^1$H-NMR(CDCl$_3$) δ:0.88(3H, d, J=6.3 Hz), 1.45(9H, s), 1.85–2.63(5H, m), 2.77(1H, quint., J=6.3 Hz), 3.25(1H, d, J=16.2 Hz), 3.35(1H, d, J=16.2 Hz), 6.90–7.40(14H, m).

EXAMPLE 51

N-(methoxycarbonylmethyl)-{(1R,2R)-1-methyl-2-(4-phenoxyphenyl)-4-phenylbutyl}amine $^1$H-NMR(CDCl$_3$) δ:0.88(3H, d, J=6.4 Hz), 1.90–2.65(5H, m), 2.78(1H, quint., J=6.4 Hz), 3.38(1H, d, J=17.0 Hz), 3.45(1H, d, J=17.0 Hz), 3.71(3H, s), 6.95–7.35(14H, m).

EXAMPLE 52

N-(benzyloxycarbonylmethyl)-{(1R,2R)-1-methyl-2-(4-phenoxyphenyl)-4-phenylbutyl}amine $^1$H-NMR(CDCl$_3$) δ:0.87(3H, d, J=6.4 Hz), 1.85–2.65(5H, m), 2.77(1H, quint., J=6.4 Hz), 3.42(1H, d, J=17.0 Hz), 3.48(1H, d, J=17.0 Hz), 5.10–5.20(2H, m), 6.90–7.40(19H, m).

EXAMPLE 53

N-(ethoxycarbonylmethyl)-[(1R,2R)-1-methyl-2-{4-(4-bromophenoxy)phenyl}-4-phenylbutyl]amine $^1$H-NMR(CDCl$_3$) δ:0.88(3H, d, J=6.4 Hz), 1.26(3H, t, J=7.0 Hz), 1.88–2.54(5H, m), 2.78(1H, quint., J=6.4 Hz), 3.38(1H, d, J=16.9 Hz), 3.42(1H, d, J=16.9 Hz), 4.17(2H, q, J=7.0 Hz), 6.85–7.00(4H, m), 7.05–7.30(7H, m), 7.40–7.48 (2H, m).

EXAMPLE 54

Preparation of N-(ethoxycarbonylmethyl)-{(1RS,2RS)-2-(3-methoxy-4-phenoxyphenyl)-1-methyl-4-phenylbutyl}amine (1) Preparation of 3-methoxy-4-phenoxybenzaldehyde 6.0 g of 4-hydroxy-3-methoxybenzaldehyde, 75 ml of pyridine, 12.0 g of iodobenzene, 10.9 g of potassium carbonate and 6.24 g of cupric oxide were mixed and heated at 145° C. for 18 hours in a sealed tube. The reaction solution was left to cool to room temperature and then diluted with ethyl acetate and subjected to celite filtration. The filtrate was distilled off under reduced pressure, and the residue was purified by silica gel column chromatography (hexane/ethyl acetate=3/1) to obtain 1.11 g (yield: 12%) of the above identified compound as a colorless oily substance.

(2) Preparation of 1-(3-methoxy-4-phenoxyphenyl)-2-nitropropene 1.15 g of 3-methoxy-4-phenoxybenzaldehyde, 96 μl of n-butylamine, 10 ml of nitroethane and 5 ml of toluene were mixed and refluxed under heating for 2 hours. The reaction solution was left to cool to room temperature and then, the solvent was distilled off under reduced pressure. The residue was purified by silica gel column chromatography (hexane/ethyl acetate=20/1) to obtain 953 mg (yield: 69%) of the above identified compound as a colorless oily substance.

(3) Preparation of 3-methoxy-4-phenoxyphenylacetone 953 mg of 1-(3-methoxy-4-phenoxyphenyl)-2-nitropropene, 1.31 g of iron, 9.5 mg of ferric chloride and 5 ml of water were mixed, and 1.5 ml of 6N hydrochloric acid was dropwise added over a period of 1.5 hours under reflux and heating. The reaction solution was subjected to celite filtration, and the filtrate was extracted with ethyl acetate. The extract solution was washed with a saturated sodium hydrogen carbonate aqueous solution and then, dried over anhydrous sodium sulfate. The drying agent was filtered off, and then, the solvent was distilled off under reduced pressure. The residue was purified by silica gel column chromatography (hexane/ethyl acetate=10/1) to obtain 688 mg (yield: 80%) of the above identified compound as a colorless oily substance.

(4) Preparation of (1RS,2RS)-2-(3-methoxy-4-phenoxyphenyl)-1-methyl-4-phenylbutylamine The above identified compound was obtained by carrying out the same reaction as in Example 49(2), (4) and (5) except that instead of 4-phenoxyphenylacetone used as the starting material in Example 49(2), 3-methoxy-4-phenoxyphenylacetone was used.

$^1$H-NMR(CDCl$_3$) δ:0.95(3H, d, J=6.4 Hz), 1.85–2.00(1H, m), 2.10–2.23(1H, m), 2.30–2.56(3H, m), 3.04(1H, quint., J=6.4 Hz), 3.83(3H, s), 6.70–6.80(2H, m), 6.90–7.32(11H, m).

(5) Preparation of N-(ethoxycarbonylmethyl)-{(1RS,2RS)-2-(3-methoxy-4-phenoxyphenyl)-1-methyl-4-phenylbutyl}amine The above identified compound was obtained by carrying out treatment in the same manner as in Example 49(6) except that instead of (1R,2R)-2-(4-phenoxyphenyl)-1-methyl-4-phenylbutylamine used as the starting material in Example 49(6), (1RS,2RS)-2-(3-methoxy-4-phenoxyphenyl)-1-methyl-4-phenylbutylamine was used.

$^1$H-NMR(CDCl$_3$) δ:0.90(3H, d, J=6.3 Hz), 1.26(3H, t, J=7.1 Hz), 1.88–2.05(1H, m), 2.15–2.28(1H, m), 2.35–2.63 (3H, m), 2.79(1H, qint., J=6.3 Hz), 3.38(1H, d, J=16.9 Hz), 3.43(1H, d, J=16.9 Hz), 3.84(3H, s), 4.18(2H. q. J=7.1 Hz), 6.70–6.83(2H, m), 6.90–7.35(11H, m).

EXAMPLE 55

Preparation of N-(ethoxycarbonylmethyl)-{(1RS,2RS)-2-(3-benzyloxy-4-phenoxyphenyl)-1-methyl-4-phenylbutyl}amine (1) Preparation of (2RS,3SR)-2-acetoxy-3-(3-benzyloxy-4-phenoxyphenyl)-5-phenylpentane 380 mg of (2RS,3SR)-3-(3-methoxy-4-phenoxyphenyl)-5-phenylpentan-2-ol as an intermediate of Example 54(4), was dissolved in 5 ml of pyridine, and 1 ml of acetic anhydride and then 10 mg of dimethylaminopyridine were added, followed by stirring at room temperature for 30 minutes. The reaction solution was poured into water and extracted with ethyl ether. Then, the extract solution was sequentially washed with 1N hydrochloric acid, a saturated sodium hydrogen carbonate aqueous solution and a saturated sodium chloride aqueous solution, and then dried over anhydrous sodium sulfate. The drying agent was filtered off, and then, the solvent was distilled off under reduced pressure to obtain 466 mg (yield: quantitative) of the above identified compound as a colorless oily substance.

(2) (2RS,3SR)-2-acetoxy-3-(3-hydroxy-4-phenoxyphenyl)-5-phenylpentane 200 mg of (2RS,3SR)-2-acetoxy-3-(3-benzyloxy-4-phenoxyphenyl)-5-phenylpentane was dissolved in 5 ml of methylene chloride, and 0.2 ml of boron tribromide was added under cooling to −78° C., followed by stirring at the same temperature for 3 hours. Then, the temperature was gradually brought to 0° C. The reaction solution was poured into a saturated sodium hydrogen carbonate aqueous solution and extracted with ethyl acetate and then washed with a saturated sodium chloride aqueous solution and dried over anhydrous sodium sulfate. The drying agent was filtered off, and then, the solvent was distilled off under reduced pressure. The residue was purified by silica gel column chromatography (hexane/ethyl acetate=10/1→5/1), to obtain 161 mg (yield: 85%) of the above identified compound as a colorless oily substance.

(3) Preparation of (2RS,3SR)-3-(3-benzyloxy-4-phenoxyphenyl)-5-phenylpentan-2-ol 160 mg of (2RS,3SR)-2-acetoxy-3-(3-hydroxy-4-phenoxyphenyl)-5-phenylpentane was dissolved in 5 ml of methanol, and 2.5 ml of a 1N sodium hydroxide aqueous solution was added, followed by stirring at room temperature for 3.5 hours. The reaction solution was concentrated under reduced pressure, and then, the residue was neutralized with 1N hydrochloric acid and extracted with ethyl acetate. The extract solution was washed with a saturated sodium chloride aqueous solution and then dried over anhydrous sodium sulfate. The drying agent was filtered off. The solvent was distilled off under reduced pressure, and the obtained residue was dissolved in 1 ml of methyl ethyl ketone. The solution was added to a suspension having 116 mg of potassium carbonate preliminarily suspended in 3 ml of methyl ethyl ketone, and 58 μl of benzyl bromide was further added at room temperature, followed by stirring under heating at 100° C. for 4 hours. The reaction solution was left to cool, then neutralized with 1N hydrochloric acid and extracted with ethyl acetate. The extract solution was washed with a saturated sodium chloride aqueous solution and then dried over anhydrous sodium sulfate. The drying agent was filtered off. The residue was purified by silica gel column chromatography (hexane/ethyl acetate=5/1) to obtain 173 mg (yield: 96%) of the above identified compound as a colorless oily substance.

$^1$H-NMR(CDCl$_3$) δ:1.13(3H, d, J=6.4 Hz), 1.21(1H, d, J=3.2 Hz), 1.80–2.05(2H, m), 2.30–2.50(3H, m), 3.80–3.92 (1H, m), 5.08(2H, s)6.78–7.35(18H, m).

(4) Preparation of N-(ethoxycarbonylmethyl)-{(1RS,2RS)-2-(3-benzyloxy-4-phenoxyphenyl)-1-methyl-4-phenylbutyl}amine The above identified compound was obtained by carrying out the same reaction as in Example 49(5) and (6) except that instead of (2RS,3SR)-3-(4-phenoxyphenyl)-5-phenylpentan-2-ol used as the starting material in Example 49(2), (2RS,3SR)-3-(3-benzyloxy-4-phenoxyphenyl)-5-phenylpentan-2-ol was used.

$^1$H-NMR(CDCl$_3$) δ:0.83(3H, d, J=6.3 Hz), 1.15(3H, t, J=7.2 Hz), 1.80–1.85(1H, m), 2.05–2.20(1H, m), 2.25–2.55 (3H, m), 2.73(1H, qint., J=6.3 Hz), 3.35(1H, d, J=17.0 Hz), 3.38(1H, d, J=17.0 Hz), 4.12(2H, q, J=6.3 Hz), 5.08(2H, s), 6.70–6.80(2H, m), 6.90–7.0(16H, m).

EXAMPLE 56

Preparation of 2,2-diethyl (4S)-1,3-dioxolane-2,2,4-tricarboxylate (1) Preparation of (2R)-2-bromo-3-hydroxypropionic acid 24.0 g of D-serine and 95.0 g of potassium bromide were dissolved in 450 ml of a 2.5N sulfuric acid aqueous solution, and 25 ml of an aqueous solution containing 25.4 g of sodium nitrite was dropwise added over a period of 15 minutes under cooling with ice. After stirring at the same temperature for 45 minutes, stirring was continued at room temperature for one hour. The reaction solution was extracted with ethyl ether. The obtained organic layer was washed with a saturated sodium chloride aqueous solution and then, dried over anhydrous sodium sulfate. The solvent was distilled off under reduced pressure to obtain 18.1 g (yield: 47%) of the above identified compound as a yellow oily substance.

$^1$H-NMR(CD$_3$OD) δ:3.80(1H, dd, J=6.8 and 12.6 Hz), 3.95(1H, dd, J=7.9 and 12.6 Hz), 4.24(1H, dd, J=6.8 and 7.9 Hz).

(2) Preparation of tert-butyl (2R)-2-bromo-3-hydroxypropionate 18.1 g of (2R)-2-bromo-3-hydroxypropionic acid and 200 ml of chloroform were mixed, and 53.6 g of O-tert-butyl-N,N-diisopropylisourea was added under cooling with ice, followed by stirring at room temperature for 15 hours. Insoluble matters were filtered off, and then, the filtrate was concentrated under reduced pressure. The residue was purified by silica gel column chromatography (hexane/ethyl acetate=10/1→5/1) to obtain 14.7 g (yield: 61%) of the above identified compound as a colorless oily substance.

$^1$H-NMR(CDCl$_3$) δ:1.48(9H, s), 2.43(1H, t, J=7.6 Hz), 3.80–4.20(2H, m), 4.25(1H, t, J=6.3 Hz).

(3) Preparation of 4-tert-butyl 2,2-diethyl (4S)-1,3-dioxolane-2,2,4-tricarboxylate 6.90 g of tert-butyl (2R)-2-bromo-3-hydroxypropionate and 5.3 g of diethyl ketomalonate were mixed, and after the heat-generated reaction solution returned to room temperature, 15 ml of hexane and 6.4 g of potassium carbonate were sequentially added, followed by stirring at room temperature for 15 hours. Water was added to the reaction solution, followed by extraction with ethyl ether.

The obtained organic layer was washed with water and a saturated sodium chloride aqueous solution, and then dried over anhydrous magnesium sulfate. The drying agent was filtered off, and then, the solvent was distilled off under reduced pressure. The residue was purified by silica gel column chromatography (hexane/ethyl acetate=10/1→5/1) to obtain 8.0 g (yield: 83%) of the above identified compound as a colorless oily substance.

$^1$H-NMR(CDCl$_3$) δ:1.23–1.40(6H, m), 1.46(9H, s), 4.20–4.48 (6H, m), 4.75(1H, dd, J=6.0, 7.3 Hz).

(4) Preparation of 2,2-diethyl (4S)-1,3-dioxolane-2,2,4-tricarboxylate 3.0 g of 4-tert-butyl 2,2-diethyl (4S)-1,3-dioxolane-2,2,4-tricarboxylate was dissolved in 30 ml of formic acid, followed by stirring at room temperature for 6 hours. Formic acid was distilled off under reduced pressure, and the residue was purified by silica gel column chromatography (hexane/ethyl acetate=3/1→1/1) to obtain 2.35 g (yield: 98%) of the above identified compound as a colorless oily substance.

$^1$H-NMR(CDCl$_3$) δ:1.30–1.43(6H, m), 4.25–4.60(6H, m), 4.89 (1H, dd, J=5.3 and 6.8 Hz).

$[α]^{20}_D$-3.60° (c=1.000, CDCl$_3$).

Compounds of Examples 57 to 67 were obtained by carrying out the same reaction as in Example 56 except that instead of D-serine used as the starting material in Example 56, the corresponding amino acids were used.

EXAMPLE 57
2,2-diethyl (4R)-1,3-dioxolane-2,2,4-tricarboxylate $^1$H-NMR(CDCl$_3$) δ:1.30–1.43(6H, m), 4.25–4.60(6H, m), 4.89 (1H, dd, J=5.3, 6.8 Hz).

EXAMPLE 58
4-tert-butyl 2,2-diethyl (4S,5S)-5-methyl-1,3-dioxolane-2,2,4-tricarboxylate $^1$H-NMR(CDCl$_3$) δ:1.29(3H, t, J=7.2 Hz), 1.34(3H, t, J=7.1 Hz), 1.37(3H, d, J=6.4 Hz), 1.47(9H, s), 4.20–4.40 (4H, m), 4.18(1H, d, J=6.4 Hz), 4.75(1H, qint., J=6.4 Hz).

$[α]^{20}_D$-11.6° (c=1.000, CDCl$_3$).

EXAMPLE 59
2,2-diethyl (4S,5S)-5-methyl-1,3-dioxolane-2,2,4-tricarboxylate $^1$H-NMR(CDCl$_3$) δ:1.33(3H, t, J=6.9 Hz), 1.36(3H, t, J=7.0 Hz), 1.45(3H, d, J=6.0 Hz), 4.20–4.50(4H, m), 4.73–4.82(2H, m).

EXAMPLE 60
4-tert-butyl 2,2-diethyl (4R,5R)-5-methyl-1,3-dioxolane-2,2,4-tricarboxylate $^1$H-NMR(CDCl$_3$) δ:1.29(3H, t, J=7.2 Hz), 1.34(3H, t, J=7.1 Hz), 1.37(3H, d, J=6.4 Hz), 1.47(9H, s), 4.20–4.40 (4H, m), 4.18 (1H, d, J=6.4 Hz), 4.75(1H, qint., J=6.4 Hz).

$[α]^{20}_D$+9.80° (c=1.000, CDCl$_3$).

EXAMPLE 61
2,2-diethyl (4S,5S)-5-methyl-1,3-dioxolane-2,2,4-tricarboxylate $^1$H-NMR(CDCl$_3$) δ:1.33(3H, t, J=6.9 Hz), 1.36(3H, t, J=7.0 Hz), 1.45(3H, d, J=6.0 Hz), 4.20–4.50(4H, m), 4.73–4.82(2H, m).

EXAMPLE 62
4-tert-butyl 2,2-diethyl (4R,5S)-5-methyl-1,3-dioxolane-2,2,4-tricarboxylate $^1$H-NMR(CDCl$_3$) δ:1.30(3H, t, J=7.1 Hz), 1.31(3H, t, J=7.1 Hz), 1.47(9H, s), 1.49(3H, d, J=6.1 Hz), 4.20–4.40 (5H, m), 4.75 (1H, qint., J=6.1 Hz).

$[α]^{20}_D$+50.2° (c=1.000, CHCl$_3$).

EXAMPLE 63
2,2-diethyl (4R,5S)-5-methyl-1,3-dioxolane-2,2,4-tricarboxylate $^1$H-NMR(CDCl$_3$) δ:1.30(6H, t, J=6.9 Hz), 1.50(3H, d, J=6.0 Hz), 4.20–4.82(6H, m).

EXAMPLE 64
4-tert-butyl 2,2-diethyl (4S,5R)-5-methyl-1,3-dioxolane-2,2,4-tricarboxylate $^1$H-NMR(CDCl$_3$) δ:1.30(3H, t, J=7.1 Hz), 1.31(3H, t, J=7.1 Hz), 1.47(9H, s), 1.49(3H, d, J=6.1 Hz), 4.20–4.40 (5H, m), 4.75 (1H, qint., J=6.1 Hz).

$[α]^{20}_D$+51.8° (c=1.000, CHCl$_3$).

EXAMPLE 65
2,2-diethyl (4S,5R)-5-methyl-1,3-dioxolane-2,2,4-tricarboxylate $^1$H-NMR(CDCl$_3$) δ:1.30(6H, t, J=6.9 Hz), 1.50(3H, d, J=6.0 Hz), 4.20–4.82(6H, m).

EXAMPLE 66
4-tert-butyl 2,2-diethyl (4RS,5SR)-5-ethyl-1,3-dioxolane-2,2,4-tricarboxylate $^1$H-NMR(CDCl$_3$) δ:1.08(3H, t, J=7.2 Hz), 1.28(3H, t, J=7.1 Hz), 1.33(3H, t, J=7.1 Hz), 1.47(9H, s), 1.50–1.90(2H, m), 4.20–4.40(4H, m), 4.45–4.55(1H, m), 4.68(1H, d, J=6.2 Hz).

EXAMPLE 67
2,2-diethyl (4RS,5SR)-5-ethyl-1,3-dioxolane-2,2,4-tricarboxylate $^1$H-NMR(CDCl$_3$) δ:1.11(3H, t, J=7.2 Hz), 1.33(3H, t, J=7.1 Hz), 1.35(3H, t, J=7.1 Hz), 1.60–1.90(2H, m), 4.20–4.57(5H, m), 4.78(1H, d, J=6.2 Hz).

EXAMPLE 68
5-tert-butyl 2,2-diethyl (4R,5R)-1,3-dioxolane-2,2,4,5-tetracarboxylate (1) Preparation of tert-butyl diphenylmethyl L-tartarate 9.82 g of L-tartaric acid was dissolved in 100 ml of methanol, and a solution of 10.7 g of diphenyldiazomethane in 50 ml of acetone, was dropwise added at room temperature, followed by stirring for 30 minutes. The solvent was distilled off under reduced pressure. The residue was continuously extracted with chloroform for 2 hours by means of a Soxhlet extractor, and the obtained solution was evaporated to dryness under reduced pressure. The residue was recrystallized from chloroform-hexane. Then, the obtained crystals were washed with hexane to obtain 4.51 g (yield: 26%) of monodiphenylmethyl L-tartarate as white solid.

4.51 g of the above ester was dissolved in 20 ml of tetrahydrofuran, and 7.15 g of O-tert-butyl-N,N-diisopropylisourea was added, followed by stirring at room temperature for 3 days. Insoluble matters were filtered off, and then, the filtrate was concentrated under reduced pressure. The residue was purified by silica gel column chromatography (hexane/ethyl acetate=5/1) to obtain 3.92 g (yield: 74%) of the above identified compound as white solid.

$^1$H-NMR(CDCl$_3$) δ:1.50(9H, s), 3.05(1H, d, J=7.8 Hz), 3.18 (1H, d, J=7.8 Hz), 4.40–4.60(2H, m), 6.96(1H, s), 7.20–7.40(10H, m).

(2) Preparation of 4-tert-butyl 2,2-diethyl 5-diphenylmethyl (4R,5R)-1,3-dioxolane-2,2,4,5-tetracarboxylate 3.92 g of tert-butyl diphenylmethyl L-tartarate was dissolved in 10 ml of dimethoxyethane, and 844 mg of 60% sodium hydride was added at 0° C., followed by stirring at the same temperature for 45 minutes. Then, a solution of 3.37 g of diethyl dibromomalonate in 5 ml of dimethoxyethane, was added, followed by stirring under heating at 80° C. for 12 hours. The reaction solution was cooled to room temperature and then poured into water. The aqueous layer was saturated with sodium chloride and extracted with ethyl ether. The obtained organic layer was washed with a saturated sodium chloride aqueous solution and then dried over anhydrous magnesium sulfate. The drying agent was filtered off. The solvent was distilled off under reduced pressure, and the residue was purified by silica gel column chromatography (hexane/ethyl acetate=7/1→5/1) to obtain 1.73 g (yield: 44%) of the above identified compound as white solid.

$^1$H-NMR(CDCl$_3$) δ:1.18(3H, t, J=7.2 Hz), 1.31(3H, t, J=7.2 Hz), 1.44(9H, s), 4.05–4.13(2H, m), 4.23–4.40(2H, m), 4.92(1H, d, J=3.8 Hz), 5.08(1H, d, J=3.8 Hz), 6.90(1H, s), 7.20–7.40(10H, m).

(3) Preparation of 5-tert-butyl 2,2-diethyl (4R,5R)-1,3-dioxolane-2,2,4,5-tetracarboxylate 6.00 g of 4-tert-butyl 2,2-diethyl 5-diphenylmethyl 1,3-dioxolane-2,2,4,5-tetracarboxylate was dissolved in 90 ml of dioxane, and 1.80 g of a 10% palladium-carbon catalyst was added, followed by catalytic reduction for 12 hours at room temperature under hydrogen normal pressure. The catalyst was filtered off, and the filtrate was evaporated to dryness. The residue was purified by silica gel column chromatography (hexane/ethyl acetate=2/1→chloroform/methanol=9/1) to obtain 3.41 g (yield: 83%) of the above identified compound.

$^1$H-NMR(CDCl$_3$) δ:1.33(3H, t, J=7.3 Hz), 1.34(3H, t, J=7.2 Hz), 1.50(9H, s), 4.28–4.40(4H, m), 4.91(1H, d, J=3.8 Hz), 5.13 (1H, d, J=3.8 Hz).

Compounds of Examples 69 to 72 were obtained by carrying out the same reaction as in Example 68 except that instead of L-tartaric acid used as the starting material in Example 68, D-tartaric acid and meso-tartaric acid were used.

EXAMPLE 69

4-tert-butyl 2,2-diethyl 5-diphenylmethyl (4S,5S)-1,3-dioxolane-2,2,4,5-tetracarboxylate $^1$H-NMR (CDCl$_3$) δ:1.18(3H, t, J=7.2 Hz), 1.31(3H, t, J=7.2 Hz), 1.44(9H, s), 4.05–4.13(2H, m), 4.23–4.40(2H, m), 4.92(1H, d, J=3.8 Hz), 5.08(1H, d, J=3.8 Hz), 6.90(1H, s), 7.20–7.40(10H, m).

EXAMPLE 70

5-tert-butyl 2,2-diethyl (4S,5S)-1,3-dioxolane-2,2,4,5-tetracarboxylate $^1$H-NMR(CDCl$_3$) δ:1.33(3H, t, J=7.3 Hz), 1.34(3H, t, J=7.2 Hz), 1.50(9H, s), 4.28–4.40(4H, m), 4.91(1H, d, J=3.8Hz), 5.13 (1H, d, J=3.8 Hz).

EXAMPLE 71

4-tert-butyl 2,2-diethyl 5-diphenylmethyl (4RS,5SR)-1,3-dioxolane-2,2,4,5-tetracarboxylate $^1$H-NMR(CDCl$_3$) δ:1.20–1.35(15H, m), 4.20–4.35(4H, m), 5.03(1H, d, J7.5 Hz), 5.13(1H, d, J=7.5 Hz), 6.85(1H, s), 7.20–7.40 (10H, m).

EXAMPLE 72

5-tert-butyl 2,2-diethyl (4RS,5SR)-1,3-dioxolane-2,2,4,5-tetracarboxylate $^1$H-NMR(CDCl$_3$) δ:1.20–1.40(6H, m), 1.45(9H, s), 4.20–4.50 (4H, m), 5.05(2H, s).

EXAMPLE 73

Preparation of 5-tert-butyl 2,2-bis{2-(trimethylsilyl)ethyl} (4S,5S)-1,3-dioxolane-2,2,4,5-tetracarboxylate (1) Dibromomalonic acid 8.1 g of malonic acid was dissolved in 10 ml of a 5% hydrobromic acid aqueous solution, and 24.9 g of bromine was slowly dropwise added at a temperature of not higher than 5° C. The reaction solution was brought to room temperature and stirred for 3 hours. Formed crystals were collected by filtration by means of a glass filter, washed with hexane and then dried for 15 hours in a desiccator wherein sodium hydroxide was present, to obtain 12.7 g (yield: 62%) of the above identified compound as white solid.

(2) Dibromomalonic acid dichloride 12.7 g of dibromomalonic acid was suspended in 15 ml of methylene chloride, and 12.6 ml of oxalyl chloride was added at room temperature. Then, three drops of N,N-dimethylformamide were added by a Pasteur pipette. The reaction solution was stirred at the same temperature for 4 hours and then distilled (15 mmHg, 73 to 75° C.) to obtain 12.0 g (yield: 83%) of the above identified compound as orange colored solid.

(3) Preparation of bis{2-(trimethylsilyl)ethyl} dibromomalonate 1.92 ml of 2-(trimethylsilyl)ethanol and 1.86 ml of triethylamine were dissolved in 10 ml of methylene chloride, and a solution of 2.0 g of dibromomalonic acid dichloride in 5 ml of methylene chloride, was added at room temperature. The reaction solution was stirred at the same temperature for 3 hours. Then, insoluble matters were filtered off, and the filtrate was concentrated under reduced pressure. The residue was purified by silica gel column chromatography (hexane/ethyl acetate=5/1) to obtain 2.64 g (yield: 85%) of the above identified compound as white solid.

$^1$H-NMR(CDCl$_3$) δ:0.08(18H, s), 1.05–1.13(4H, m), 4.32–4.42 (4H, m).

(4) Preparation of 5-tert-butyl 2,2-bis{2-(trimethylsilyl)ethyl} 5-diphenylmethyl (4S,5S)-1,3-dioxolane-2,2,4,5-tetracarboxylate The above identified compound was obtained by carrying out the same reaction as in Example 68(2) except that instead of tert-butyl diphenylmethyl L-tartrate used as the starting material in Example 68(2), tert-butyl diphenylmethyl D-tartarate was used, and instead of diethyl dibromomalonate, bis(2-(trimethylsilyl)ethyl} dibromomalonate was used.

$^1$H-NMR(CDCl$_3$) δ:0.01–0.80(18H, m), 0.90–1.10(4H, m), 1.45(9H, s), 4.13(2H, t, J=8.5 Hz), 4.25–4.38(2H, m), 4.85(1H, d, J=3.8 Hz), 5.05(1H, d, J=3.8 Hz), 6.92(1H, s), 7.25–7.40(10H, m).

(5) Preparation of 4-tert-butyl 2,2-bis{2-(trimethylsilyl)ethyl} (4S,5S)-1,3-dioxolane-2,2,4,5-tetracarboxylate The above identified compound was obtained by carrying out the same reaction as in Example 68(3) except that 4-tert-butyl 2,2-bis{2-(trimethylsilyl)ethyl} 5-diphenylmethyl (4S,5S)-1,3-dioxolane-2,2,4,5-tetracarboxylate was used as the starting material.

$^1$H-NMR(CDCl$_3$) δ:0.05(18H, s), 1.02–1.14(4H, m), 1.52 (9H, s), 4.25–4.45(4H, m), 4.88(1H, d, J=3.8 Hz), 5.13(1H, d, J=3.8 Hz).

Reference Example 1

Preparation of N-(tert-butoxycarbonylmethyl)-{(1R,2R)-2-(2-fluoro-4-biphenylyl)-1-methyl-4-phenylbutyl}amine (1) Preparation of 2-fluoro-4-biphenylyl acetone 15.0 g of 4-bromo-2-fluorobiphenyl, 25.8 ml of tributyltin methoxide, 8.96 g of isopropenyl acetate and 0.47 g of dichlorobis{tri(o-tolyl)phosphine}palladium, were dissolved in 100 ml of toluene and refluxed under heating for 2 hours. The reaction solution was left to cool to room temperature, and a saturated potassium fluoride aqueous solution was added, followed by stirring for one hour. Then the solution was subjected to celite filtration and washed with ethyl acetate. The filtrate and the washing liquid were put together. Then, the organic layer was separated and washed with a saturated sodium chloride aqueous solution and then, dried over anhydrous magnesium sulfate. The drying agent was filtered off, and then, the solvent was distilled off under reduced pressure. The residue was purified by silica gel column chromatography (hexane/ethyl acetate=10/1→5/1), followed by treatment with methylene chloride-hexane, to obtain 10.6 g of the above identified compound as yellow solid.

(2) Preparation of 3-(2-fluoro-4-biphenylyl)-5-phenylpentan-2-one 1.93 g of 60% oily sodium hydride was suspended in 70 ml of dimethylformamide, and a solution of 10.0 g of 2-fluoro-4-biphenylyl acetone in 30 ml of dimethylformamide, was added under cooling with ice with stirring, followed by stirring at room temperature for 50 minutes. Then, 7.20 ml of phenethyl bromide was added, followed by stirring at room temperature for 18 hours. The reaction solution was extracted by an addition of water and ethyl ether, and the organic layer was washed with a saturated sodium chloride aqueous solution and then dried over anhydrous magnesium sulfate. The drying agent was filtered off, and then the solvent was distilled off under reduced pressure. The residue was purified by silica gel column chromatography (hexane/ethyl acetate=10/1) to obtain 10.9 g of the above identified compound as a pale yellow oily substance.

(3) Preparation of (2RS,3SR)-3-(2-fluoro-4-biphenylyl)-5-phenylpentan-2-ol 10.9 g of 3-(2-fluoro-4-biphenylyl)-5-phenylpentan-2-ol was dissolved in 100 ml of tetrahydrofuran, and 46.0 ml of a 1M tetrahydrofuran solution of tri-sec-butyllithium borohydride was added under cooling to −78° C. with stirring, followed by stirring at the same temperature for one hour. To the reaction solution, 30 ml of a 4N sodium hydroxide aqueous solution was added under cooling with ice with stirring. Then, 30 ml of a 30% hydrogen peroxide aqueous solution was gradually dropwise added, followed by stirring at 0° C. for 2 hours. The reaction solution was extracted by an addition of ethyl ether and water, and the organic layer was washed with a saturated sodium thiosulfate aqueous solution and a saturated sodium chloride aqueous solution and then, dried over anhydrous magnesium sulfate. The drying agent was filtered off, and then, the solvent was distilled off under reduced pressure. The residue was purified by silica gel column chromatography (hexane/ethyl acetate=5/1) to obtain 10.4 g of the above identified compound as a colorless oily substance.

(4) Preparation of (2S,3R)-3-(2-fluoro-4-biphenylyl)-5-phenylpentan-2-ol 10.4 g of (2RS,3SR)-3-(2-fluoro-4-biphenylyl)-5-phenylpentan-2-ol was dissolved in 100 ml of vinyl acetate, and 4.3 ml of triethylamine was added. Then, 518 mg of immobilized lipase (Toyothium LIP) was added, followed by stirring at room temperature for 5 days. The enzyme was filtered off and washed with ethyl acetate. The filtrate and the washing liquid were put together, and the solvent was distilled off under reduced pressure. The residue was purified by silica gel column chromatography (hexane/ethyl acetate=10/1→5/1) to obtain 5.47 g of (2R,3S)-2-acetoxy-3-(2-fluoro-4-biphenylyl)-5-phenylpentane and 4.79 g of the above identified compound, respectively, as colorless oily substances. The absolute configuration of the above identified compound was determined by Mosher method (J. Am. Chem. Soc., vol. 113, p. 4092 (1991)).

(5) Preparation of (1R,2R)-2-(2-fluoro-4-biphenylyl)-1-methyl-4-phenylbutylamine 4.79 g of (2S,3R)-3-(2-fluoro-4-biphenylyl)-5-phenylpentan-2-ol and 5.64 g of triphenylphosphine were dissolved in 70 ml of tetrahydrofuran, and 3.4 ml of diethyl azodicarboxylate and then 4.6 ml of diphenylphosphoryl azide were added under cooling with ice in a nitrogen atmosphere, followed by stirring at the same temperature for 3 hours. The solvent was distilled off under reduced pressure, and the residue was roughly purified by silica gel column chromatography (hexane/ethyl acetate=10/1) to obtain a crude azide product.

The above azide product was refluxed under heating for 2.5 hours in 77 ml of 10% water-containing tetrahydrofuran together with 4.13 g of triphenylphosphine. The reaction solution was concentrated under reduced pressure, and then, the residue was purified by silica gel column chromatography (chloroform/methanol=50/1→10/1) to obtain 4.33 g of the above identified compound as a colorless oily substance.

(6) Preparation of N-(tert-butoxycarbonylmethyl)-{(1R, 2R)-2-(2-fluoro-4-biphenylyl)-1-methyl-4-phenylbutyl}amine 930 mg of (1R,2R)-2-(2-fluoro-4-biphenylyl)-1-methyl-4-phenylbutylamine was dissolved in 5 ml of dimethylformamide, and 166 mg of potassium carbonate was added. Then, 453 µl tert-butyl bromoacetate was added under cooling with ice, followed by stirring at room temperature for 3.5 hours. The reaction solution was poured into water and extracted with ethyl acetate. The organic layer was washed with water and a saturated sodium chloride aqueous solution and then dried over anhydrous magnesium sulfate. The drying agent was filtered off, and then the solvent was distilled off under reduced pressure. The residue was purified by silica gel column chromatography (hexane/ethyl acetate=5/1) to obtain 849 mg of the above identified compound as a colorless oily substance.

N-(tert-butoxycarbonylmethyl)-{(1S,2S)-2-(2-fluoro-4-biphenylyl)-1-methyl-4-phenylbutyl}amine was obtained by treating (2R,3S)-3-(2-fluoro-4-biphenylyl)-5-phenylpentan-2-ol obtained by alkali hydrolysis of (2R,3S)-2-acetoxy-3-(2-fluoro-4-biphenylyl)-5-phenylpentane obtained in the above (4), in the same manner as in (5) and (6).

Further, the same reactions as in Reference Example 1 were carried out except that instead of tert-butyl bromoacetate used in Reference Example 1(6), the corresponding bromoacetic acid esters were used, to obtain N-(methoxycarbonylmethyl)-{(1R,2R)-2-(2-fluoro-4-biphenylyl)-1-methyl-4-phenylbutyl}amine, and N-(ethoxycarbonylmethyl)-{(1R,2R)-2-(2-fluoro-4-biphenylyl)-1-methyl-4-phenylbutyl}amine.

The same reactions as in Reference Example 1 were carried out except that instead of 4-bromo-2-fluoro-biphenyl used as the starting material in Reference Example 1(1), the corresponding brominated compounds were used, and/or instead of tert-butyl bromoacetate used in Reference Example (6), the corresponding bromoacetic acid esters were used to obtain N-(ethoxycarbonylmethyl)-{(1R,2R)-1-methyl-2-(4-phenoxyphenyl)-4-(3-thienyl)butyl}amine, N-(ethoxycarbonylmethyl)-{(1R,2R)-1-methyl- 3-(3,4-methylenedioxyphenyl)-2-(4-phenoxyphenyl)propyl}amine, and N-(ethoxycarbonylmethyl)-{(1R,2R)-3-(benzo[b]thienyl)-2-(4-biphenylyl)-1-methylpropyl}amine.

Reference Example 2

Preparation of 2,2-di-tert-butyl 1,2,2-cyclopropanetricarboxylate 1.0 ml of methyl acrylate and di-tert-butyl malonate were dissolved in 30 ml of tetrahydrofuran, and 2.83 g of iodine was added, followed by stirring at room temperature for 30 minutes. Then, 36 g of 40% potassium fluoride-alumina was added, followed by stirring for 16 hours. The reaction solution was purified by silica gel column chromatography (hexane/ethyl acetate=5/1) to obtain 3.2 g of a methyl ester of the above identified compound as a colorless oily substance.

800 mg of the above ester was dissolved in 5 ml of tetrahydrofuran, and 1 ml of a 1N sodium hydroxide aqueous solution was added, followed by stirring at room temperature for 4 days. The reaction solution was purified by silica gel column chromatography (hexane/ethyl acetate=1/1→chloroform/methanol=10/1) to obtain 462 mg of the above identified compound as a pale yellow oily substance.

Reference Example 3
Preparation of 3,4-bis(diphenylmethyloxycarbonyl)phenylacetic acid
(1) Preparation of 1,2-dimethyl 1,2,4-benzenetricarboxylate 3.84 g of 1,2,4-benzenetricarboxylic anhydride was dissolved in 60 ml of tetrahydrofuran, and 3.88 g of diphenyldiazomethane was added. The mixture was left to stand at room temperature for 5 hours. To the reaction solution, 0.81 ml of methanol and 0.80 g of 60% oily sodium hydride were added, followed by stirring at room temperature for 3 hours. Then, the solvent was distilled off under reduced pressure. The residue was dissolved in 30 ml of dimethylformamide, and 3.72 ml of methyl iodide and 0.80 g of 60% oily sodium hydride were added, followed by stirring at room temperature for 16 hours. The reaction solution was diluted with diethyl ether, then washed with water and dried over anhydrous magnesium sulfate. Then, the solvent was distilled off under reduced pressure. The residue was purified by silica gel column chromatography (hexane/ethyl acetate=10/1→3/1) to obtain 6.53 g of 1,2-dimethyl 4-diphenylmethyl 1,2,4-benzenetricarboxylate as a colorless oily substance.

6.5 g of the triester obtained as described above, was dissolved in 10 ml of methylene chloride, and 25 ml of trifluoroacetic acid was added, followed by stirring at room temperature for 15 hours. Then, the solvent was distilled off under reduced pressure. The residue was purified by silica gel column chromatography (hexane/ethyl acetate=4/1→1/1) to obtain 3.35 g of the above identified compound.
(2) Preparation of dimethyl 4-hydroxymethylphthalate 1.43 g of 1,2-dimethyl 1,2,4-benzenetricarboxylate was dissolved in 20 ml of tetrahydrofuran, and 20 ml of a 1M tetrahydrofuran solution of a borane-tetrahydrofuran complex, was added, followed by stirring at room temperature overnight. The reaction solution was extracted by an addition of ethyl ether and water, and the organic layer was post-treated in accordance with a usual method. Then, the product was purified by silica gel column chromatography (hexane/ethyl acetate=4/1→1/1) to obtain 1.31 g of the above identified compound as a colorless oily substance.
(3) Preparation of dimethyl 4-cyanomethylphthalate 1.30 g of dimethyl 4-hydroxymethylphthalate was dissolved in 15 ml of ethyl acetate, and 0.58 ml of methanesulfonyl chloride and 1.55 ml of triethylamine were added under cooling with ice with stirring, followed by stirring at room temperature overnight. Insoluble matters were filtered off, and then, the solvent was distilled off under reduced pressure. The residue was dissolved in 13 ml of dimethylformamide, and then, 0.54 g of sodium cyanide was added, followed by stirring at room temperature for 3 hours. The reaction solution was extracted by an addition of ethyl ether and water, and the organic layer was post-treated in accordance with a usual method. Then, the product was purified by silica gel column chromatography (hexane/ethyl acetate=2/1) to obtain 0.78 g of the above identified compound as a colorless oily substance.
(4) Preparation of 4-carboxymethylphthalic acid 0.78 g of dimethyl 4-cyanomethylphthalate was dissolved in a mixed liquid comprising 15 ml of concentrated hydrochloric acid and 4 ml of acetic acid, followed by stirring under heating at 120° C. for 2.5 hours. The reaction solution was left to cool to room temperature and then extracted by an addition of ethyl acetate and water. The organic layer was post-treated in accordance with a usual method to obtain 0.53 g of the above identified compound as white solid.
(5) Preparation of 3,4-bis(diphenylmethyloxycarbonyl)phenylacetic acid 0.52 g of 4-carboxymethylphthalic acid was dissolved in 10 ml of acetone, and a solution of 0.89 g of diphenyldiazomethane in acetone (20 ml) was dropwise added over a period of 15 minutes at room temperature with stirring. After completion of the dropwise addition, the mixture was stirred at room temperature overnight. Then, the solvent was distilled off, and then, the residue was purified by silica gel column chromatography (hexane/ethyl acetate=2/1→ethyl acetate) to obtain 0.67 g of the above identified compound as a colorless oily substance.

Reference Example 4
Preparation of dimethyl 2-(carboxymethyl)-2,3-O-isopropylidene-L-tartarate
(1) Preparation of dimethyl 2-benzyl-2,3-O-isopropylidene-L-tartarate 0.85 ml of diisopropylamine and 25 ml of tetrahydrofuran were mixed, and a 1.67M tetrahydrofuran solution of n-butyllithium was added at −78° C. in a nitrogen atmosphere, followed by stirring at the same temperature for one hour. Then, the temperature was raised to room temperature. Separately, 5 ml of hexamethylphosphoric triamide was added to a solution of 1.10 g of dimethyl 2,3-O-isopropylidene-L-tartarate and 1.30 g of benzyl bromide in 25 ml of tetrahydrofuran, followed by cooling to −78° C. The previously prepared solution was gradually added over a period of 25 minutes. The reaction solution was heated to 3° C. over a period of 4 hours, and 50 ml of a saturated ammonium chloride aqueous solution was added, followed by extraction with ethyl acetate. The organic layer was washed with water and a saturated sodium chloride aqueous solution and then dried over anhydrous sodium sulfate. The drying agent was filtered off, and then the solvent was distilled off under reduced pressure. The residue was purified by silica gel column chromatography (hexane/ethyl acetate=1/1→chloroform/methanol=5/1) to obtain 417 mg of the above identified compound as a colorless oily substance.
(2) Preparation of dimethyl 2-(carboxymethyl)-2,3-O-isopropylidene-L-tartarate 417 mg of dimethyl 2-benzyl-2,3-O-isopropylidene-L-tartarate, 5 ml of carbon tetrachloride, 5 ml of acetonitrile and 7.5 ml of water were mixed, and 2.42 g of disodium hydrogenphosphate 12 hydrate, 1.45 g of sodium periodate and 27 mg of ruthenium chloride were added under cooling with ice, followed by stirring at room temperature for 17 hours. Insoluble matters were filtered off and washed with a saturated sodium hydrogen carbonate aqueous solution and chloroform. The filtrate and the washing liquid were mixed. Then, the aqueous layer was separated. The obtained aqueous layer was acidified (pH 4) with 3N hydrochloric acid and then extracted with ethyl ether. The organic layer was washed with a saturated sodium thiosulfate aqueous solution and a saturated sodium chloride aqueous solution and then, dried over anhydrous magnesium sulfate. The drying agent was filtered off, and then, the solvent was distilled off under reduced pressure to obtain 25 mg of the above identified compound as a colorless oily substance.

Reference Example 5
Preparation of 4-methyl (2RS,4S,5S)-2-ethoxy-1,3-dioxolane-4,5-dicarboxylate (1) Preparation of diphenylmethyl methyl D-tartarate 5.71 g of dimethyl D-tartarate was dissolved in 64 ml of methanol, and 32 ml of a 1N sodium hydroxide aqueous solution was added under cooling with ice, followed by stirring at room temperature for 12 hours. The solvent was distilled off, and then, 80 ml of a 4N hydrochloric acid-dioxane solution was added under cooling with ice. The reaction solution was concentrated and evaporated to dryness. Then, the residue was dissolved in 20 ml of acetone, and a solution of 7.4 g of diphenyl diazomethane in 50 ml of acetone was dropwise added under cooling with ice, followed by stirring at room temperature for 15 hours.

The solvent was distilled off under reduced pressure. Then, the precipitated salt was separated by filtration, and the salt was washed with ethyl acetate. The solvent was distilled off under reduced pressure. The residue was crystallized from ethyl acetate-hexane to obtain 6.71 g of the above identified compound.

(2) Preparation of 5-diphenylmethyl 4-methyl (2RS,4S,5S)-2-ethoxy-1,3-dioxolane-4,5-dicarboxylate 400 mg of diphenylmethyl methyl D-tartarate was dissolved in 7 ml of toluene, and a catalytic amount of Amberlyst 15 and 1 ml of triethyl orthoformate were added, followed by refluxing under heating for one hour. Amberlyst was filtered off. Then, the filtrate was extracted by an addition of water and ethyl acetate. The organic layer was washed with a saturated sodium hydrogen carbonate aqueous solution and a saturated sodium chloride aqueous solution and then, dried over anhydrous magnesium sulfate. The drying agent was filtered off, and then, the solvent was distilled off under reduced pressure. The residue was purified by silica gel column chromatography (hexane/ethyl acetate=5/1) to obtain 195 mg of the above identified compound as a colorless oily substance.

(3) Preparation of 4-methyl (2RS,4S,5S)-2-ethoxy-1,3-dioxolane-4,5-dicarboxylate 190 mg of 5-diphenylmethyl 4-methyl (2RS,4S,5S)-2-ethoxy-1,3-dioxolane-4,5-dicarboxylate was dissolved in 8 ml of ethyl acetate, and 25 mg of a 10% palladium-carbon catalyst was added, followed by catalytic reduction for 15 hours at room temperature under hydrogen normal pressure. The catalyst was filtered off, and then, the filtrate was evaporated to dryness under reduced pressure. The residue was crystallized from hexane to obtain 107 mg of the above identified compound as white solid.

Reference Example 6
Preparation of dimethyl 2-(1-acetoxycarboxymethyl)-2,3-O-isopropylidene-L-tartarate (1) Preparation of dimethyl 2-(1-hydroxy-1-phenylmethyl)-2,3-O-isopropylidene-L-tartarate 0.77 ml of diisopropylamine and 15 ml of tetrahydrofuran were mixed, and 3.2 ml of a 1.68M tetrahydrofuran solution of n-butyllithium was added at −78° C. in a nitrogen atmosphere, followed by stirring at the same temperature for 20 minutes. Then, the temperature was raised to room temperature. Separately, 3 ml of hexamethylphosphoric triamide was added to a solution of 1.09 g of dimethyl 2,3-O-isopropylidene-L-tartarate and 0.61 ml of benzaldehyde in 15 ml of tetrahydrofuran, followed by cooling to −78° C. The previously prepared solution was added over a period of 5 minutes. The reaction solution was stirred at the same temperature for 50 minutes, and then, the temperature was raised to −6° C. over a period of 2.5 hours. Then, ethyl ether and water were added. The organic layer was separated, washed with a saturated ammonium chloride aqueous solution and a saturated sodium chloride aqueous solution and dried over anhydrous sodium sulfate. The drying agent was filtered off, and then, the solvent was distilled off under reduced pressure. The residue was purified by silica gel column chromatography (hexane/ethyl acetate=5/1→2/1) to obtain 113 mg of the above identified compound as a colorless oily substance.

(2) Preparation of dimethyl 2-(1-acetoxy-1-phenylmethyl)-2,3-O-isopropylidene-L-tartarate 113 mg of dimethyl 2-(1-hydroxy-1-phenylmethyl)-2,3-O-isopropylidene-L-tartarate was dissolved in 4 ml of chloroform, and 129 mg of dimethylaminopyridine and 70 μl of acetic anhydride were added, followed by stirring at room temperature for 3 hours. Water and ethyl acetate were added to the reaction solution. The organic layer was separated and sequentially washed with a saturated sodium hydrogen carbonate aqueous solution, water and a saturated sodium chloride aqueous solution and dried over anhydrous sodium sulfate. The drying agent was filtered off, and then, the solvent was distilled off under reduced pressure. The residue was purified by silica gel column chromatography (hexane/ethyl acetate=2/1) to obtain 102 mg of the above identified compound as a colorless oily substance.

(3) Preparation of dimethyl 2-(1-acetoxy-1-carboxymethyl)-2,3-O-isopropylidene-L-tartarate 102 mg of dimethyl 2-(1-acetoxy-1-phenylmethyl)-2,3-O-isopropylidene-L-tartarate, 2 ml of carbon tetrachloride and 2 ml of acetonitrile were mixed, and 3 ml of a 0.25M disodium hydrogenphosphate aqueous solution, 230 mg of sodium periodate and 5.8 mg of ruthenium chloride were added, followed by stirring at room temperature for 27 hours. Water and ethyl ether were added to the reaction solution, followed by stirring for 45 minutes. Then, the aqueous layer was separated and acidified with 1N hydrochloric acid and then extracted with ethyl ether. The organic layer was washed with a 5% sodium thiosulfate aqueous solution and a saturated sodium chloride aqueous solution and then dried over anhydrous sodium sulfate. The drying agent was filtered off, and then, the solvent was distilled off under reduced pressure to obtain 9.6 mg of the above identified compound as a colorless oily substance.

Reference Example 7
Preparation of 4-tert-butyl 2-ethyl (2RS,4R)-1,3-dioxolane-2,2,4-tricarboxylate 300 mg of 4-tert-butyl 2,2-diethyl (4R)-1,3-dioxolane-2,2,4-tricarboxylate (compound obtained by the same treatment as in Example 56(1) to (3) except that instead of D-serine used as the starting material used in Example 56, L-serine was used) was dissolved in a mixed liquid comprising 3 ml of tetrahydrofuran and 2 ml of water, and 0.48 ml of a 1N sodium hydroxide aqueous solution was added, followed by stirring at room temperature for 2 hours. The reaction solution was washed with ethyl ether, and then, the aqueous layer was acidified by an addition of 1N hydrochloric acid and then extracted with ethyl ether. The extract solution was washed with a saturated sodium chloride aqueous solution and dried over anhydrous magnesium sulfate. The drying agent was filtered off, and then, the solvent was distilled off under reduced pressure to obtain 158 mg of the above identified compound as a colorless oily substance.

Reference Example 8
Preparation of 4-tert-butyl 2-ethyl (2R*,4S)-1,3-dioxolane-2,2,4-tricarboxylate (1) Preparation of 2-benzyl 4-tert-butyl 2-ethyl (2R*,4S)-1,3-dioxolane-2,2,4-tricarboxylate, and 2-benzyl 4-tert-butyl 2-ethyl (2S*,4S)-1,3-dioxolane-2,2,4-tricarboxylate 1.03 g of 4-tert-butyl 2,2-diethyl (4S)-1,3-dioxolane-2,2,4-tricarboxylate obtained in Example 56, was dissolved in 4 ml of a 50% tetrahydrofuran aqueous solution, and 1.61 ml of a 1N sodium hydroxide aqueous solution was added, followed by stirring at room temperature for 2 hours. The reaction solution was washed with ethyl ether, and then, the aqueous layer was separated and acidified with 1N hydrochloric acid. After extraction with ethyl ether, the organic layer was dried over anhydrous magnesium sulfate. The drying agent was filtered off, and then, the solvent was distilled off under reduced pressure, and 330 mg of the obtained carboxylic acid was dissolved in 5 ml of chloroform, and 665 mg of O-benzyl-N,N-diisopropylisourea was added, followed by stirring at room temperature for 2.5 days. Insoluble matters were filtered off, and then, the filtrate was concentrated under reduced pressure. The residue was roughly purified by silica gel column chromatography (hexane/ethyl acetate=7/1) and then purified by means of high performance liquid chromatography for fractionation (Senshupak 5301N, hexane/ethyl acetate=6/1) to obtain 218 mg (yield: 36%) of the above identified compound as a preceding fraction of the high performance liquid chromatography named as (2S*,4S)-isomer for the sake of convenience and 40 mg (yield: 7%) of the above identified compound as a later fraction of the high performance liquid chromatography named as (2R*,4S)-isomer for the sake of convenience, respectively, as colorless foams.

(2) Preparation of 4-tert-butyl 2-ethyl (2R*,4S)-1,3-dioxolane-2,2,4-tricarboxylate 218 mg of 2-benzyl 4-tert-butyl 2-ethyl (2R*,4S)-1,3-dioxolane-2,2,4-tricarboxylate was dissolved in 3 ml of 1,4-dioxane, and 20 mg of a 10% palladium-carbon catalyst was added, followed by catalytic reduction for 5 hours at room temperature under hydrogen normal pressure. The catalyst was filtered off, and then, the filtrate was evaporated to dryness under reduced pressure to obtain 136 mg (yield: quantitative) of the above identified compound. Treatment was carried out in the same manner except that instead of 2-benzyl 4-tert-butyl 2-ethyl (2R*,4S)-1,3-dioxolane-2,2,4-tricarboxylate used as the starting material in the above reaction, 2-benzyl 4-tert-butyl 2-ethyl (2S*,4S)-1,3-dioxolane-2,2,4-tricarboxylate was used, to obtain 4-tert-butyl 2-ethyl (2S*,4S)-1,3-dioxolane-2,2,4-tricarboxylate.

INDUSTRIAL APPLICABILITY

The compound of the present invention has excellent protein-farnesyl transferase (PFT) inhibitory activities and is useful as an antitumor agent or an anti-HIV agent.

We claim:
1. A compound of the formula (I), or its pharmaceutically acceptable salt or ester:

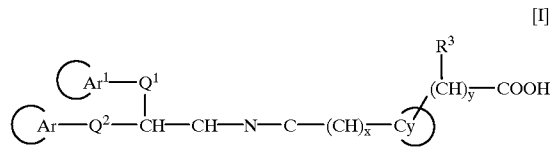

wherein

is an aryl group or a heteroaromatic ring group which may have substituent(s) selected from the group consisting of a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower alkenyl group, a lower hydroxyalkyl group, a lower fluoroalkyl group, a lower alkoxy group, an aryl group and a heteroaromatic ring group;

is a group of the formula

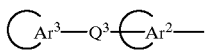

when $Q^2$ is a single bond, or a group of the formula

when $Q^2$ is a group of the formula $-(CH_2)_m-$ or $-(CH_2)_n-W-(CH_2)_p-$; each of

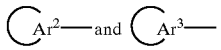

which are the same or different, is an aryl group or a heteroaromatic ring group which may have substituent(s) selected from the group consisting of a halogen atom, a hydroxyl group, an amino group, a nitro group, a cyano group, a carboxyl group, a lower alkoxycarbonyl group, a lower alkylamino group, a carbamoyl group, a lower alkylcarbamoyl group, a lower alkyl group, a lower alkenyl group, a lower hydroxyalkyl group, a lower fluoroalkyl group, a lower alkoxy group and an aralkyloxy group;

is an aryl group, a heteroaromatic ring group or an aliphatic ring group which may contain one or two oxygen atoms, which may have substituent(s) selected from the group consisting of a halogen atom, a hydroxyl group, an oxo group, an amino group, a nitro group, a cyano group, a carboxyl group, a carbamoyl group, a lower alkylcarbamoyl group, a lower carbamoyloxyalkyl group, a lower alkylcarbamoyloxyalkyl group, a lower alkyl group, a lower fluoroalkyl group, a lower hydroxyalkyl group, a lower alkoxy group, a lower alkoxyalkyl group, a sulfo group, a lower alkoxysulfonyl group, a sulfamoyl group, a lower alkylsulfamoyl group, an aryl group, a heteroaromatic ring group and a group of the formula $-PO(OR^4)(OR^5)$; $A^1$ is a $C_{1-4}$ chain hydrocarbon group which may have substituent(s) selected from the group consisting of a halogen atom, a lower alkyl group, a hydroxyl group, a lower hydroxyalkyl group and a lower alkoxy group; m is an integer of from 1 to 6; each of n and p which are the same or different, is an integer of from 0 to 3; $Q^1$ is a single bond, a group of the formula —CH$_2$O—, —OCH$_2$—, —CH$_2$S— or —SCH$_2$—, or a C$_{1-6}$ chain hydrocarbon group which may have substituent(s) selected from the group consisting of a halogen atom and a lower alkyl group; $Q^2$ is a single bond, or a group of the formula —(CH$_2$)$_m$— or —(CH$_2$)$_n$—W—(CH$_2$)$_p$—; $Q^3$ is a single bond, an oxygen atom, a sulfur atom, a methylene group, a vinylene group, or a group of the formula —CO—, —NH—, —COO—, —OCO—, —CH$_2$CH$_2$—, —OCH$_2$—, —SCH$_2$—, —CH$_2$O—, —CH$_2$S—, —NHCO— or —CONH—; $R^1$ is a lower alkyl group; each of $R^2$ and $R^3$ which are the same or different, is a hydrogen atom, a hydroxyl group or a lower alkyl group; each of $R^4$ and $R^5$ which are the same or different, is a hydrogen atom or a lower alkyl group; W is an oxygen atom, a sulfur atom, a vinylene group or an ethynylene group; x is an integer of from 0 to 2; and y is 0 or 1.

2. The compound of claim 1, which is a compound of the formula (I-a)

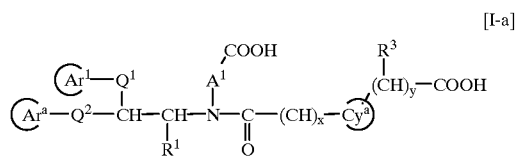

[I-a]

wherein

is an aryl group or a heteroaromatic ring group which may have substituent(s) selected from the group consisting of a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower alkenyl group, a lower hydroxyalkyl group, a lower fluoroalkyl group, a lower alkoxy group, an aryl group and a heteroaromatic ring group;

is a group of the formula

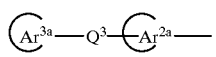

when $Q^2$ is a single bond, or a group of the formula

when $Q^2$ is a group of the formula —(CH$_2$)$_m$— or —(CH$_2$)$_n$—W—(CH$_2$)$_p$—; each of

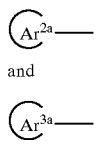

and

which are the same or different, is an aryl group or a heteroaromatic ring group which may have substituent(s) selected from the group consisting of a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower alkenyl group, a lower hydroxyalkyl group, a lower fluoroalkyl group and a lower alkoxy group;

is an aryl group, a heteroaromatic ring group or an aliphatic ring group which may contain one or two oxygen atoms, which may have substituent(s) selected from the group consisting of a halogen atom, a hydroxyl group, an oxo group, an amino group, a carboxyl group, a carbamoyl group, a lower alkylcarbamoyl group, a lower alkyl group and a lower alkoxy group; $A^1$ is a C$_{1-4}$ chain hydrocarbon group which may have substituent(s) selected from the group consisting of a halogen atom, a lower alkyl group, a hydroxyl group, a lower hydroxyalkyl group and a lower alkoxy group; m is an integer of from 1 to 6; each of n and p which are the same or different, is an integer of from 0 to 3; $Q^1$ is a single bond, a group of the formula —CH$_2$O—, —OCH$_2$—, —CH$_2$S— or —SCH$_2$—, or a C$_{1-6}$ chain hydrocarbon group which may have substituent(s) selected from the group consisting of a halogen atom and a lower alkyl group; $Q^2$ is a single bond, or a group of the formula —(CH$_2$)$_m$— or —(CH$_2$)$_n$—W—(CH$_2$)$_p$—; $Q^3$ is a single bond, an oxygen atom, a sulfur atom, a methylene group, a vinylene group, or a group of the formula —CO—, —NH—, —COO—, —OCO—, —CH$_2$CH$_2$—, —OCH$_2$—, —SCH$_2$—, —CH$_2$O—, —CH$_2$S—, —NHCO— or —CONH—; $R^1$ is a lower alkyl group; each of $R^2$ and $R^3$ which are the same or different, is a hydrogen atom, a hydroxyl group or a lower alkyl group; W is an oxygen atom, a sulfur atom, a vinylene group or an ethynylene group; x is an integer of from 0 to 2; and y is 0 or 1.

3. The compound of claim 1, wherein

is a phenyl group, a thienyl group, a naphthyl group, a pyridyl group or a benzothienyl group.

4. The compound of claim 1, wherein

is a phenyl group, a thienyl group or a naphthyl group.

5. The compound of claim 1, wherein

is a phenyl group, a furyl group, a thienyl group or a pyridyl group.

6. The compound of claim 1, wherein

is a phenyl group or a thienyl group.

7. The compound of claim 1, wherein

is a cyclobutyl group, a cyclopentyl group, an oxolanyl group, a 1,3-dioxolanyl group, a phenyl group or a pyridyl group.

8. The compound of claim 1, wherein $Q^1$ is a $C_{1-6}$ chain hydrocarbon group which may have substituent(s) selected from the group consisting of a halogen atom and a lower alkyl group.

9. The compound of claim 1, wherein $Q^2$ is a single bond.

10. The compound of claim 9, wherein $Q^3$ is a single bond, an oxygen atom, a vinylene group or a group of the formula —CO—.

11. The compound of claim 9, wherein $Q^3$ is a single bond.

12. The compound of claim 9, wherein $Q^3$ is an oxygen atom.

13. The compound of claim 9, wherein

is a phenyl group, a furyl group, a thienyl group or a pyridyl group.

14. The compound of claim 9, wherein

is a phenyl group or a thienyl group.

15. The compound of claim 1, which is
(2RS)-2-[N-(carboxymethyl)-N-{(1R,2R)-2-(2-fluoro-4-biphenylyl)-1-methyl-4-phenylbutyl}carbamoyl] cyclopropane-1,1-dicarboxylic acid,
4-[N-(carboxymethyl)-N-{(1R,2R)-2-(2-fluoro-4-biphenylyl)-1-methyl-4-phenylbutyl}carbamoylmethyl] phthalic acid,
4-[N-(carboxymethyl)-N-{(1R,2R)-2-(2-fluoro-4-biphenylyl)-1-methyl-4-phenylbutyl}carbamoyl]phthalic acid,
5-[N-(carboxymethyl)-N-{(1R,2R)-2-(2-fluoro-4-biphenylyl)-1-methyl-4-phenylbutyl}carbamoyl] isophthalic acid,
(4R,5R)-4-[N-(carboxymethyl)-N-{(1R,2R)-2-(2-fluoro-4-biphenylyl)-1-methyl-4-phenylbutyl}carbamoylmethyl]-2,2-dimethyl-1,3-dioxolane-4,5-dicarboxylic acid,
disodium(2R*,4S,5S)-5-[N-(carboxylatomethyl)-N-{(1R,2R)-2-(2-fluoro-4-biphenylyl)-1-methyl-4-phenylbutyl}carbamoyl]-2-ethoxy-1,3-dioxolane-4-carboxylate,
disodium(2S*,4S,5S)-5-[N-(carboxylatomethyl)-N-{(1R,2R)-2-(2-fluoro-4-biphenylyl)-1-methyl-4-phenylbutyl}carbamoyl]-2-ethoxy-1,3-dioxolane-4-carboxylate,
(4R,5R)-4-[N-(carboxymethyl)-N-{(1R,2R)-1-methyl-2-(4-phenoxyphenyl)-4-phenylbutyl}carbamoylmethyl]-2,2-dimethyl-1,3-dioxolane-4,5-dicarboxylic acid,
trisodium(4R,5R)-4-[N-(carboxylatomethyl)-N-{(1R,2R)-1-methyl-2-(4-phenoxyphenyl)-4-phenylbutyl}carbamoylhydroxymethyl]-2,2-dimethyl-1,3-dioxolane-4,5-dicarboxylate,
(4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid,
(4R)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid,
(4S,5S)-4-[N-(carboxymethyl)-N-{(1R,2R)-1-methyl-2-(4-phenoxyphenyl)-4-phenylbutyl}carbamoyl]-5-methyl-1,3-dioxolane-2,2-dicarboxylic acid,
(4R,5R)-4-[N-(carboxymethyl)-N-{(1R,2R)-1-methyl-2-(4-phenoxyphenyl)-4-phenylbutyl}carbamoyl]-5-methyl-1,3-dioxolane-2,2-dicarboxylic acid,
(4S,5R)-4-[N-(carboxymethyl)-N-{(1R,2R)-1-methyl-2-(4-phenoxyphenyl)-4-phenylbutyl}carbamoyl]-5-methyl-1,3-dioxolane-2,2-dicarboxylic acid,
(4R,5S)-4-[N-(carboxymethyl)-N-{(1R,2R)-1-methyl-2-(4-phenoxyphenyl)-4-phenylbutyl}carbamoyl]-5-methyl-1,3-dioxolane-2,2-dicarboxylic acid,
(4R*,5S*)-4-[N-(carboxymethyl)-N-{(1R,2R)-1-methyl-2-(4-phenoxyphenyl)-4-phenylbutyl}carbamoyl]-5-ethyl-1,3-dioxolane-2,2-dicarboxylic acid,
(4S*,5R*)-4-[N-(carboxymethyl)-N-{(1R,2R)-1-methyl-2-(4-phenoxyphenyl)-4-phenylbutyl}carbamoyl]-5-ethyl-1,3-dioxolane-2,2-dicarboxylic acid,
(2S*,4R)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid,
(2R*,4R)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid,
(2S*,4S)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid,
(2R*,4S)-2-[N-(carboxymethyl)-N-{(1R,2R)-1-methyl-2-(4-phenoxyphenyl)-4-phenylbutyl}carbamoyl]-1,3-dioxolane-2,4-dicarboxylic acid,
(2S*,4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid 2-ethyl ester,
(2R*,4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid 2-ethyl ester,
(2S*,4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid 2-ethyl ester,
(2R*,4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid 2-ethyl ester,
(4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid,
(4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid,
(4R*,5S*)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid, (4S*,5R*)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid, (4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid 5-tert-butyl ester, (4S,5S)-4-[N-(carboxymethyl)-N-{(1R,2R)-1-methyl-2-(4-phenoxyphenyl)-4-phenylbutyl}carbamoyl]-5-(N-ethylcarbamoyl)-1,3-dioxolane-2,2-dicarboxylic acid, (4S,5S)-5-carbamoyl-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid, (4S,5R)-4-[N-(carboxymethyl)-N-{(1R,2R)-1-methyl-2-(4-phenoxyphenyl)-4-phenylbutyl}carbamoyl]-5-(hydroxymethyl)-1,3-dioxolane-2,2-dicarboxylic acid, (2S*,4S,5S)-4-[N-(carboxymethyl)-N-{(1R,2R)-1-methyl-2-(4-phenoxyphenyl)-4-phenylbutyl}carbamoyl]-2-(N-ethylcarbamoyl)-1,3-dioxolane-2,5-dicarboxylic acid, (2S*,4S,5S)-4-[N-(carboxymethyl)-N-{(1R,2R)-1-methyl-2-(4-phenoxyphenyl)-4-phenylbutyl}carbamoyl]-2-(N,N-dimethylcarbamoyl)-1,3-dioxolane-2,5-dicarboxylic acid, (4S,5S)-4-[N-(carboxymethyl)-N-{(1R,2R)-1-methyl-2-(4-phenoxyphenyl)-4-phenylbutyl}carbamoyl]-2,2-bis(hydroxymethyl)-1,3-dioxolane-2,5-dicarboxylic acid, (4S)-4-[N-(carboxymethyl)-N-{(1R*,2R*)-2-(3-methoxy-4-phenoxyphenyl)-1-methyl-4-phenylbutyl}carbamoyl]-1,3-dioxolane-2,2-dicarboxylic acid, (4S)-4-[N-(carboxymethyl)-N-{(1S*,2S*)-2-(3-methoxy-4-phenoxyphenyl)-1-methyl-4-phenylbutyl}carbamoyl]-1,3-dioxolane-2,2-dicarboxylic acid, (4S)-4-[N-(carboxymethyl)-N-{(1R*,2R*)-2-(3-hydroxy-4-phenoxyphenyl)-1-methyl-4-phenylbutyl}carbamoyl]-1,3-dioxolane-2,2-dicarboxylic acid, (4S)-4-[N-(carboxymethyl)-N-{(1S*,2S*)-2-(3-hydroxy-4-phenoxyphenyl)-1-methyl-4-phenylbutyl}carbamoyl]-1,3-dioxolane-2,2-dicarboxylic acid, (4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid 2,2-diethyl ester, (4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid 2,2-diethyl ester, (4R)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid 2,2-diethyl ester, (4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid 2,2-bis(pivaloyloxymethyl)ester, (2S*,4S)-4-[N-{(1R,2R)-1-methyl-2-(4-phenoxyphenyl)-4-phenylbutyl}-N-(pivaloyloxymethoxycarbonylmethyl)carbamoyl]-1,3-dioxolane-2,2-dicarboxylic acid 2-pivaloyloxymethyl ester, (2R*,4S)-4-[N-{(1R,2R)-1-methyl-2-(4-phenoxyphenyl)-4-phenylbutyl}-N-(pivaloyloxymethoxycarbonylmethyl)carbamoyl]-1,3-dioxolane-2,2-dicarboxylic acid 2-pivaloyloxymethyl ester, (2S*,4S)-4-[N-{(1R,2R)-1-methyl-2-(4-phenoxyphenyl)-4-phenylbutyl}-N-(pivaloyloxymethoxycarbonylmethyl)carbamoyl]-1,3-dioxolane-2,2-dicarboxylic acid 2-methyl ester, (2R*,4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid 2-methyl ester, (2S*,4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid 2-methyl ester, (4S)-4-[N-(carboxymethyl)-N-{(1R,2R)-2-(2-fluoro-4-biphenylyl)-1-methyl-4-phenylbutyl}carbamoyl]-1,3-dioxolane-2,2-dicarboxylic acid, (4S)-4-[N-(carboxymethyl)-N-{(1R*,2R*)-1-methyl-2-(4-phenoxyphenyl)-4-(3-thienyl)butyl}carbamoyl]-1,3-dioxolane-2,2-dicarboxylic acid, (4S)-4-[N-(carboxymethyl)-N-{(1R*,2R*)-2-(4-phenoxyphenyl)-1-methyl-3-(3,4-methylenedioxyphenyl)propyl}carbamoyl]-1,3-dioxolane-2,2-dicarboxylic acid, (4S)-4-[N-(carboxymethyl)-N-{(1S*,2S*)-2-(4-phenoxyphenyl)-1-methyl-3-(3,4-methylenedioxyphenyl)propyl}carbamoyl]-1,3-dioxolane-2,2-dicarboxylic acid, (4S)-4-[N-(carboxymethyl)-N-{(1R*,2R*)-3-(benzo[b]thienyl)-2-(4-biphenylyl)-1-methylpropyl}carbamoyl]-1,3-dioxolane-2,2-dicarboxylic acid, (4S)-4-[N-(carboxymethyl)-N-{(1S*,2S*)-3-(benzo[b]thienyl)-2-(4-biphenylyl)-1-methylpropyl}carbamoyl]-1,3-dioxolane-2,2-dicarboxylic acid, or (4S)-4-[N-(carboxymethyl)-N-[(1R,2R)-2-{4-(4-bromophenoxy)phenyl}-1-methyl-4-phenylbutyl]carbamoyl]-1,3-dioxolane-2,2-dicarboxylic acid.

16. The compound of claim 1, which is (4S)-4-[N-(carboxymethyl)-N-{(1R,2R)-1-methyl-2-(4-phenoxyphenyl)-4-phenylbutyl}carbamoyl]-1,3-dioxolane-2,2-dicarboxylic acid.

17. The compound of claim 1, which is (4R,5R)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid.

18. The compound of claim 1, which is (4S,5S)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid.

19. The compound of claim 1, which is (4R*,5S*)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid, or (4S*,5R*)-4-[N-(carboxymethyl)-N-{(1R,2R)-1-methyl-2-(4-phenoxyphenyl)-4-phenylbutyl}carbamoyl]-1,3-dioxolane-2,2,5-tricarboxylic acid.

20. An antitumor agent, which comprises a compound of the formula (I), or its pharmaceutically acceptable salt or ester:

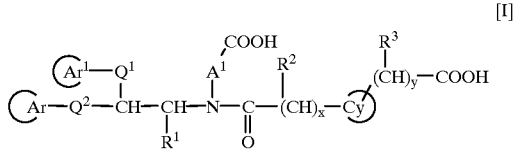

wherein $Ar^1$— is an aryl group or a heteroaromatic ring group which may have substituent(s) selected from the group consisting of a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower alkenyl group, a lower hydroxyalkyl group, a lower fluoroalkyl group, a lower alkoxy group, an aryl group and a heteroaromatic ring group;

is a group of the formula

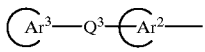

when $Q^2$ is a single bond, or a group of the formula

when $Q^2$ is a group of the formula —(CH$_2$)$_m$— or —(CH$_2$)$_n$—W—(CH$_2$)$_p$—; each of

and

which are the same or different, is an aryl group or a heteroaromatic ring group which may have substituent(s) selected from the group consisting of a halogen atom, a hydroxyl group, an amino group, a nitro group, a cyano group, a carboxyl group, a lower alkoxycarbonyl group, a lower alkylamino group, a carbamoyl group, a lower alkylcarbamoyl group, a lower alkyl group, a lower alkenyl group, a lower hydroxyalkyl group, a lower fluoroalkyl group, a lower alkoxy group and an aralkyloxy group;

is an aryl group, a heteroaromatic ring group or an aliphatic ring group which may contain one or two oxygen atoms, which may have substituent(s) selected from the group consisting of a halogen atom, a hydroxyl group, an oxo group, an amino group, a nitro group, a cyano group, a carboxyl group, a carbamoyl group, a lower alkylcarbamoyl group, a lower carbamoyloxyalkyl group, a lower alkylcarbamoyloxyalkyl group, a lower alkyl group, a lower fluoroalkyl group, a lower hydroxyalkyl group, a lower alkoxy group, a lower alkoxyalkyl group, a sulfo group, a lower alkoxysulfonyl group, a sulfamoyl group, a lower alkylsulfamoyl group, an aryl group, a heteroaromatic ring group and a group of the formula —PO(OR$^4$)(OR$^5$); A$^1$ is a C$_{1-4}$ chain hydrocarbon group which may have substituent(s) selected from the group consisting of a halogen atom, a lower alkyl group, a hydroxyl group, a lower hydroxyalkyl group and a lower alkoxy group; m is an integer of from 1 to 6; each of n and p which are the same or different, is an integer of from 0 to 3; Q$^1$ is a single bond, a group of the formula —CH$_2$O—, —OCH$_2$—, —CH$_2$S— or —SCH$_2$—, or a C$_{1-6}$ chain hydrocarbon group which may have substituent(s) selected from the group consisting of a halogen atom and a lower alkyl group; Q$^2$ is a single bond, or a group of the formula —(CH$_2$)$_m$— or —(CH$_2$)$_n$—W—(CH$_2$)$_p$—; Q$^3$ is a single bond, an oxygen atom, a sulfur atom, a methylene group, a vinylene group, or a group of the formula —CO—, —NH—, —COO—, —OCO—, —CH$_2$CH$_2$—, —OCH$_2$—, —SCH$_2$—, —CH$_2$O—, —CH$_2$S—, —NHCO— or —CONH—; R$^1$ is a lower alkyl group; each of R$^2$ and R$^3$ which are the same or different, is a hydrogen atom, a hydroxyl group or a lower alkyl group; each of R$^4$ and R$^5$ which are the same or different, is a hydrogen atom or a lower alkyl group; W is an oxygen atom, a sulfur atom, a vinylene group or an ethynylene group; x is an integer of from 0 to 2; and y is 0 or 1.

* * * * *